United States Patent [19]
Nakajima et al.

[11] Patent Number: 5,335,547
[45] Date of Patent: Aug. 9, 1994

[54] ULTRASONIC FLAW DETECTOR

[75] Inventors: Kichio Nakajima; Kazuo Honma; Yukio Sumiya; Takeshi Yamaguchi; Hiroshi Inamitsu; Eiji Minamiyama, all of Ibaragi, Japan

[73] Assignee: Hitachi Construction Machinery Co., Ltd., Tokyo, Japan

[21] Appl. No.: 793,392

[22] PCT Filed: Oct. 20, 1990

[86] PCT No.: PCT/JP90/01054

§ 371 Date: Feb. 4, 1992

§ 102(e) Date: Feb. 4, 1992

[87] PCT Pub. No.: WO91/02971

PCT Pub. Date: Mar. 7, 1991

[30] Foreign Application Priority Data

Aug. 21, 1989 [JP] Japan ................... 1-214365
Oct. 9, 1989 [JP] Japan ................... 1-263418

[51] Int. Cl.⁵ ............... G01N 29/10; G01N 29/26
[52] U.S. Cl. ............................. 73/622; 73/620; 73/625; 73/634; 364/508; 364/561; 364/562
[58] Field of Search .......... 73/634, 620, 622, 625, 73/626, 601, 602; 364/508, 561, 562

[56] References Cited

U.S. PATENT DOCUMENTS

| | | | |
|---|---|---|---|
| 2,253,975 | 8/1941 | Guanella | 364/562 |
| 3,678,736 | 7/1972 | May | 73/634 |
| 4,311,052 | 1/1982 | Jeffray et al. | 73/634 |
| 4,403,857 | 9/1983 | Hölscher | 364/561 |
| 4,891,986 | 1/1990 | Teagle | 73/634 |

FOREIGN PATENT DOCUMENTS

| | | | |
|---|---|---|---|
| 0006885 | 1/1985 | Japan | 73/620 |
| 61-240158 | 10/1986 | Japan | . |
| 63-309852 | 12/1988 | Japan | . |
| 0292248 | 11/1989 | Japan | 73/620 |

OTHER PUBLICATIONS

Journal of the Japan Society of Mechanical Engineers, vol. 90 No. 826 New Ultrasonic Testing for Electronic Components and Advanced Materials, pp. 1157–1161.
Journal of JSNDI, The Japanese Society for Non-Destructive Inspection, vol. 37/No. 2A, Feb. 1988 Development of Automatic Ultrasonic Testing System for Curved Shaped Object, pp. 152–153.

*Primary Examiner*—Hezron E. Williams
*Assistant Examiner*—Rose M. Finley
*Attorney, Agent, or Firm*—Cushman, Darby & Cushman

[57] ABSTRACT

The distance sensor means and the ultrasonic probe are integrally coupled to each other in such a manner that a preceding scanning line to a current scanning line which is scanned by the ultrasonic probe is scanned by the distance sensor means, and the shape-measurement scanning operation of the distance sensor means and the flaw-detection scanning operation of the ultrasonic probe are performed in parallel with each other. A flaw detection area is divided into plural sub-areas, and plural storing areas are arranged in a mesh form in one-to-one correspondence to the sub-areas, only one shape information of position storing area including the flaw detection area being stored in each of the storing areas. The position and orientation of the ultrasonic probe at each flaw detection point is controlled using the stored shape information.

14 Claims, 43 Drawing Sheets

FIG. 2A
FIG. 2B
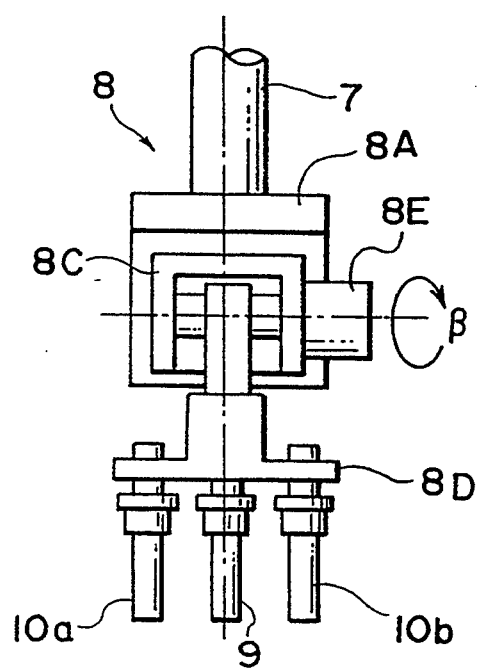
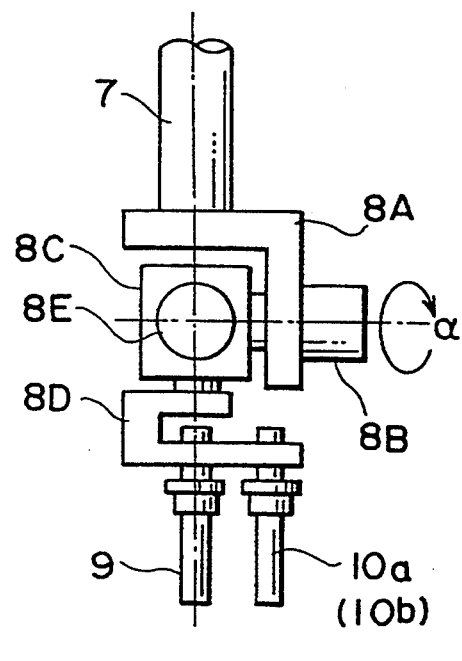

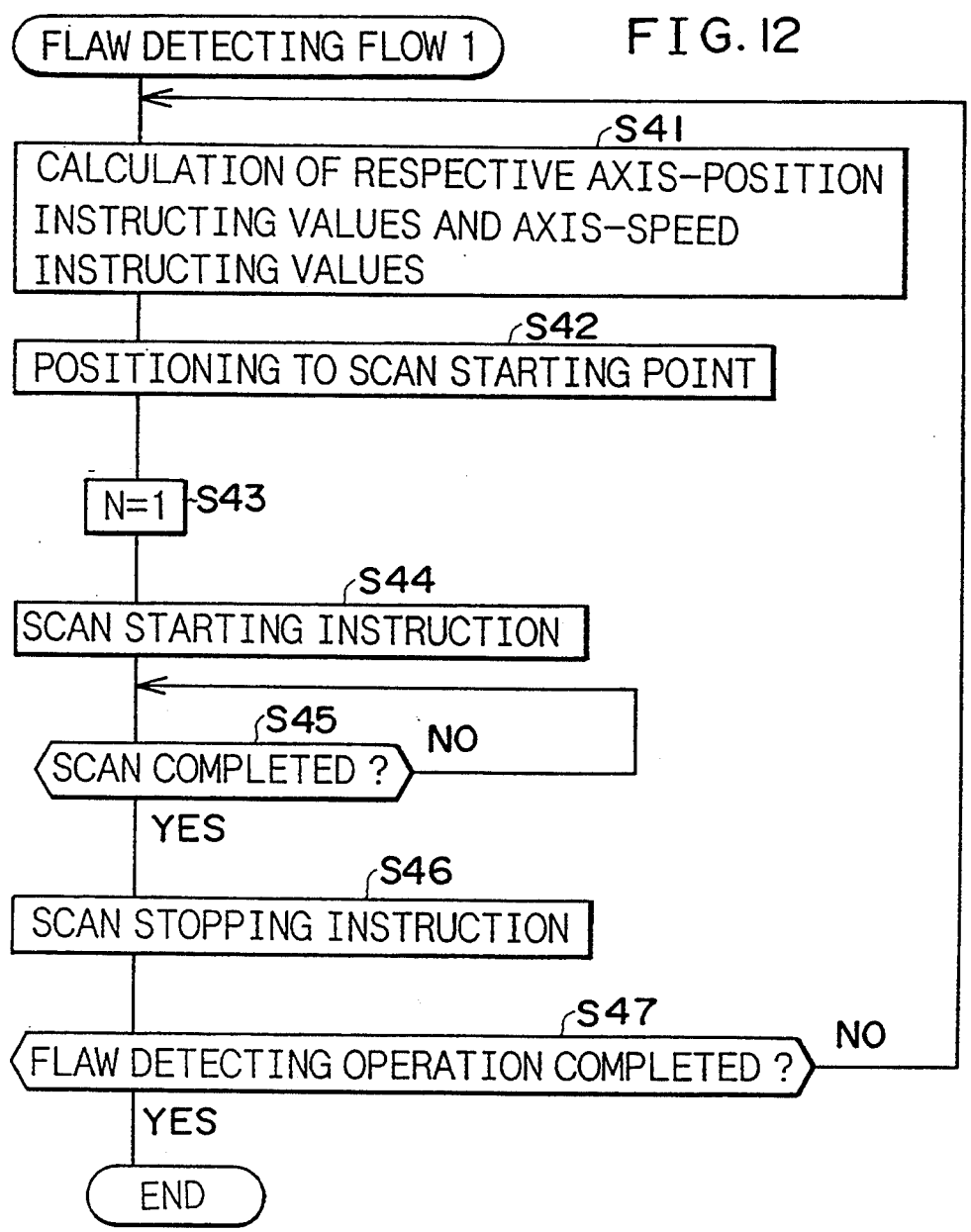

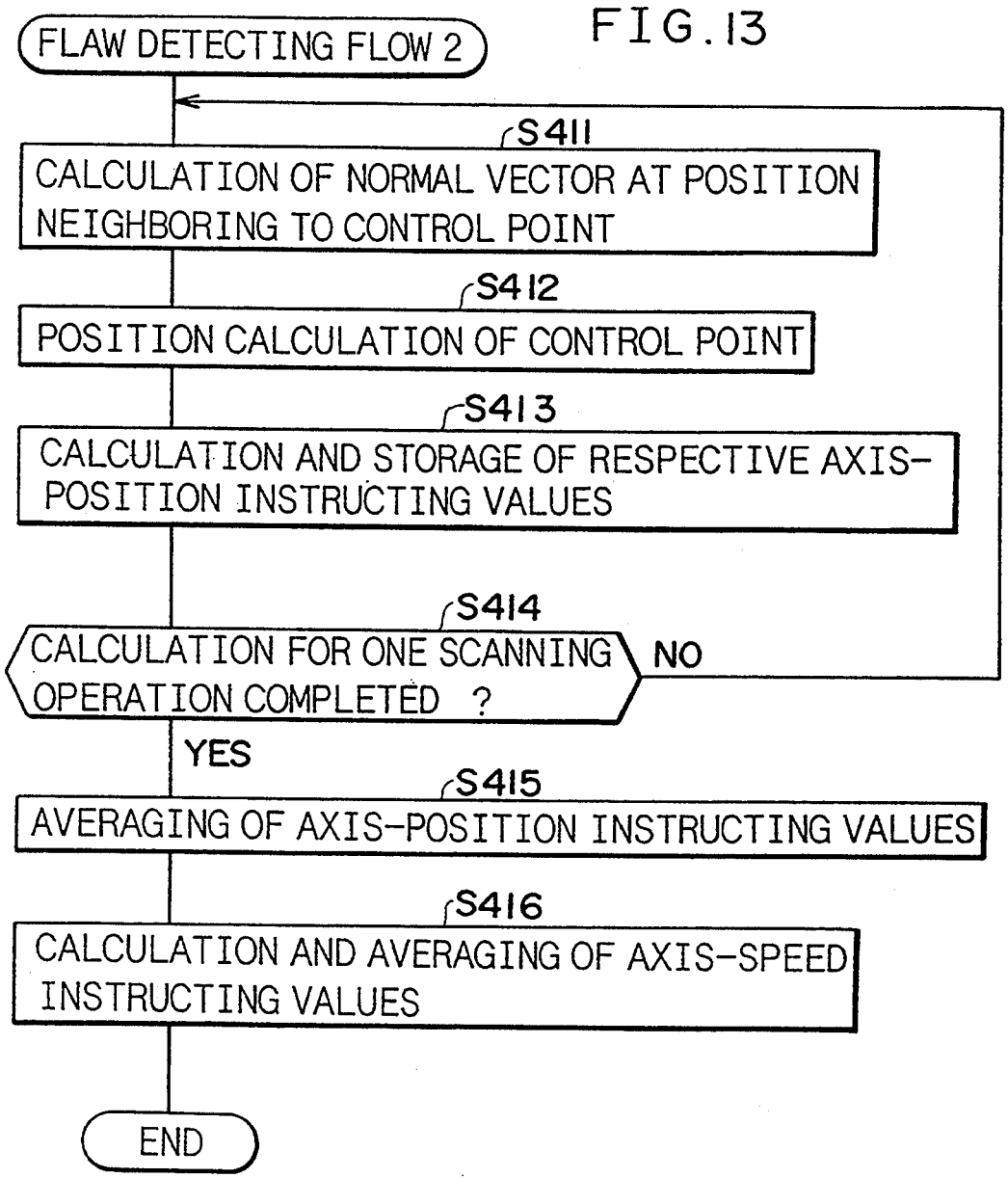

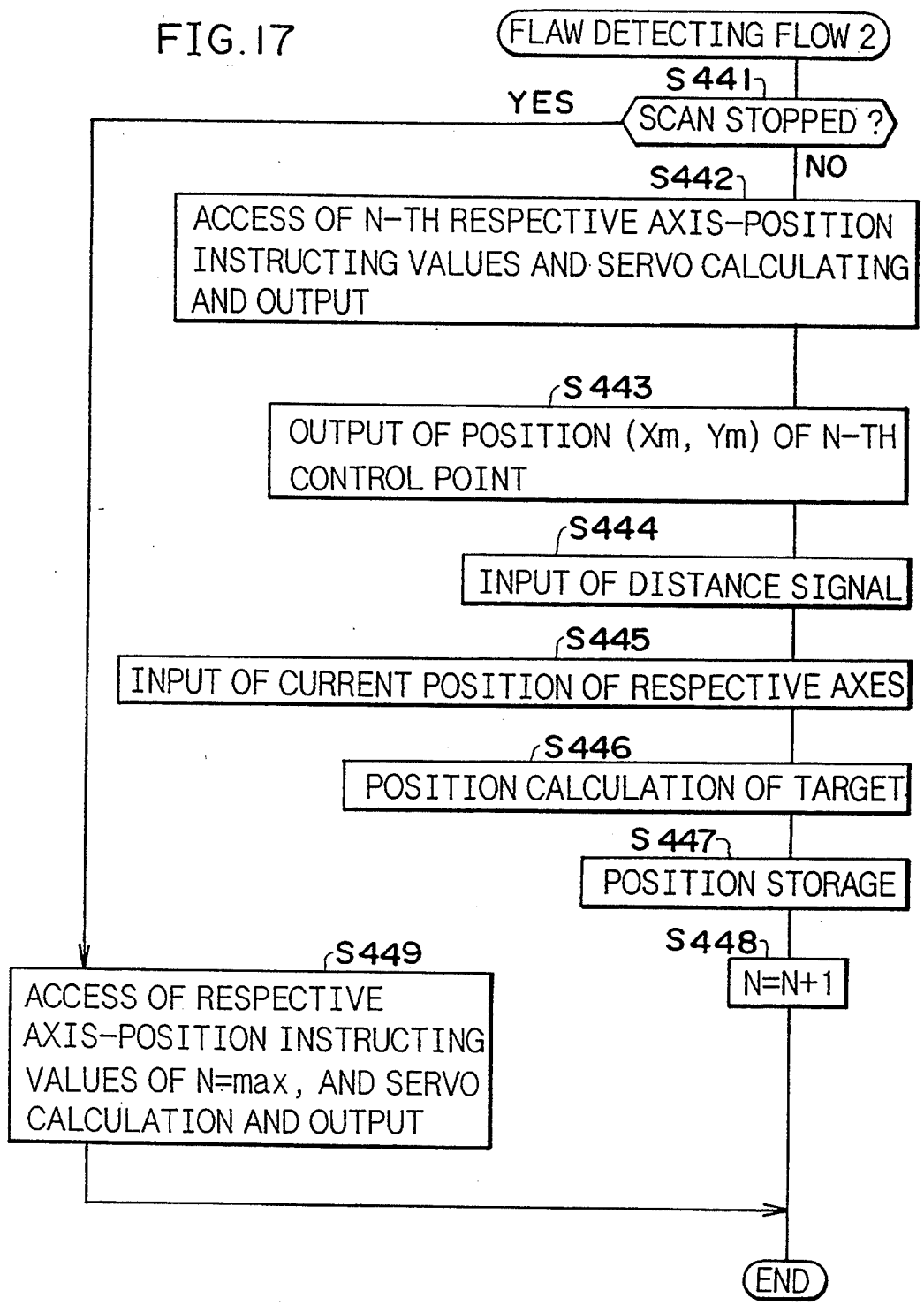

FIG. 21A
FIG. 21B
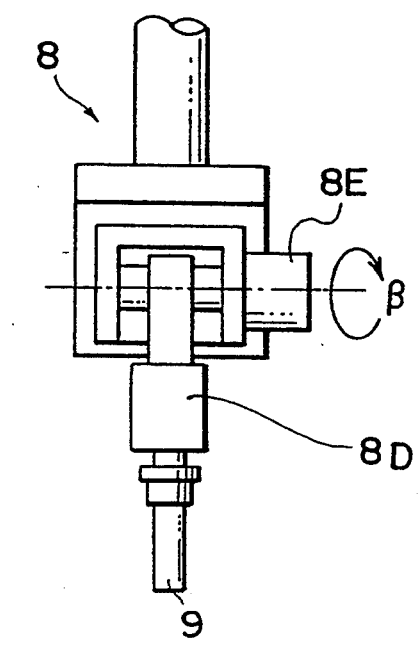
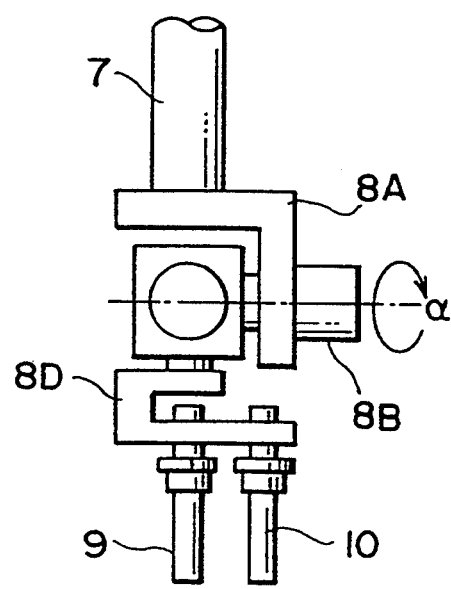
→ X
→ Y

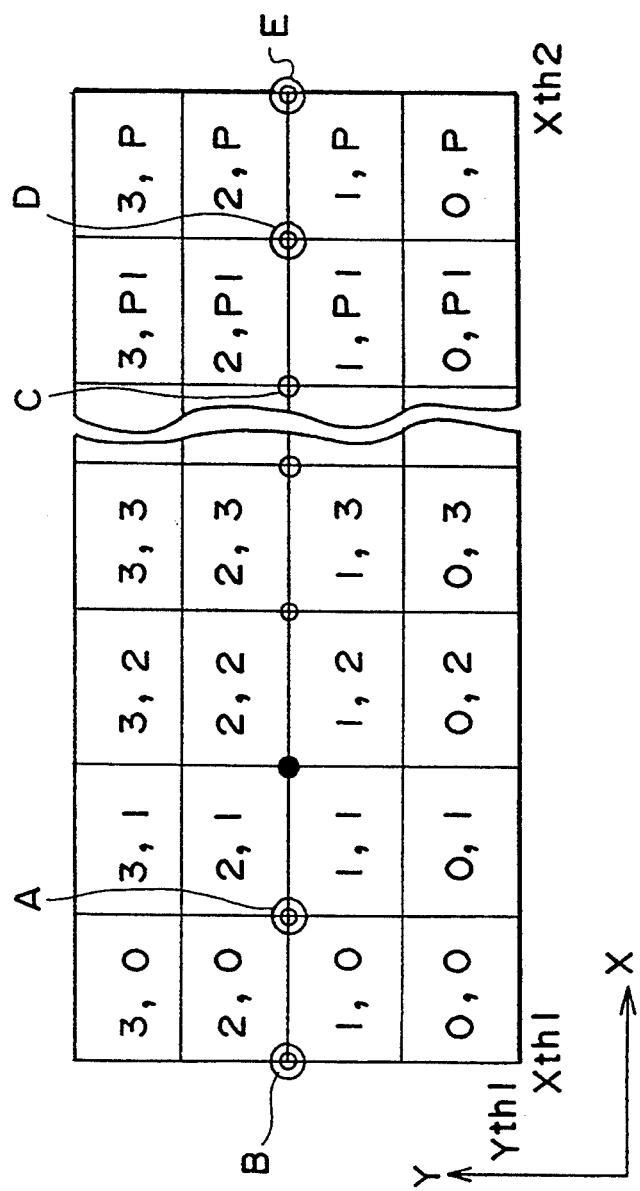

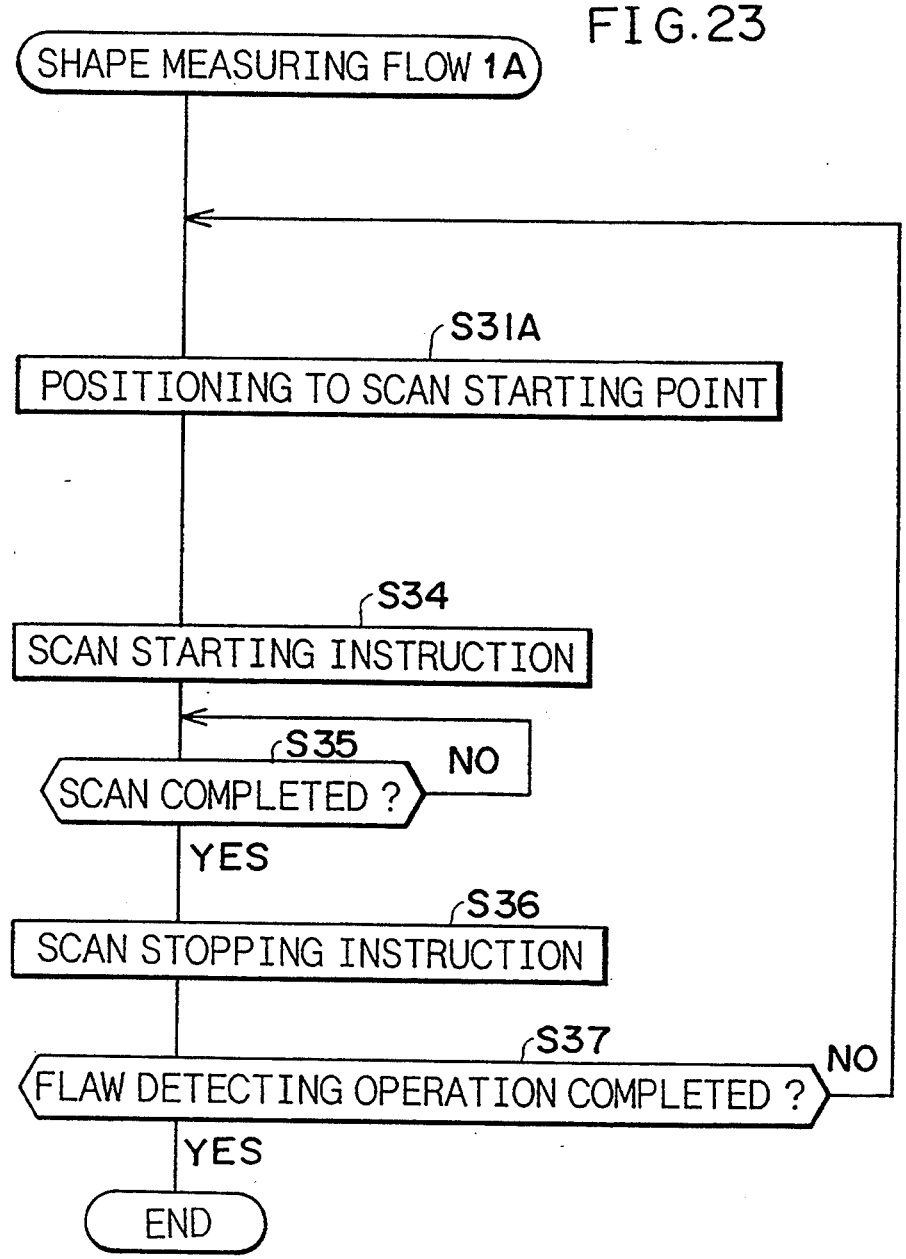

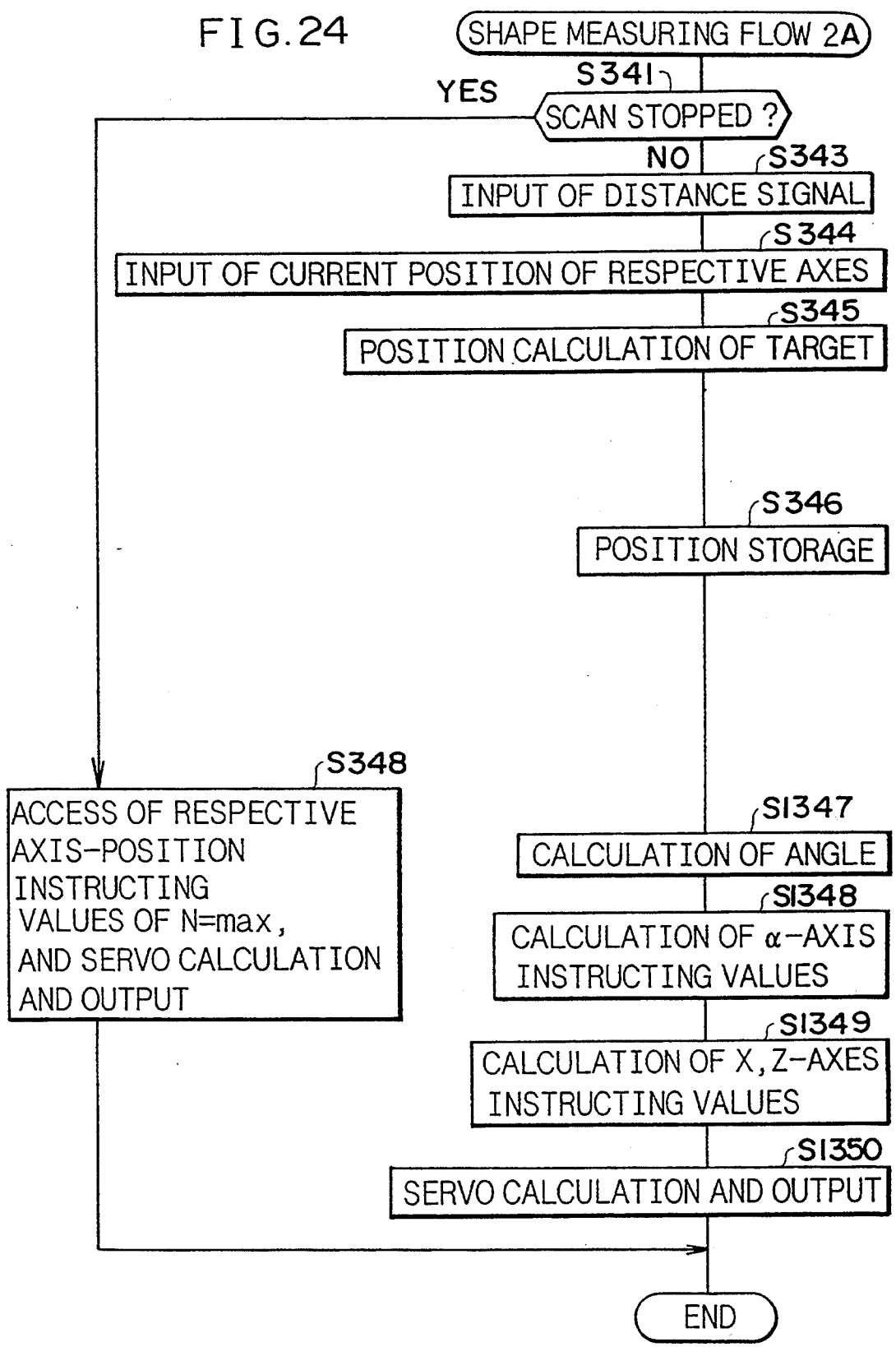

ULTRASONIC FLAW DETECTOR

TECHNICAL FIELD

This invention relates to a flaw detector for detecting a flaw of a target having a curved surface with an ultrasonic probe.

BACKGROUND ART

As a flaw detection method for obtaining information on flaws or defects of a target has been conventionally known an immersion type automatic flaw detection method as disclosed in a journal of the Japan Society of Mechanical Engineers, Vol. 90, No. 826, pp 5–9 (hereinafter, referred to as "prior art 1"), or in a journal of the Japanese Society for Non-destructive Inspection, Vol. 37, No. 2, pp 152–153 (hereinafter referred to as "prior art 2"). These types of flaw detection methods are used to perform precise flaw detection using ultrasonic wave, and mainly includes a process in which a target immersed in water is subjected to flaw detection while an ultrasonic probe is scanned over the surface thereof.

In order to obtain an accurate information on the size and position of a flaw (defect) of the target using the immersion type of automatic flaw detection method as described above, the following two conditions are required. One is that a distance between the ultrasonic probe and the target is kept constant, and the other is that the direction of a center axis of an ultrasonic beam is coincide with the direction of a normal to the surface of the target.

In the prior art 1, the flaw detection can be performed for a target having a plane surface, but not for a target having a curved surface because it is difficult to coincide the direction of the central axis of the ultrasonic beam with the normal direction to the surface of the target. That is, the prior art 1 never satisfies the latter condition for the target having an curved surface.

On the other hand, the prior art 2 includes two steps for the flaw detection, in which the whole shape or profile of a target is beforehand measured using a laser range finder to obtain an information on the shape or profile of the target, and then an ultrasonic probe is scanned in accordance with the information. As described above, this prior art 2 includes the step of beforehand measuring the shape or profile of the target, and thus can perform the flaw detection for an target having any shape or pro-file. This type of ultrasonic flaw detector has been disclosed in Japanese Unexamined Published Patent Applications No. 63-309852 and No. 63-309853 (hereinafter referred to as "JPAs").

However, the prior art 2 and the ultrasonic flaw detector as disclosed in the "JPAs" have the following problems.

As described above, these flaw detectors require a multi-scanning (two-step scanning) operation of the surface of the target using a scanning mechanism, that is, both of a first scanning operation using a laser beam and a second scanning operation using an ultrasonic beam, and thus the flaw detection needs 2 times as long as a time ordinarily required for the flaw detection. In addition, the shape measurement of the target by the laser range finder must be made in air while the ultrasonic flaw detection must be carried out in water, so that the environmental equipment for the whole flaw detection process is complicated and gigantic in construction, and a long time is required for the flaw detection.

It is an object of this invention to provide an ultrasonic flaw detector which can shorten a time required for the whole flaw detection process and improve the accuracy of the flaw detection.

DISCLOSURE OF THE INVENTION

According to this invention, a distance sensor means for performing shape measurement and an ultrasonic probe for performing flaw detection are integrally coupled to each other in such a manner that the distance sensor means scans a scanning line while positionally preceding to the ultrasonic probe, and the shape measurement and the flaw detection are performed in parallel with (simultaneously with) each other. Therefore, when the ultrasonic probe is positionally and orientationally controlled to be located and oriented at a predetermined position with respect to the target, the distance (shape) measurement for the target is surely performed by the distance sensor means. Accordingly, the ultrasonic probe for each of flaw detection points which are successively scanned can be accurately controlled in position and orientation. In addition, the shape or profile of the target can be also measured simultaneously with the flaw detection, so that the flaw detection can be performed through one scanning operation and the efficiency of a flaw detection process can be improved.

According to this invention, a flaw detection area is divided into a plurality of small sub-areas, and plural storing sub-areas are distributed in a mesh (matrix) form in such a manner that each of the storing sub-area is assigned to each of the sub-areas of the target in one-to-one correspondence. Each storing sub-area is supplied to only one position data on the shape of the corresponding sub-area, and stores it. The position and orientation of the ultrasonic probe is controlled every flaw detection point on the basis of this stored shape informations of the sub-areas. Accordingly, a storing capacity can be reduced, and the shape information of any flaw detection point which has not been subjected to the shape measurement by the distance means can be calculated, so that a scanning line for the flaw detection is not required to be coincident with a scanning line for the shape measurement and thus the scanning line for the flaw detection can be freely determined.

According to this invention, the target is mounted on a rotatable turn table, and the ultrasonic probe and the distance sensor means which are integrally coupled to each other are disposed in confront with the peripheral surface of the target to perform scanning operations of the target for the shape measurement and the flaw detection while rotating the target. Accordingly, even a massive cylindrical target having a complicated shape or profile can be simply and accurately subjected to the flaw detection.

According to this invention, axis position instructing values for plural control points are calculated on the basis of the shape informations which are beforehand obtained, and an average value of the axis-position instructing values is used as an axis-position instructing value for each scanning line to be scanned by the ultrasonic probe for the flaw detection, and an axis-speed instructing value for each scanning line is calculated as an average value of the axis-speed instructing values for plural control points. Accordingly, the orientation of the probe at each control point is accurately controlled, that is, the probe is accurately directed to a desired direction, for example, a normal direction to the surface of the target, so that the accuracy of the flaw detection is improved and the probe is smoothly carried out.

According to this invention, in a shape measuring operation of the target while the distance sensor means is oriented (directed) along the normal direction to the surface of the target, when an output of the distance sensor means is judged to be abnormal, the shape information of the target which has been just obtained is interrupted from being stored, and the distance sensor is shifted (scanned) by one pitch while remained to be oriented along a normal direction for a just previous measurement. As a result, if a flaw or defect exists on a surface of the target, a shape information is eliminated. The control of the position and orientation of the probe on the basis of the shape information which excludes abnormal informations due to flaws or defects has the following merits: (a) the probe can be shifted (scanned) while accurately oriented along a desired direction, (b) the probe can be smoothly operated and (c) the probe can be prevented from impinging onto the object.

BRIEF DESCRIPTION OF THE DRAWINGS

FIGS. 1 through 18 show a first embodiment of this invention, and FIG. 1 shows the whole construction of a control system of this invention;

FIGS. 2A and 2B show the fabric of a sensor unit including an ultrasonic probe for flaw detection and a probe for distance measurement;

FIG. 3 shows an arrangement of the ultrasonic probe for flaw detection and the probe for distance measurement;

FIG. 4 is a block diagram of a circuit for distance measurement;

FIG. 5 is a main flowchart;

FIG. 6 is a perspective view of the sensor unit located at an initial position and a target;

FIG. 7 is a flowchart for showing a flow 1 for the shape measurement;

FIG. 8 is a flowchart for showing a flow 2 for the shape measurement;

FIG. 9 shows a relationship between a flaw detection area and a storing area for a shape information;

FIG. 10 is a perspective view of the sensor unit which is in a shape measuring operation;

FIG. 11 is a perspective view of the sensor unit at a start time of the flaw detecting operation;

FIGS. 12, 13 and 17 are flowcharts of showing flows 1, 2 and 3 for the flaw detecting operation, respectively;

FIG. 14 is an explanatory diagram for showing scanning lines for the flaw detection within sub-areas whose shape informations are stored;

FIG. 15 is an explanatory diagram for a coefficient d for calculation of a position data for a control point on the basis of a shape information of a sub-area;

FIG. 16 is a circuit diagram for a position feedback control and a speed feedforward control;

FIG. 18 is an explanatory diagram of parallel operations of the flaw detection and the shape measurement;

FIGS. 21A, 21B and 22 show a second embodiment of this invention, and FIGS. 21A and 21B show a fabric of another sensor unit including an ultrasonic probe for the flaw detection and a probe for the distance measurement;

FIG. 22 is an explanatory diagram for a scanning line for the flaw detection within a sub-area whose shape information is stored;

FIGS. 23 to 25 show a third embodiment of this invention, and FIG. 23 is a flowchart of a flow 1A for the shape measurement;

FIG. 24 is a flowchart of a flow 2 for the shape measurement;

FIG. 25 is an explanatory diagram for performing the shape measurement by a trace-scannning of the surface of the target;

FIGS. 26A to 38 show a fourth embodiment of this invention, and FIGS. 26A and 26B show the whole construction of a control system;

FIG. 28 is an explanatory diagram for showing γa, $D_E$;

FIG. 29 is a perspective view of the sensor unit located at an initial position and the target;

FIG. 30 is a flowchart for a flow 1B for the shape measurement;

FIG. 31 is a flowchart for a flow 2B for the shape measurement;

FIG. 32 is an explanatory diagram for a flaw detection area and a storing area for a shape information;

FIG. 33 is a perspective view of the sensor unit which is in a shape measuring operation;

FIG. 34 is a perspective view of the sensor unit at a start time of the flaw detecting operation;

FIGS. 35, 36 and 38 show flowcharts for showing flows 1A, 2A and 3A for the flaw detecting operation;

FIG. 37 is an explanatory diagram for showing a scanning line for the flaw detection within a sub-area whose shape information is stored;

FIG. 39 is a block diagram for showing a hardware therefor;

FIGS. 40 and 41 show flowcharts for showing processing flows;

FIG. 42 shows the whole construction of the control system;

FIG. 43 is a flowchart for detecting abnormality of a distance signal;

FIG. 44 is a flowchart for a flow 1C for the shape measurement;

FIG. 45 is a flowchart for a flow 2C for the shape measurement;

FIG. 46 is a flowchart for a compensating control processing for distance detection incapability; and FIG. 47 is a flowchart for a flow 3C for the shape measurement.

BEST MODE FOR CARRYING OUT THE INVENTION

First Embodiment

Description of the Whole Construction of the Detector

The whole construction of a first embodiment of a flaw detector according to this invention will be described with reference to FIGS. 1 through 4.

Figure 1:
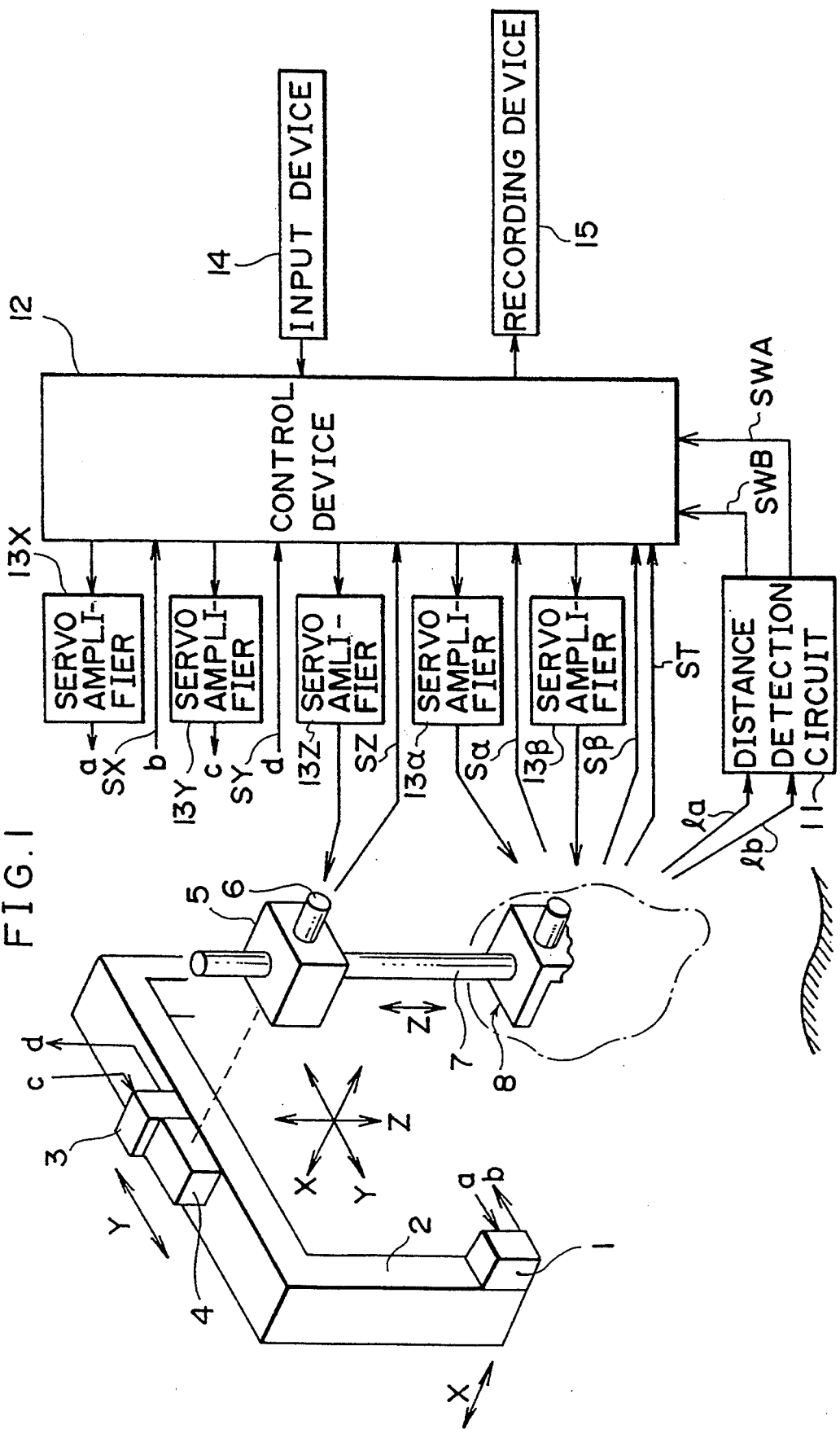

As shown in FIG. 1, the X-axis moving member 2 is of a bridge shape (or of an inverted U-shape) having two legs and one intermediate portion therebetween, and is movable in the X-direction by the X-axis driving member 1. The Y-axis moving member 4 is mounted on the upper surface of the intermediate portion and is movable along the longitudinal direction of the intermediate portion (in the Y-axial direction) by the Y-axis driving member 3. The Z-axis moving member 7 comprises an arm (hereinafter referred to as "Z-axis arm") supported movably by a bracket 5 which is integral with the Y-axis moving member 4, and is movable upwardly and downwardly (in the Z-axial direction). The detection member comprises a handling member 8 secured to the lower end of the Z-axis arm 7.

As shown in FIGS. 2A and 2B, the handling member 8 includes a bracket 8A secured fixedly to the lower end of the Z-axial arm 7, an α-axis driving member 8B secured to the bracket 8A, a bracket 8C secured to the α-axis driving member 8B, a β-axis driving member 8E secured to the bracket 8C, and a bracket 8D secured to the β-axial rotational shaft. The bracket 8D is equipped with two types of detection members one of which is an ultrasonic probe 9 for flaw detection of a target (W) and the other of which is a pair of distance sensor units 10a and 10b each for detecting a current position thereof in the Z-axial direction.

Figure 3:
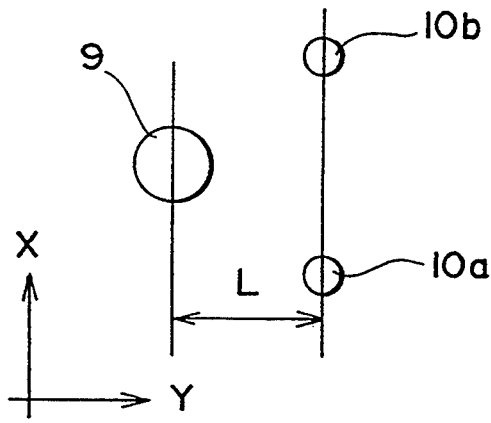

The distance sensor units 10a and 10b and the ultrasonic probe 9 are secured to the bracket 8D in a positional relationship as shown in FIG. 3. Each of the distance sensor units 10a and 10b may comprise an ultrasonic probe. The detection signals of the distance sensor units 10a and 10b are outputted to a distance detection circuit 11 as shown in FIG. 4.

Figure 4:
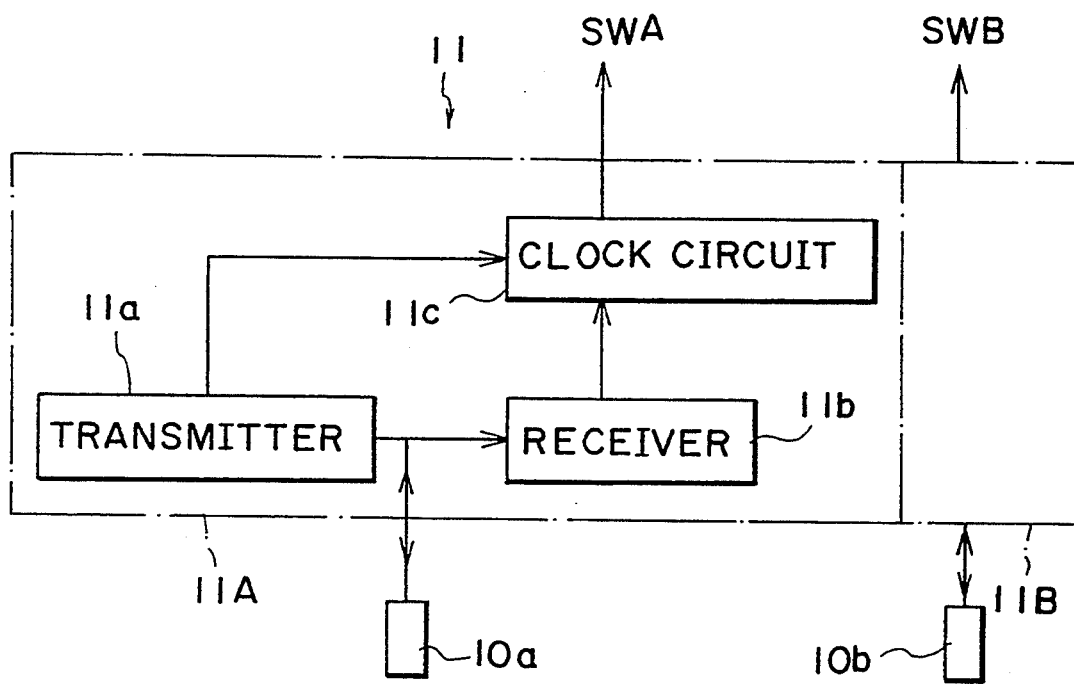

As shown in FIG. 4, the distance detection circuit 11 comprises two distance detection circuits 11A and 11B which are exclusively used for the ultrasonic probes 10a and 10b, respectively, and which have the same circuit construction. When each of the distance sensor units 10a and 10b comprises an ultrasonic probe, each of the distance detection circuits 11A and 11B includes a transmitter 11a for transmitting an ultrasonic signal to the ultrasonic probe 10a (10b), a receiver 11b for receiving the ultrasonic signal reflected from the target W and a clock circuit 11c. The clock circuit 11c serves to measure a time interval from the instantaneous time when the ultrasonic signal is transmitted from the transmitter 11a till the instantaneous time when the ultrasonic signal reflected from the surface of the target W is received by the receiver 11b, and to output a measured result as a distance detection signal SWA (SWB) to the control device 12 as shown in FIG. 1. Representing the time interval between the transmission and reception of the ultrasonic signals and the ultrasonic velocity propagating in water by $t_0$ and V, a distance M between the ultrasonic probe 10a (10b) and the surface of the target W is calculated by the following equation.

$$M = V t_0 / 2 \quad (1)$$

As shown in FIG. 1, the control device 12 is a microprocessor comprising a CPU, a ROM, a RAM and so on, and is supplied not only with the detection signal ST from the ultrasonic probe 9 and the signals SWA and SWB representing the time interval from the distance detection circuits 11, but also with the signals SX, SY, SZ, Sα and Sβ from the position or angle detectors such as a potentiometer (not shown) which are internally provided to the X-, Y-, Z-, α-, and β-axis driving members 1, 3, 6, 8B and 8E, servo amplifiers 13X, 13Y, 13Z, 13α and 13β, respectively, control driving operation of the driving members 1, 3, 6, 8B and 8E. The control device 12 is further connected to an input device 14 for inputting an information on an area to be subjected to the flaw detection (hereinafter referred to as "flaw detection area") and so on, and to a recording device 15 for recording a flaw detection result. Each axis-driving member for performing a linear or rotational motion in each axial-direction may comprise an electrical motor, for example.

Calculating processing of the Control Device 12

(1) Main flow of processing

Figure 5:
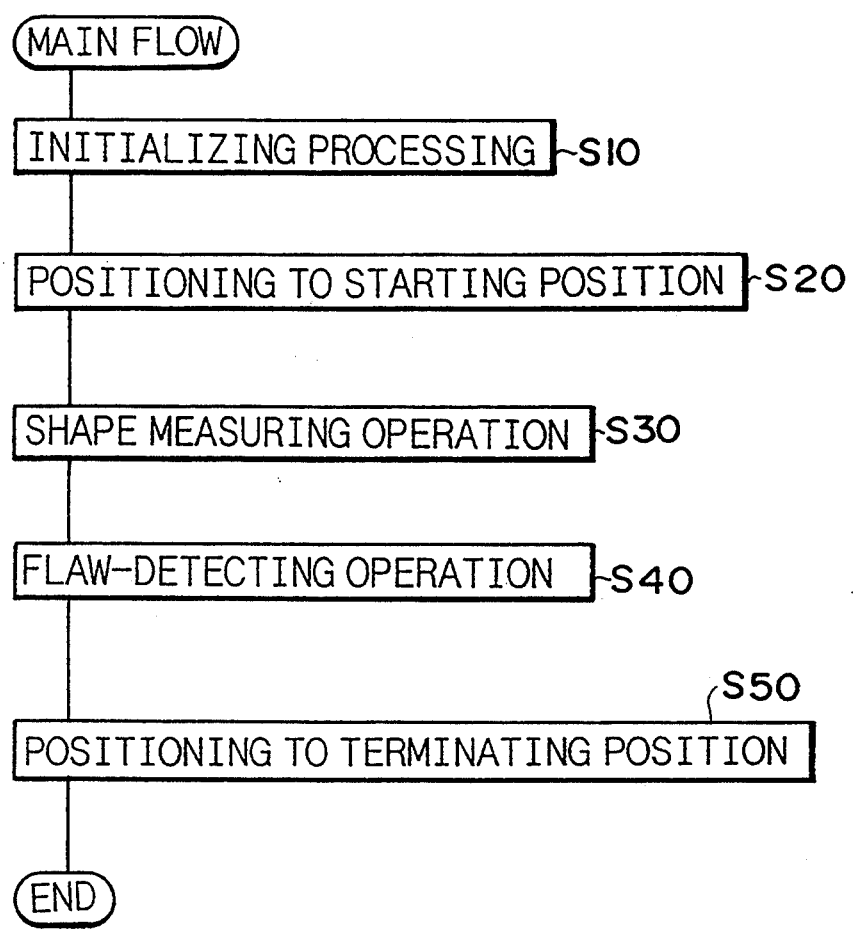

FIG. 5 is a flowchart for processings which are executed by the control device

First, a memory and other elements of the control device 12 are initialized at a step S10, and then the ultrasonic probes 10a and 10b are positioned at a step S20 to a control-starting position by the respective axis-driving members for the respective axes (X-, Y-, Z-, α- and β-axial) as shown in FIG. 1.

Figure 6:
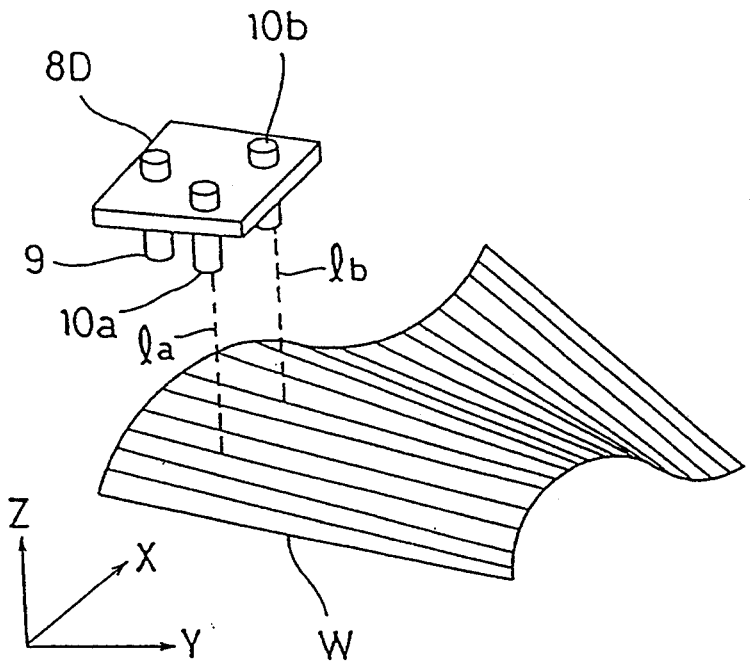

FIG. 6 shows the initial position of the ultrasonic probes 10a and 10b at a state where the initial positioning operation has been completed. Next, the shape measuring operation is started at a step S30, and the ultrasonic probes 10a and 10b are scanned by a predetermined distance in the X-axial direction along the surface of the target W while oriented to a normal direction to the surface of the target W on the basis of a temporary surface shape data of the target W which is beforehand obtained from a design specification. This scanning action of the ultrasonic probes 10a and 10b in the X-axial direction is repeated several times while displaced in the Y-axial direction by a predetermined pitch in a period between the successive scanning operations of the ultrasonic probes 10a and 10b in the X-axial direction, whereby an actual surface shape data for an area having at least length L as shown in FIG. 3 in the Y-axial direction on the target W is obtained prior to the flaw detecting operation for the area. The surface shape of the target W for each X-axial scanning line is calculated on the basis of the signals SX, SY, SZ, Sα and Sβ from the internal position or angle detectors of the respective axis-driving members 1, 3, 6, 8B and 8E and the signals SWA and SWB from the ultrasonic probes 10a and 10b, thereby obtaining the surface shape data for the area. The detailed process of the shape measuring operation as described above is shown in FIG. 7, and described later.

When the shape measuring operation is completed, the processing goes to a step S40 to start a flaw detecting operation. At this step, position data for plural control points which are used to control the ultrasonic probe 9 to confront points on the target W to be subjected to the flaw detection (hereinafter referred to as "flaw detection points") are calculated on the basis of the surface shape data of the target W which is obtained at the step S30, and an ultrasonic flaw-detection signal is input from the ultrasonic probe 9 to the control device 12 at a timing which is controlled or adjusted every control point.

During the flaw detecting operation for a current X-axial scanning line, a distance between the surface of the target W and each of the ultrasonic probes 10a and 10b is also calculated on the basis of the signals from the ultrasonic probes 10a and 10b which positionally precedes the ultrasonic probe 9 by the several scanning lines (by the distance L as shown in FIG. 3), and on the basis of the distance thus obtained and the position data from the position or angle detectors, the surface shape data for the preceding scanning line is obtained in parallel with (simultaneously) the flaw detecting operation for the current scanning line. When the ultrasonic probe 9 arrives on the preceding scanning line whose surface shape data has been already obtained by the distance-measuring ultrasonic probes 10a and 10b, the position data of a control point for the flaw-detecting ultrasonic probe 9 is calculated on the basis of the surface shape data which has been already obtained, and the flaw detecting operation is carried out using the calculated position data. The detailed process of the flaw detecting operation is shown in FIG. 12, and described later. Here, "flaw-detection point" means a point on the target W upon which the ultrasonic wave or signal is irradiated, and "control point" means a position which lies on the normal passing the flaw-detection point and is away from the flaw-detection point on the surface of the object W by a predetermined distance and at which the ultrasonic probe 9 is located for the flaw detecting operation.

Upon completion of the flaw-detecting operation, the ultrasonic probe 9 is moved to a terminal position at a step S50 and all of the processes are finished.

The surface shape measuring operation and the flaw detecting operation will be next described in more detail.

(2) Process of the shape measuring operation

Figure 7:
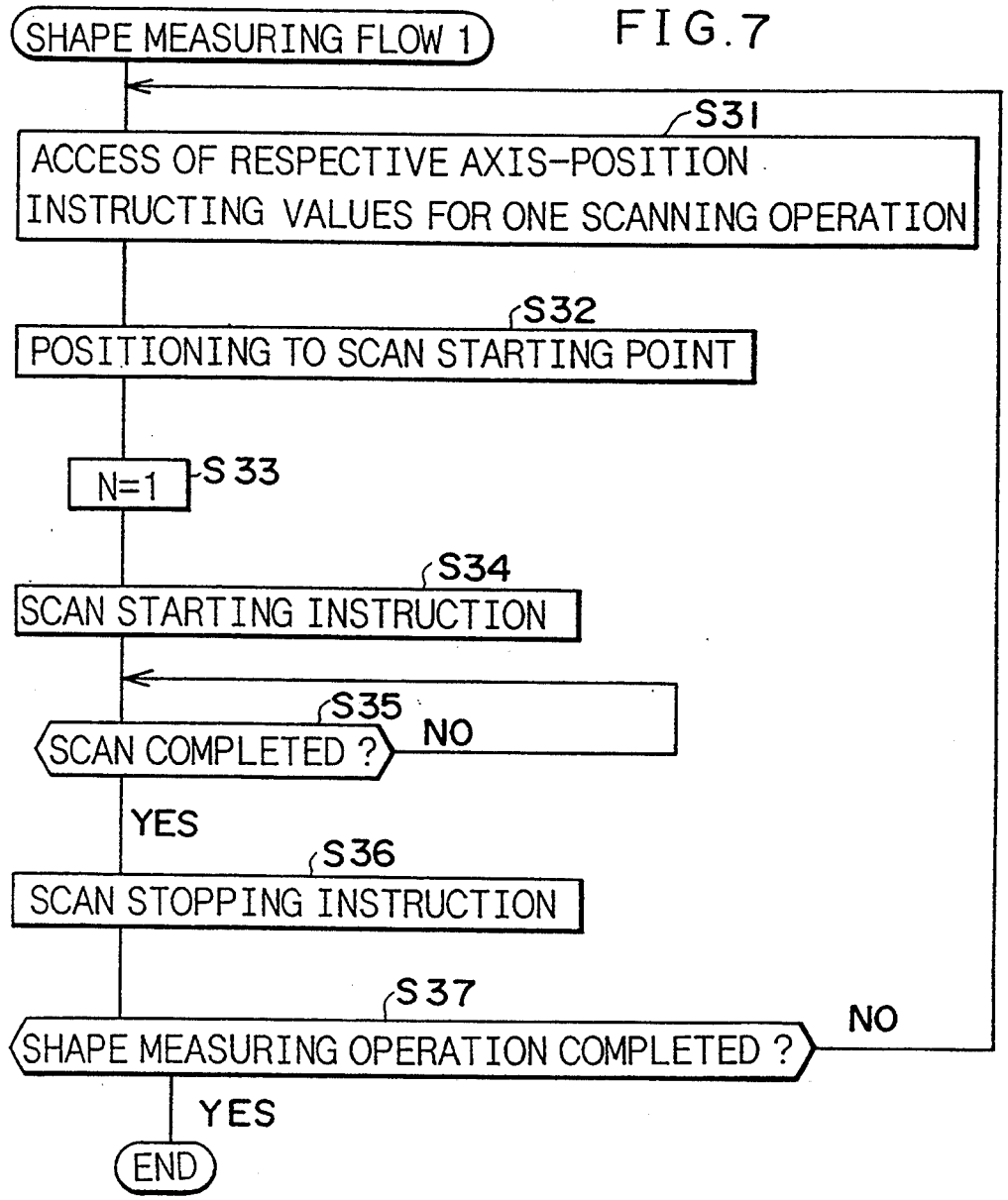

FIG. 7 is a detailed flowchart for the shape measuring operation of the step S30 of FIG. 5.

At a step S31, instructing values for the respective axis-driving members for one scanning operation (hereinafter referred to as "axis-position instructing values") are accessed and stored in a memory. The axis-position instructing value for each axis-driving member for one scanning operation is composed of a data group represented by each of the following equations (2) to (6).

$$Xr=(Xs, X_1, \ldots, X_n, \ldots, X_{max}) \quad (2)$$

$$Yr=(Ys, Y_1, \ldots, Y_n, \ldots, Y_{max}) \quad (3)$$

$$Zr=(Zs, Z_1, \ldots, Z_n, \ldots, Z_{max}) \quad (4)$$

$$\alpha r=(\alpha s, \alpha_1, \ldots, \alpha_n, \ldots, \alpha_{max}) \quad (4)$$

$$\beta r=(\beta s, \beta_1, \ldots, \beta_n, \ldots, \beta_{max}) \quad (6)$$

High accuracy is not required for the axis-position instructing value for the shape measuring operation as described above in comparison with axis-position instructing values for the flaw detecting operation as described later, and therefore it is sufficient to determine representative positions on one scanning line from the design specification data for the target W and then to obtain axis-position instructing values for any position which is interpolatively calculated from the representative positions.

Next, at a step S32 all of the axis-driving members are controlled to be positioned to the respective scan-start positions by setting the axis instruction values Xr, Yr, Zr, $\alpha r$, and $\beta r$ to Xs, Ys, Zs, $\alpha s$, and $\beta s$, respectively. After the above positioning operation is completed, a variable N is set to 1 at a step S33, and then the process goes to a step S34 to output a scan-starting instruction signal. In response to the output of a signal at the step S34, a timer interrupting program as shown in FIG. 8 is executed at a constant time interval.

Figure 8:
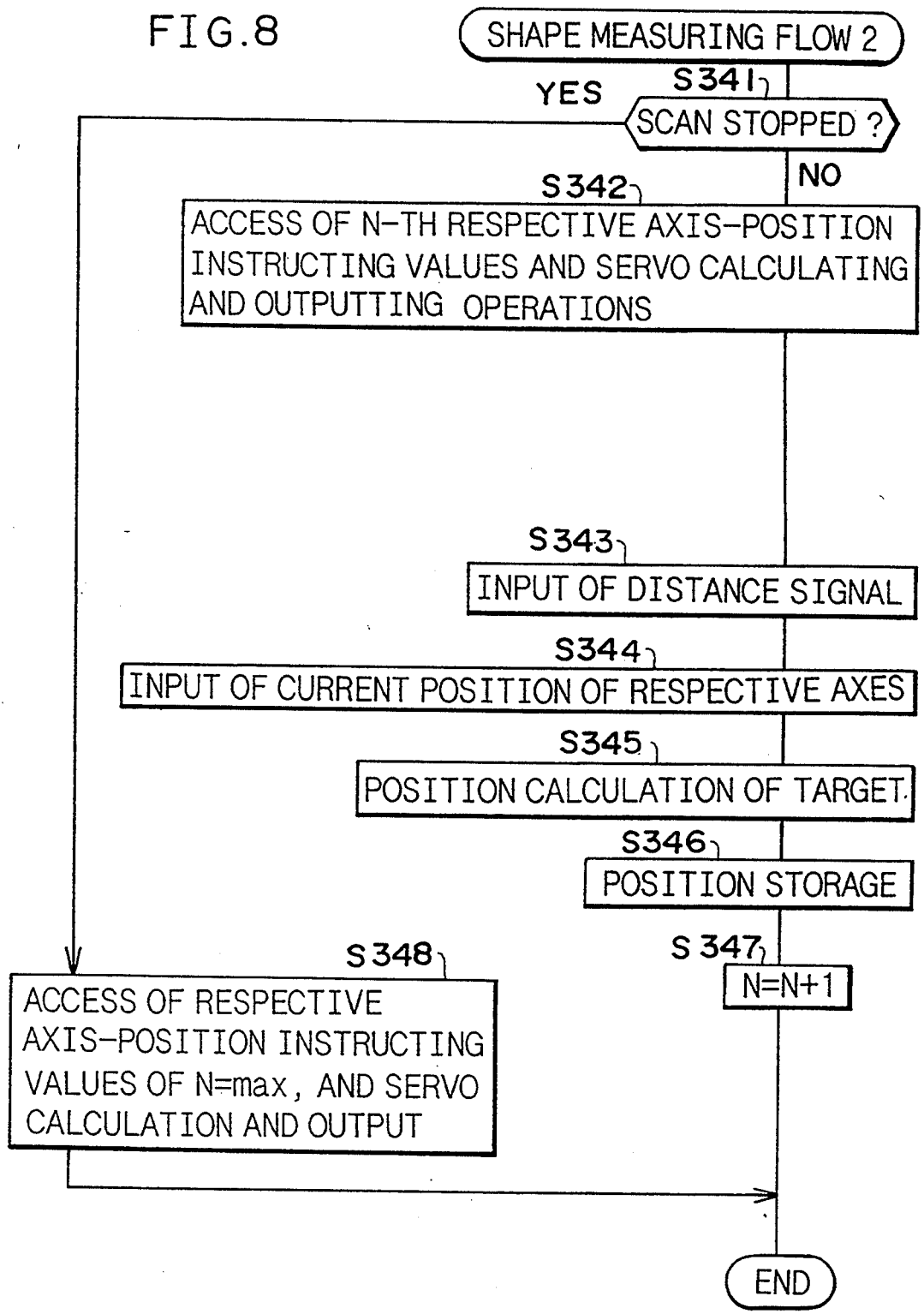

As shown in FIG. 8, it is first judged at a step S341 as to whether an scan-stopping instruction signal is outputted. At a first stage, the scan-stopping instruction signal is not judged to be outputted because at the first stage the scan-starting instruction signal is outputted, and thus the process goes to a step S342 to access the N-th axis-position instructing values (in this case, N=1), that is, $Xr=Xs$, $Yr=Ys$, $Zr=Zs$, $\alpha r=\alpha s$, $\beta r=\beta s$. In addition, the signals SX, SY, SZ, $S\alpha$ and $S\beta$ which represent current positions of the respective axes are input through the respective position or angle detectors to calculate current positions ($X_0$, $Y_0$, $Z_0$, $\alpha_0$ and $\beta_0$) of the axes (X-, Y-, Z-, $\alpha$- and $\beta$-axes). Thereafter, respective differences (deviations) between the axis-position instruction values and the current positions ($X_0$, $Y_0$, $Z_0$, $\alpha_0$ and $\beta_0$) of the axes (X-, Y-, Z-, $\alpha$- and $\beta$-axes) are calculated, and each of the differences (deviations) thus calculated is multiplied by a coefficient, whereby a servo computing operation is carried out. The servo-computed result is outputted to the servo amplifiers 13X to 13$\beta$ to perform a position servo-control for the respective axes. Through the above processes, the ultrasonic probes 10a and 10b are moved to an indicated first position. At this time, the ultrasonic probes 10a and 10b are oriented (directed) to the normal direction to a point on the surface of the target W to be measured (hereinafter referred to as "a shape measuring point"). At a step S343, the distances la and lb between the surface of the target W and both of the ultrasonic probes 10a and 10b are calculated on the basis of the distance detection signals SWA and SWB from the distance detection circuit 11.

Next, the signals SX, SY, SZ, $S\alpha$ and $S\beta$ for the respective axes are input through the respective position or angle detectors at a step S344, and the current positions ($X_0$, $Y_0$, $Z_0$, $\alpha_0$ and $\beta_0$) of the respective axes (X-, Y-, Z-, $\alpha$- and $\beta$-axes) are calculated at a step S345. On the basis of these current positions for the respective axes and the calculated distances la and lb are also calculated three-dimensional positions (Xa, Ya, Za) and (Xb, Yb, Zb) on the surface of the target W to which the ultrasonic beams are radiated from the ultrasonic probes 10a and 10b, respectively. Here, the values Xa to Zb are calculated by the following equations.

$$Xa=f1(X_0, Y_0, Z_0, \alpha_0, \beta_0, la) \quad (7)$$

$$Ya=f2(X_0, Y_0, Z_0, \alpha_0, \beta_0, la) \quad (8)$$

$$Za=f3(X_0, Y_0, Z_0, \alpha_0, \beta_0, la) \quad (9)$$

$$Xb=f1(X_0, Y_0, Z_0, \alpha_0, \beta_0, lb) \quad (10)$$

$$Yb=f1(X_0, Y_0, Z_0, \alpha_0, \beta_0, lb) \quad (11)$$

$$Zb=f3(X_0, Y_0, Z_0, \alpha_0, \beta_0, lb) \quad (12)$$

Thereafter, at a step S346, the surface position on the target W which is calculated using the equations (7) to (12) is stored as a surface shape data in the memory. An example of a storing manner of the surface shape data in the memory will be described with reference to FIG. 9.

Figure 9:
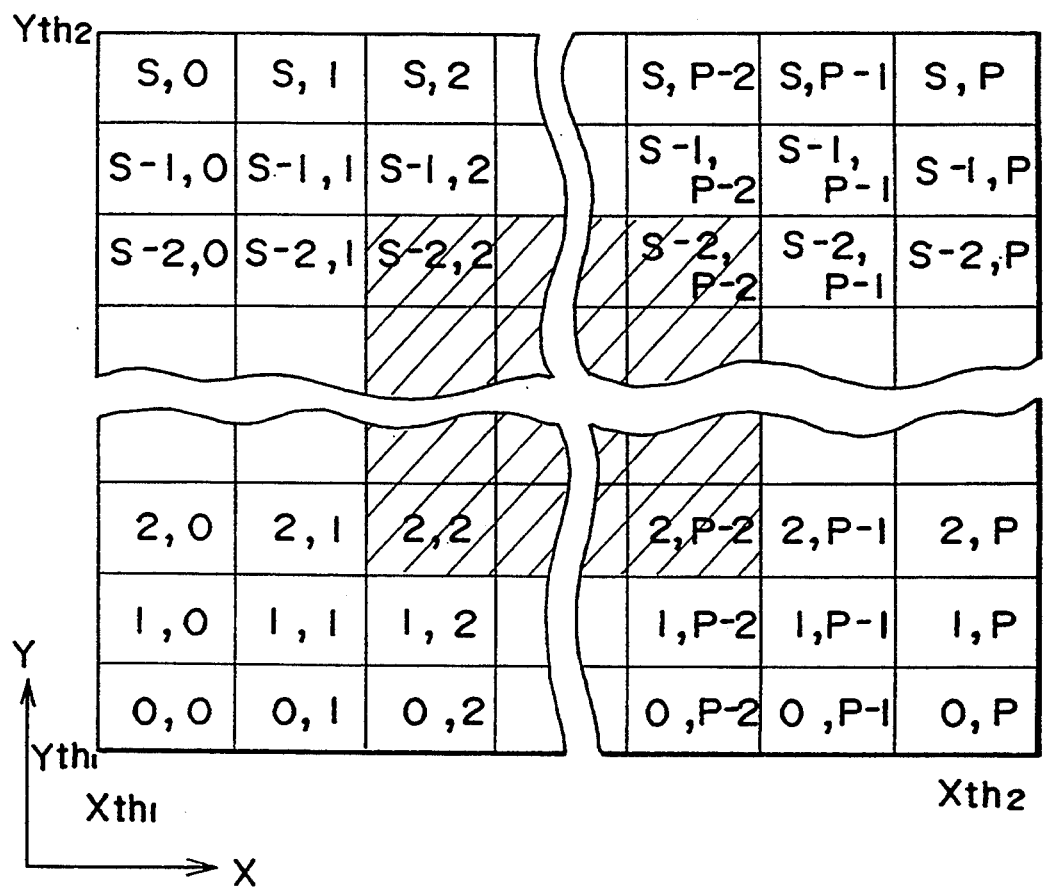

FIG. 9 shows the segmentation (mapping) of the storing area in which data on the surface position (that is, the surface shape data) as described above are stored. The mapping of the storing area is performed by dividing the storing area into plural storing segments (storing sub-areas) which are arranged in correspondence with an X-Y coordinate plane. An oblique area as shown in FIG. 9 corresponds to an area on the target W to be subjected to the flaw detection in the X-Y coordinate plane (hereinafter referred to as "flaw-detection area"). The storing area for the flaw-detection area, which is surrounded by the X-axis ranging from a position Xth1 to a position Xth2 and the Y-axis ranging from a position Yth1 to a position Yth2 as shown in FIG. 9, is designed to be slightly larger than the flaw-detection area, and is segmented into plural storing sub-areas arranged in a matrix form. That is, as shown in FIG. 9, the storing area includes storing sub-areas (Xth1 to Xth2) of (P+1) in the X-direction and storing sub-areas (Yth1 to Yth2) of (S+1) in the Y-direction.

A storing sub-area which is designed to positionally contains the position coordinates Xa and Ya obtained by the equations (7) and (8) is specified using the mapping thus constructed, and the data of Xa, Ya, Za and a flag representing the end of a storing operation are stored as a position data in the corresponding storing sub-area. The surface positions Xb, Yb and Zb obtained by the equations (10) to (12) are also subjected to the same process as described above.

It is not necessarily required for the storing manner that a segment interval between neighboring storing sub-areas is coincident with a measuring interval between neighboring measuring points for the distance measurement, and any other storing manners may be adopted. For example, if the measuring interval is set to be shorter than the segment interval, a position data to be stored within one storing sub-area would be densified. On the other hand, if the measuring interval is set to be longer than the segment interval, there are some storing sub-areas in which no position data is stored.

Further, since the ultrasonic probes 9, 10a and 10b for the shape measuring operation and the flaw detecting operation are integrally actuated with each other, the orientation of the probe 9 in the normal direction to the surface of the target W also enables orientation of the probes 10a and 10b in a direction close to the normal direction to a shape measuring point, so that an reliable distance data can be easily obtained.

In the conventional flaw detector as disclosed in the Japanese publications as described above, an ultrasonic probe for the flaw detection and a distance sensor unit are integrally mounted on a substrate which is triaxially controllable in the X-, Y- and Z-axial directions, and only the ultrasonic probe for the flaw detection is biaxially controllable. In a case where the shape measuring operation is carried out in parallel (simultaneously) with the flaw detecting operation in the conventional mechanism as described above, the distance sensor unit and the multi-axially controlled ultrasonic probe are independently controlled in position and orientation, and thus there occurs a case where a measuring point of the triaxially-controllable distance sensor is more fluctuated when the ultrasonic probe for the flaw detection is controlled to be oriented in the normal direction to a flaw detection point and to be kept away from the surface of the target by a constant distance. This fluctuation of the measuring point frequently disturbs a measurement of the shape of the predetermined measuring point. However, this embodiment as described above can overcome such a disadvantage.

When, in the successive sub-scanning operation along the x-axial direction for the shape measurement, a position data obtained through a current scanning operation (for example, a second scanning operation for N=2) is judged to belong to a storing sub-area in which a position data obtained through a previous scanning operation (a scanning operation for N=1) has been stored, one of the following manners, for example, may be selected because only one position data must be stored in each storing sub-area.

(1) The content of the storing sub-area is renewed and the current position data is newly stored as a position data in the storing sub-area.

(2) The content of the storing sub-area is not renewed, and thus the previous position data remains as a position data in the storing sub-area.

(3) The content of the storing sub-area is renewed, and an average of the previous and current position data is newly stored as a position data in the storing sub-area After one scanning operation is completed, the process goes to a step S347 as shown in FIG. 8 to add "1" to the variable N (in this case, the variable N is changed to 2), and is finished.

Figure 10:
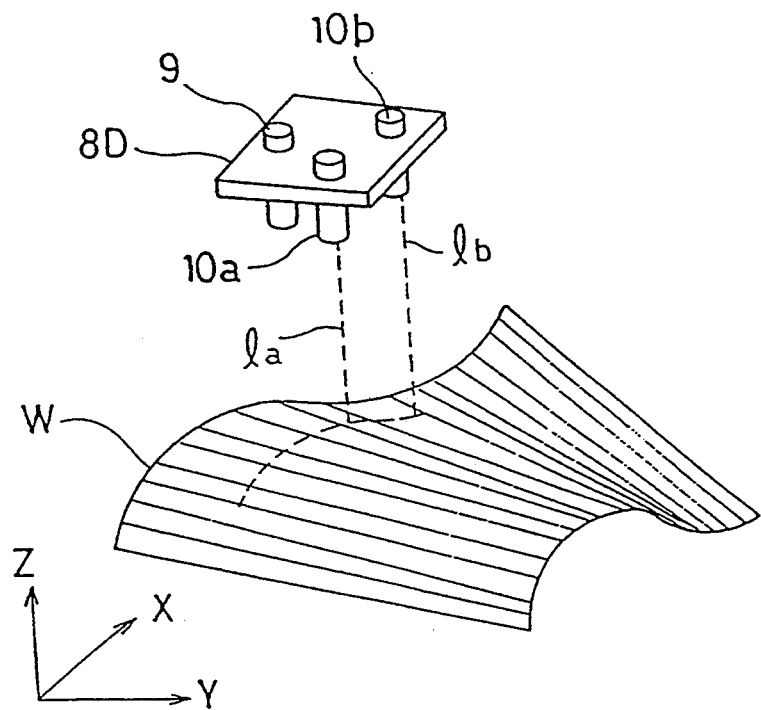

When the timer interrupting program as shown in FIG. 8 is completed, the process returns to a step S35 as shown in FIG. 7, and the completion of one scanning operation in the X-axial direction is ascertained by judging as to whether the variable N is equal to a value of (max+1). At this time, N is equal to 2, and thus the step S35 is repeated. During the repetitive execution of the step S35, the timer interrupting program as shown in FIG. 8 is intermittently executed at a predetermined time interval, and the bracket 8D coupled to the ultrasonic probes 9, 10a and 10b is displaced in the X-axial direction as shown in FIG. 10. In association with the scanning operation in the X-axial direction, the position data (X, Y and Z) on the surface shape of the object W are stored in the storing area in the storing manner as described above.

The process goes from the step S35 to a step S36 when one X-directional scanning operation is completed and the variable N is equal to the value of (max+1), and outputs the scan-stopping instruction signal. In response to the output of the scan-stopping instruction signal, the timer interrupting program as shown in FIG. 8 goes to a step S348, and the last axis-position instructing values of $X_{max}$, $Y_{max}$, $Z_{max}$, $a_{max}$, $\beta_{max}$ for one scanning operation are accessed to perform the servo computing operation. The computed result is outputted to the servo amplifiers 13X to 13$\beta$.

Upon completion of one scanning operation in the X-axial direction as described above, the process goes to a step S37 as shown in FIG. 7 to judge as to whether the shape measuring operation is completed. In this embodiment, a preceding X-directional scanning line which precedes (away from) the current X-directional scanning line in the Y-axial direction by the distance L is scanned by the ultrasonic probes 10a and 10b to obtain the surface shape data thereof in parallel with the flaw detecting operation, and a control point for the preceding scanning line to which the ultrasonic probe 9 is positioned for the flaw detection is calculated on the basis of the surface shape data obtained by the ultrasonic probes 10a and 10b. Accordingly, in order to control the ultrasonic probe 9 for the flaw detection to be successively moved to plural control points on a scanning line in accordance with the position data which have been obtained through the shape measuring operation as described above, the scanning operation for the shape measurement is required to be repetitively carried out until the ultrasonic probe 9 reaches at least the first scanning line which has been subjected to the shape measurement by the ultrasonic probes 10a and 10b, that is, until the ultrasonic probe 9 is moved in the Y-axial direction by the distance L as shown in FIG. 3.

One scanning operation in the X-axial direction is insufficient for the movement of the ultrasonic probe 9 by the distance L, and thus the process returns from the step S37 to the step S31 to access the respective axis-position instructing values for a next scanning operation. This process circulating from the step S31 to S37 is repeated until the ultrasonic probe 9 is moved by the distance L.

Figure 11:
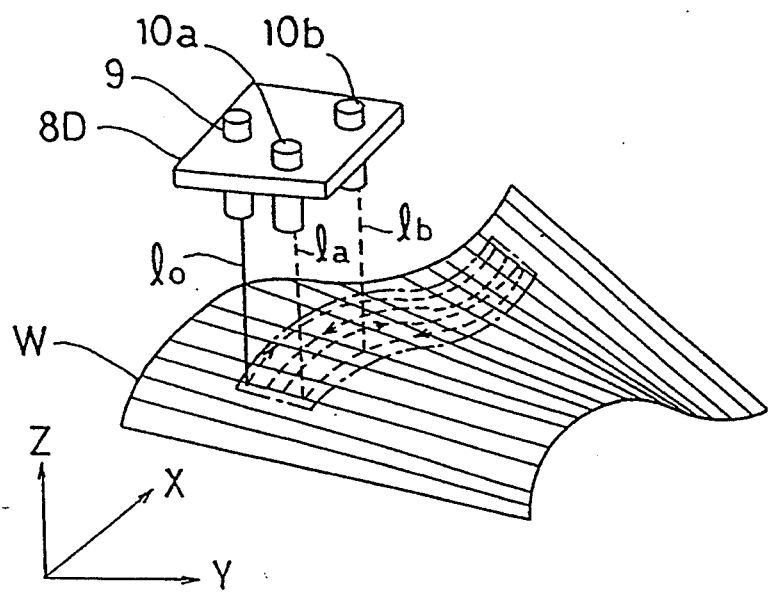

As shown in FIG. 11, the shape measuring operation is judged to be completed at the instantaneous time when the ultrasonic beam of the ultrasonic probe 9 reaches the flaw detection area whose surface shape data has been stored through the shape measuring operation as shown in FIG. 8, and the process goes from the step S37 as shown in FIG. 7 to a step S40 for the flaw detecting operation. As described above, during the shape measuring operation prior to the flaw detecting operation, the position data on the surface shape of the flaw detection area indicated by a one-dotted line of FIG. 11 is stored in the storing manner as shown in FIG. 9.

(3) Process of the flaw detecting operation

The flaw detecting operation at the step S40 of FIG. 5 will be described hereunder.

FIG. 12 is a detailed flowchart for the flaw detecting operation of the step S40, and is substantially similar to that of the shape measuring operation shown in FIG. 7. At a step S41, axis-position and axis-speed instructing values for the respective axes are first calculated. This calculation will be described in more detail with reference to FIGS. 13 and 14.

Figure 14:
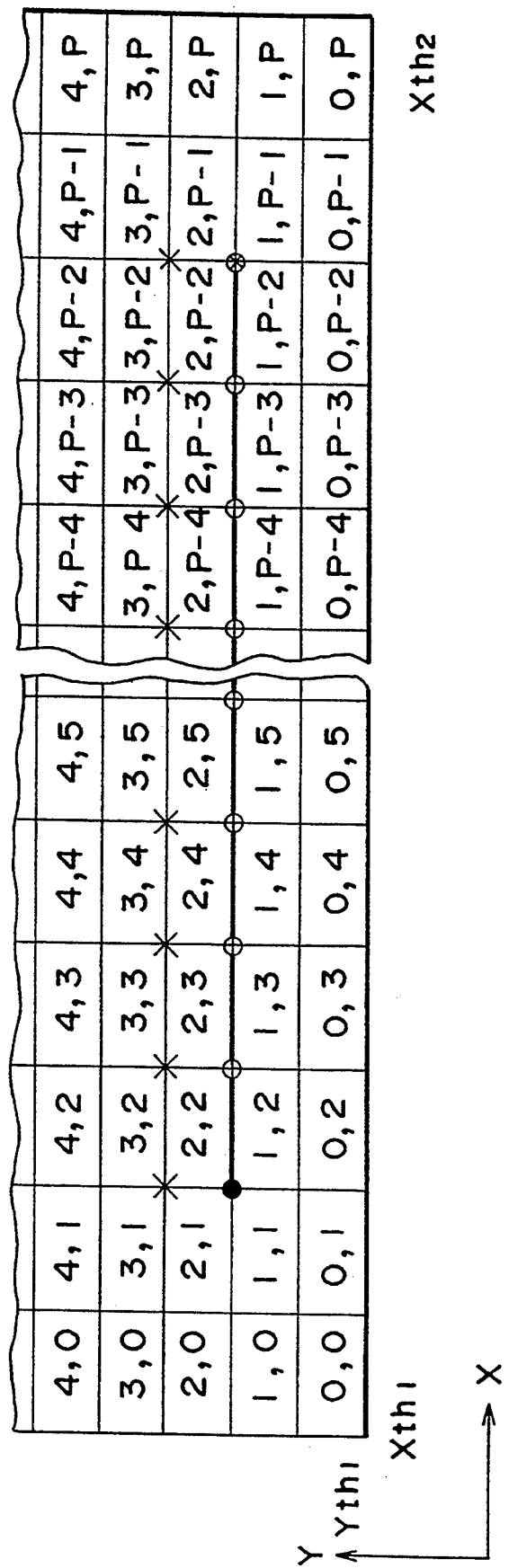

FIG. 13 is a flowchart for the calculation of the axis-position and speed instructing values for one scanning operation of the flaw detection at the step S41, and FIG. 14 is an explanatory diagram for a manner of selecting one of the position data on the surface shape of the target W in the calculation of the axis-position and axis-speed instructing values. A bold line as shown in FIG. 14 represents an X-axial scanning line, and the calculation of the axis-position and axis-speed instructing values for the control points which are represented by white and black circular marks (hereinafter referred to as "white and black circle") is carried out.

At a step S411 of FIG. 13, a normal vector at at a position which is near to the control point is calculated using the position data obtained through the shape measuring operation. For example, a first normal vector for a first control point represented by a black circle is calculated as follows.

If the normal vector for the first control point is calculated from position data in the storing sub-areas (1,1), (1,2), (2,2) and (2,1) which are neighboring to one another and at least one of which positionally includes the first control point of black circle (hereinafter referred to as "nearest sub-area"), a calculation error of the normal vector becomes larger when all the position data in the nearest sub-areas are in the neighborhood of the control point and these position data have errors. Therefore, it is not preferable to use the position data of the nearest sub-areas for the calculation of the normal vector. Accordingly, in place of the nearest sub-areas, other sub-areas (0,0), (0,3), (3,3) and (3,0) which are located at the outer side of the above sub-areas with respect to the control point (hereinafter referred to as "near sub-areas") are used for the calculation of the normal vector for the first control point. Representing the position data of the sub-areas (0,0), (0,3), (3,3) and (3,0) by (X1, Y1 and Z1), (X2, Y2 and Z2), (X3, Y3 and Z3) and (X4, Y4 and Z4), a normal vector N (Nx, Ny, Nz) of a position near to the first control point of black circle is calculated by the following equations.

$$Nx = \sum_{i=1}^{4} (Yi - Yj) \times (Zi + Zj) \quad (13)$$

$$Ny = \sum_{i=1}^{4} (Zi - Zj) \times (Xi + Xj) \quad (14)$$

$$Nz = \sum_{i=1}^{4} (Xi - Xj) \times (Yi + Yj) \quad (15)$$

Here, if i is not equal to 4, j=i+1, and if i is equal to 4, j=1.

Next, the position coordinate of a control point is calculated at a step S412. The position coordinate of the first control point of black circle is represented by (Xk, Yk, Zk), where the values of Xk and Yk are introduced for the mapping of the storing area and thus known values. Therefore, the position calculation of the step S412 is equivalent to calculation of the value of Zk.

Figure 15:
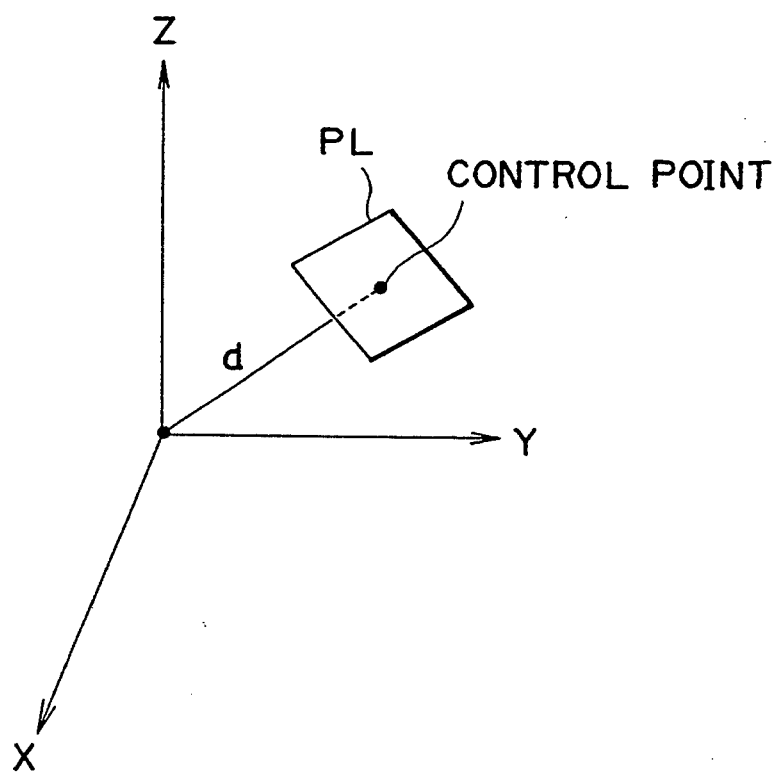

The following equation (16) represents a plane PL containing the position of a control point in a three-dimensional coordinate as shown in FIG. 15.

$$NxX + NyY + NzZ + d = 0 \quad (16)$$

Therefore, if the normal vector N (Nx, Ny, Nz) is calculated by the equations (13) to (15), the coefficient d of the above plane equation is calculated using the coordinate (Xm, Ym, Zm) of a position neighboring to the first control point of black circle as follows.

$$d = -(NxXm + NyYm + NzZm) \quad (17)$$

The value of Zk for the first control point of black circle is calculated using the coefficient d thus obtained as follows.

$$Zk = -(d + NxXk + NyYk)/Nz \quad (18)$$

The coordinate value (Xm, Ym, Zm) used for the above calculation of the coefficient d will be described hereunder.

As described above, the normal vector for the first control point is calculated using the position data of the near sub-areas (0,0), (0,3), (3,3), (3,0) as shown in FIG. 14. However, as a position data used for the calculation of the coefficient d should be used the position data of the nearest sub-areas in order to approach the calculated coefficient d to the true one. Therefore, the position data of the nearest sub-areas (1,1), (1,2), (2,2) and (2,1) are used for the calculation of the coefficient d. That is, substituting the position data of the nearest sub-area (1,1) and the normal vector obtained by the equations (13) to (15) in the equation (17), the coefficient d is calculated into d1. Similarly, the coefficients d2, d3 and d4 are obtained for the position data of the nearest sub-areas (1,2), (2,2) and (2, 1), respectively. Finally, an average of the values of d1, d2, d3 and d4 is calculated to obtain the coefficient d as follows.

$$d = (d1 + d2 + d3 + d4)/4 \quad (19)$$

This averaging operation of the coefficient d statistically enables the calculated coefficient d to be approached to the true one.

Through the above calculation, the normal vector N (Nx, Ny, Nz) and the position (Xk, Xk, Zk) for the first control point are obtained.

The process of the program as shown in FIG. 13 goes to step S413, and calculation and storage of axis-position instructing values for the respective axes every control point are carried out. Here, setting the axis-position instructing values to such values that the distance between the ultrasonic probe 9 and the surface of the target W is equal to $l_0$, the axis-position instructing values (Xr, Yr, Zr, $\alpha$r, $\beta$r) for the respective axes are determined by the following equations (20) to (24), and then stored.

$$Xr = f4(Xk, Yk, Zk, Nx, Ny, Nz, l_0) \quad (20)$$

$$Yr = f5(Xk, Yk, Zk, Nx, Ny, Nz, l_0) \quad (21)$$

$$Zr = f6(Xk, Yk, Zk, Nx, Ny, Nz, l_0) \quad (22)$$

$$\alpha r = f7(Nx, Ny, Nz) \quad (23)$$

$$\beta r = f8(Nx, Ny, Nz) \quad (24)$$

Next, the process of the program goes to a step S414 to judge as to whether the calculation of the axis-position instructing values for one scanning operation is completed. In this case, it is judged that the calculation for one scanning operation is not completed because the calculation for only the first control point of black circle is made at this time, and thus the program returns to the step S411 to calculate a normal vector for a position neighboring to a next control point of white circle and a position data therefor. The above steps S411 to S414 are successively repeated until the calculation for the control points from the black circle to an X-lettered white circle of FIG. 14 are completed, and then the process of the program goes to a step S415. The axis-position instructing values for the respective axes for one scanning operation comprise the following data groups.

$$Xr = (Xr_s, Xr_1, \ldots Xr_n, \ldots Xr_{max}) \quad (25)$$

$$Yr = (Yr_s, Yr_1, \ldots Yr_n, \ldots Yr_{max}) \quad (26)$$

$$Zr = (Zr_s, Zr_1, \ldots Zr_n, \ldots Zr_{max}) \quad (27)$$

$$\alpha r = (\alpha r_s, \alpha r_1, \ldots \alpha r_n, \ldots \alpha r_{max}) \quad (28)$$

$$\beta r = (\beta r_s, \beta r_1, \ldots \beta r_n, \ldots \beta r_{max}) \quad (29)$$

Here, the position instruction values for the respective axes ($Xr_s, Yr_s, Zr_s, \alpha r_s, \beta r_s$), ($Xr_1, Yr_1, Zr_1, \alpha r_1, \beta r_1$), ..., contains some errors due to a calculation error and so on. Thus, an averaging operation of the axis-position instructing values is carried out at a step S415. The averaging operation is carried out using the following equations (30) to (34), for example.

$$Xn = (Xr_{n-1} + Xr_n + Xr_{n+1})/3 \quad (30)$$

$$Yn = (Yr_{n-1} + Yr_n + Yr_{n+1})/3 \quad (31)$$

$$Zn = (Zr_{n-1} + Zr_n + Zr_{n+1})/3 \quad (32)$$

$$\alpha n = (\alpha r_{n-1} + \alpha r_n + \alpha r_{n+1})/3 \quad (33)$$

$$\beta n = (\beta r_{n-1} + \beta r_n + \beta r_{n+1})/3 \quad (34)$$

As is apparent from the above equations, the averaging operation of the axis-position instructing values is an operation of obtaining an arithmetical mean of any three axis-position instructing values including any one control point and two control points located before and behind the control point. No averaging operation is necessary to the starting and terminating control points.

The axis-position instructing values of all the control points are subjected to the calculation of the equations (30) to (34) to obtain data groups which are formally similar to data groups represented by the equations (2) to (6).

Figure 16:
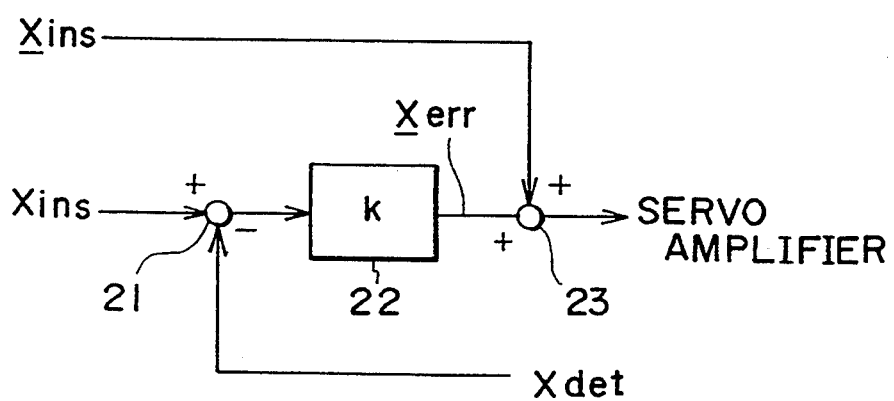

In the flaw detecting operation of this embodiment, position feedback control and speed feedforward control are adopted to improve the tracing accuracy of the ultrasonic probe 9. That is, as shown in FIG. 16, a signal Xins representing a axis-position instructing value and a signal Xdet representing a current position which is currently detected are input to a deviator 21 to obtain a difference (deviation) between the axis-position instructing value Xins and the current position Xdet. The deviation thus obtained is input to a coefficient multiplier 22 to be multiplied by a coefficient k and outputted as an axis-speed instructing value Xerr. Further, the axis-speed instructing value Xerr thus obtained and an axis-speed instructing value Xins are input to an adder 23 to calculate a sum thereof, and the sum result is outputted to the servo amplifiers 13A to 13$\beta$.

At a step S416 of FIG. 13, calculating and averaging operations of axis-speed instructing values for the speed feedforward control are carried out. The axis-speed instructing values are calculated by the following equations, for example.

$$\dot{X}rn = (Xr_{n+1} - Xr_n)/\Delta T \quad (35)$$

$$\dot{Y}rn = (Yr_{n+1} - Yr_n)/\Delta T \quad (36)$$

$$\dot{Z}rn = (Zr_{n+1} - Zr_n)/\Delta T \quad (37)$$

$$\dot{\alpha}rn = (\alpha r_{n+1} - \alpha r_n)/\Delta T \quad (38)$$

$$\dot{\beta}rn = (\beta r_{n+1} - \beta r_n)/\Delta T \quad (39)$$

Here, $\Delta T$ is a sampling time interval of the timer interrupting program. By calculating the axis-speed instructing values for all of the control points with the equations (35) to (39), the axis-speed instructing values for the respective axes for one scanning operation are obtained as data group represented by the following equations (40) to (44).

$$\dot{X}r = (\dot{X}r_s, \dot{X}r_1, \ldots \dot{X}r_n, \ldots \dot{X}r_{max}) \quad (40)$$

$$\dot{Y}r = (\dot{Y}r_s, \dot{Y}r_1, \ldots \dot{Y}r_n, \ldots \dot{Y}r_{max}) \quad (41)$$

$$\dot{Z}r = (\dot{Z}r_s, \dot{Z}r_1, \ldots \dot{Z}r_n, \ldots \dot{Z}r_{max}) \quad (42)$$

$$\dot{\alpha}r = (\dot{\alpha}r_s, \dot{\alpha}r_1, \ldots \dot{\alpha}r_n, \ldots \dot{\alpha}r_{max}) \quad (43)$$

$$\dot{\beta}r = (\dot{\beta}r_s, \dot{\beta}r_1, \ldots \dot{\beta}r_n, \ldots \dot{\beta}r_{max}) \quad (44)$$

Next, like the axis-position instructing values as described above, the axis-speed instructing values are also subjected to the averaging operation. The averaging operation of the axis-speed instructing values are carried out using the following equations (45) to (49).

$$\dot{X}n = (\dot{X}r_{n-1} + \dot{X}r_n + \dot{X}r_{n+1})/3 \quad (45)$$

$$\underline{Y}n=(\underline{Y}rm_{-1}+\underline{Y}rm+\underline{Y}rm_{+1})/3 \quad (46)$$

$$\underline{Z}n=(\underline{Z}rm_{-1}+\underline{Z}rm+\underline{Z}rm_{+1})/3 \quad (47)$$

$$\underline{\alpha}n=(\underline{\alpha}rm_{-1}+\underline{\alpha}rm+\underline{\alpha}rm_{+1})/3 \quad (48)$$

$$\underline{\beta}n=(\underline{\beta}rm_{-1}+\underline{\beta}rm+\underline{\beta}rm_{+1})/3 \quad (49)$$

This averaging operation of the axis-speed instructing value is an operation of obtaining an arithmetical mean of axis-speed instructing values of three control points including any one control point and two control points before and behind the control point. No averaging operation is necessary for the starting and terminating control points.

The axis-speed instructing values of all the control points which are obtained through the averaging operation of the equations (45) to (49) comprises data groups of the averaged axis-speed instruction values for the respective axes for one scanning operation which are represented by the following equations (50) to (54).

$$\underline{X}r=(\underline{X}r_s, \underline{X}r_1, \ldots \underline{X}r_n, \ldots \underline{X}r_{max}) \quad (50)$$

$$\underline{Y}r=(\underline{Y}r_s, \underline{Y}r_1, \ldots \underline{Y}r_n, \ldots \underline{Y}r_{max}) \quad (51)$$

$$\underline{Z}r=(\underline{Z}r_s, \underline{Z}r_1, \ldots \underline{Z}r_n, \ldots \underline{Z}r_{max}) \quad (52)$$

$$\underline{\alpha}r=(\underline{\alpha}r_s, \underline{\alpha}r_1, \ldots \underline{\alpha}r_n, \ldots \underline{\alpha}r_{max}) \quad (53)$$

$$\underline{\beta}r=(\underline{\beta}r_s, \underline{\beta}r_1, \ldots \underline{\beta}r_n, \ldots \underline{\beta}r_{max}) \quad (54)$$

The averaging operation of the axis-speed instructing values is carried out at a step S416 as shown in FIG. 13. Thereafter, the program as show in FIG. 13 is terminated, and the process goes to the step S42 as shown in FIG. 12.

The averaging operations of the steps S415 and 416 may be eliminated.

The processings of the steps S42 to the S45 are carried out using the data groups of averaged axis-position and axis-speed instructing values which are represented by the equations (40) to (44) and (50) to (54), respectively. Like the shape measuring operation, after the processings of the steps S42 and S43 are carried out and the scan-starting instruction signal is outputted at the step S44, a timer interrupting program as shown in FIG. 17 is executed.

Figure 18:
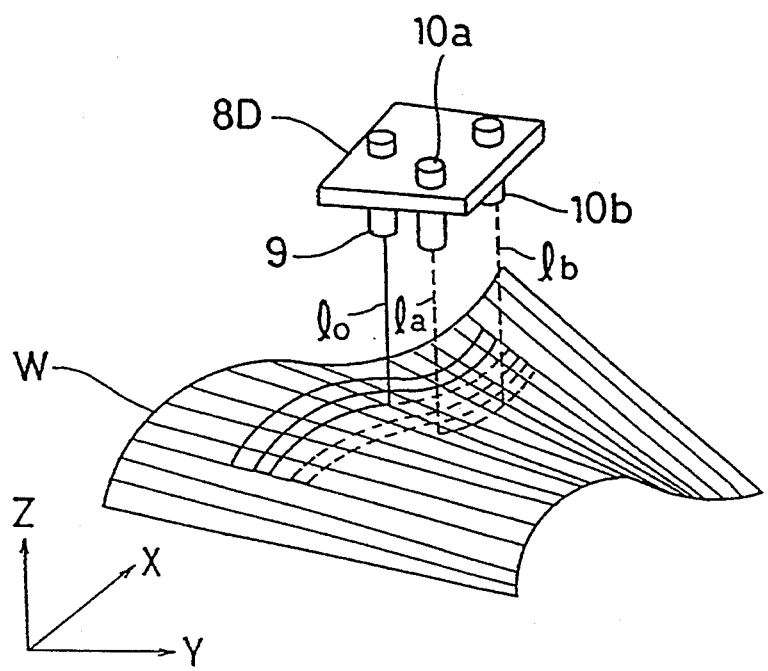

At a step S441 of FIG. 17, it is judged as to whether the scan-stopping instruction signal is outputted. If it is judged that the scan-stopping instruction signal is not outputted, then the access of the N-th axis-position instruction values for the respective axes and servo calculating and outputting operations are carried out at a step S442. These operations are carried out with the position feedback control and the speed feedforward control as shown in FIG. 16. Thereafter, the process goes to a step S443 at which an output of the ultrasonic probe 9 is inputted to the control device 12 and a flaw detection result is outputted as a flaw detection data of the control point (Xm, Ym) to the recording device 15. Next, steps S444 to S448 which are similar to the steps of S343 to 347 as shown in FIG. 8 are successively carried out, arid a preceding scanning line represented by a dotted line of FIG. 18 is subjected to the shape measuring operation in parallel with the flaw detecting operation as shown in FIG. 18.

The processes as described above are repeated until one scanning operation is completed, and then the process goes from the step S45 to the step S46 of FIG. 12 to output the scan-stopping instruction signal. When it is judged at the step S441 of FIG. 17 that the scan-stopping instruction signal is outputted, at a step S449 the access of the N-th axis-position instructing values for the respective axes, the servo calculation and the output of the servo-calculated result are carried out. Thereafter, the process goes to the step S47, and it is judged as to whether the flaw detecting operation is completed. That is, it is judged as to whether the area surrounded by the bold line of FIG. 9 is wholly scanned. If it is judged that the area is not wholly scanned, the process returns to the step S41 to calculate the respective axis-position instructing values for next one scanning operation, for example, on a scanning line which is marked by X-letters as shown in FIG. 14.

If the flaw detection area as shown in FIG. 9 is judged to be wholly scanned, the process goes from the step S47 to the step S50 as shown in FIG. 5 to position the respective axes at predetermined positions, and the control operation is completed.

In summary, the surface shape measuring and flaw detecting operations of the target W in the embodiment as described above with reference to FIGS. 1 to 18 are carried out as follows.

(a) The position and orientation of the distance sensor units are controlled on the basis of the data on the surface shape of the target which is beforehand obtained, and then an ultrasonic signal for the distance measurement is radiated to the target. Thereafter, the ultrasonic signal reflected from the target is detected to calculate a distance between a distance measuring point and the distance sensor unit on the basis of the detected ultrasonic signal. From the distance data thus obtained and the current position of the distance sensor unit, a surface shape information at the measuring point on the target, that is, the surface shape data is obtained.

(b) The surface shape data is stored for any one of storing sub-areas into which a storing area assigned to the flaw detection area is segmented in the X-Y plane. In this embodiment, only one data is stored for each storing sub-area.

(c) The processes of (a) and (b) are repeated until the distance sensor unit is moved by a distance L.

(d) Temporary axis-position instructing values (data on position and orientation of the probe 9) for each control point are calculated from the surface shape data which are stored in the storing sub-areas through the processes (a), (b) and (c), and then plural axis-position instructing values thus calculated are averaged to obtain a final axis-position instructing value for each control point.

(e) An axis-speed instruction value for the control point is calculated from the averaged axis-position instructing values, and then an averaged axis-speed instructing value for any control point is calculated from the axis-speed instructing values of plural control points.

(f) A deviation between the average axis-position instructing value and a current position is obtained to calculate an axis-speed instructing value for the deviation. The axis-speed instructing value for the deviation and the averaged axis-speed instructing value are summed, and a sum result is outputted. The respective axis-driving members are controlled with the sum result to control the position and orientation of the ultrasonic probe 9 for the flaw detection, whereby an ultrasonic signal for the flaw detection is directed in the normal direction to the surface of the target W and the ultrasonic probe 9 is positionally kept away from the surface of the target by a predetermined distance.

(g) The ultrasonic signal is transmitted from the ultrasonic probe 9 to the surface of the target while the ultrasonic probe 9 is kept in predetermined positional and orientational relationship, thereby performing the flaw detecting operation. The ultrasonic signal reflected from the surface of the target W is received by the flaw detecting ultrasonic probe 9 and is subjected to a well-known processing. Thereafter, the processed data as well as the position data of the control points are recorded in the recording device 15.

(h) In parallel with the flaw detecting operation, an ultrasonic signal is transmitted from the distance sensor unit to the surface of the target to obtain a surface shape data of a preceding scanning line which precedes to a current scanning line for the flaw detection by the distance L. This surface shape data is used to control the position and orientation of the flaw-detecting ultrasonic probe 9 on the preceding scanning line or a scanning line neighboring thereto.

According to the embodiment as described above, the shape-measuring and flaw-detecting ultrasonic probes for the distance measurement and flaw detection are integrally controlled in position and orientation, and thus the distance measurement can be surely made in parallel with the flaw detection. As a result, the calculation and control for the orientation to the normal direction can be more accurately performed, and thus a flaw detection accuracy is wholly improved.

Further, since the shape measurement can be made simultaneously with the flaw detection, the flaw detection for the target having a curved surface can be performed in one scanning operation. As a result, a time required for the whole flaw detection is shortened.

Still further, the axis-position instructing values for the position feedback control and the axis-speed instructing values for the speed feedforward control are reduced in error, and an ultrasonic beam of the ultrasonic probe 9 is accurately directed to a normal direction of the surface of the target W at each control point, so that the flaw detection can be performed with high accuracy. In addition, a time required for movement or displacement of the ultrasonic probe to each control point is shortened and a tracing accuracy is also improved.

Still further, a position storing area assigned to a flaw detection area is divided into sub-areas in the X-Y plane, and only one position data is stored in each sub-area. A control point for flaw detection on any scanning line is calculated from the position data of each sub-area. Therefore, this embodiment has the following advantages.

(a) Reduction of a memory capacity is possible.

(b) Any scanning line different from a scanning line which is subjected to the shape measurement may be freely subjected to the flaw detection. As a result, a degree of freedom in the flaw detecting operation is broadened and the arrangement of the flaw-detecting probe and the distance-measuring probe is not restricted.

Still further, according to this embodiment, the surface of the target W is imaginarily divided into plural flaw-detection areas in the X-Y plane, and the surface position data of each of the areas is stored in a storing area which is assigned to the flaw-detection area. Therefore, even when the position data of a flaw detection area can not be obtained due to presence of a flaw on the surface of the area, the position data of the area can be interpolatively calculated from position data of areas surrounding the area. Accordingly, the flaw detection (distance measurement) is not influenced by the flaw itself.

In the calculation of a normal vector at the Step S411 of FIG. 13, the normal vector is calculated on the basis of four position data of the storing sub-areas which include control points of black or white circle. However, the normal vector may be calculated from position data of three areas, or five or more areas insofar as they include the control points of white or black circle.

In the embodiment as described above, the ultrasonic probe 9 is oriented or directed to the normal direction at all control points for the flaw detection. However, the ultrasonic probe 9 may be directed to a direction inclined to the normal direction at an angle, for example, to a direction of the critical angle for a surface wave.

Figure 19:
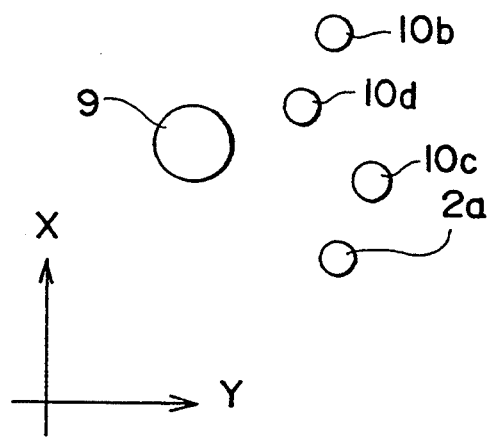
FIG. 19 shows another arrangement of the ultrasonic probe for the flaw detection and the probe for the distance measurement.

Further, in the embodiment as described above, two ultrasonic probes 10a and 10b are used to perform a distance measuring operation of the surface of the target W. However, two or more ultrasonic probes 10a, 10b, 10c and 10d in an arrangement as shown in FIG. 19 may be used. In this case, the same calculation as represented by the equations (7) to (9) are merely added for an added ultrasonic probe.

Figure 20:
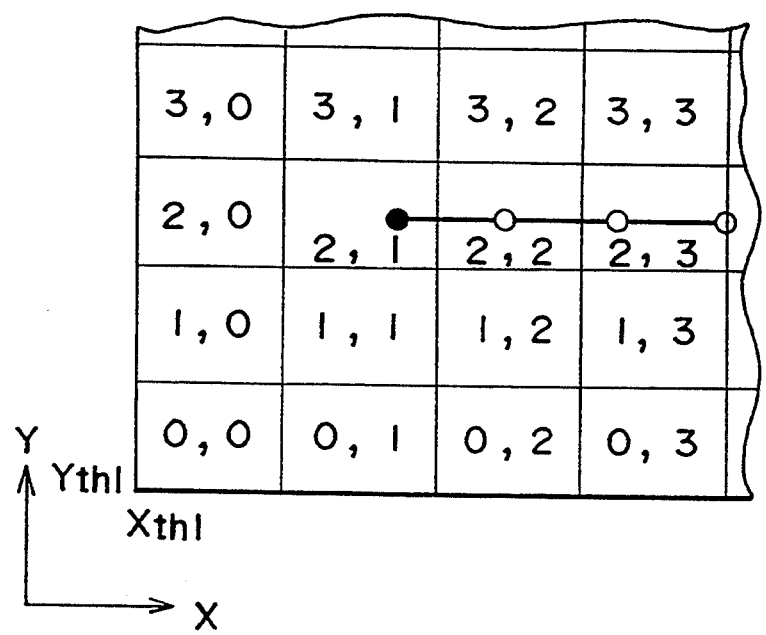
FIG. 20 is an explanatory diagram for a scanning line for the flaw detection within a sub-area whose shape information is stored.

In FIG. 14, the control points are illustratively located at boundaries between neighboring storing sub-areas. However, as shown in FIG. 20, the control points may be located within the storing sub-areas. In this case, the position calculation of the control point is carried out using a position data of only a storing-area in which the control point is located. For example, the position calculation for a control point of black circle as shown in FIG. 20 is carried out using a position data of a storing sub-area (2,1).

According to the above embodiment, since at least two ultrasonic probes 10a and 10b are used for the position measurement of the surface of the target, even when the ultrasonic probe 9 scans a scanning line indicated by the bold line of FIG. 14, those areas which are located outside of the flaw detection area, for example, areas having columns of 0, 1, P−1 and P, can be subjected to the distance measuring (surface shape detecting) operation.

Second Embodiment

FIGS. 21A, 21B and 22 show a second embodiment of this invention. In more detail, FIGS. 21A and 21B are front and side views of a robot handling member, and FIG. 22 is an explanatory diagram for a manner of selecting some of stored position data on the surface shape of the target for the calculation of the respective axis-position instruction values and corresponds to FIG. 14.

In the second embodiment, one ultrasonic probe is used for the surface position measurement of the target and the remain has the same construction as that of the first embodiment.

The use of one ultrasonic probe for the surface shape measurement would cause a problem in the calculation of the axis-position instructing values of the respective axes at the step S41 of FIG. 12. As described in the first embodiment, the use of two ultrasonic probes (10a and 10b) for the surface shape measurement enables the surface shape (or distance) measurement for the areas ( having the columns of 0, 1, P−1 and P) which are outside of the flaw detection area located from the control point of black circle to the control point of the X-lettered white circle. However, if only one ultrasonic probe is used for the surface shape measurement and the ultrasonic probe is moved from the position Xth1 to the position Xth2 for the flaw detection as shown in FIG. 22, the position data of those areas (outside areas) which are outside of the areas located between control points B and E represented by a double circle are not obtained, and thus the axis-position instructing values for the control points represented by the double circle can not be calculated using the same calculating operation as described above. In order to overcome the above problem, the following calculating operation is adopted to obtain the axis-position instructing values for the control points represented by the double circle.

First, a normal vector N(Nx, Ny, Nz) of a position neighboring to the control point of black circle of FIG. 22 is calculated from position data of areas (0,0), (0,3), (3,3) and (3,0) in the same calculating manner as represented by the equations (13) to (15). Thereafter, the following calculating operation is carried out on the assumption that the normal vectors for the control points A and B are identical to the normal vector for the control point of black circle.

For the control point A, the position data of the sub-area (1,0) and the normal vector N(Nx,Ny,Nz) of a position neighboring to the control point of black circle are substituted in the equation (17) to obtain a value of d1. Similarly, d2 for the sub-area (1,1), d3 for the sub-area (2,1) and d4 for the sub-area (2,2) are obtained, and a coefficient d is calculated from these values of d1, d2 d3 and d4 by the equation (19).

Next, the coefficient d, the normal vector N (Nx,Ny,Nz) of the position neighboring to the control point of black circle, and the position (Xk, Yk) of the control point A are substituted in the equation (18) to obtain a value of Zk for the control point A.

On the other hand, for the control point B, the calculation of the coefficient d is carried out using the position data of each of the sub-areas (1,0) and (2,0) twice in the same calculating manner as described above. That is, two sub-areas located at the left side of the control point in FIG. 22 are imaginarily regarded as the sub-areas (1,0) and (2,0) and thus the position data of the sub-areas (1,0) and (2,0) are doubly used to obtain the coefficient d. This calculating operation is called as "extrapolative calculation".

The above calculation is carried out for the control points D and E on the assumption that normal vectors for these control points are identical to a normal vector for the control point C.

According to the second embodiment, only one ultrasonic probe is sufficient to perform the surface shape measurement of the object, and thus the apparatus is wholly lower in price.

Third Embodiment

Figure 25:
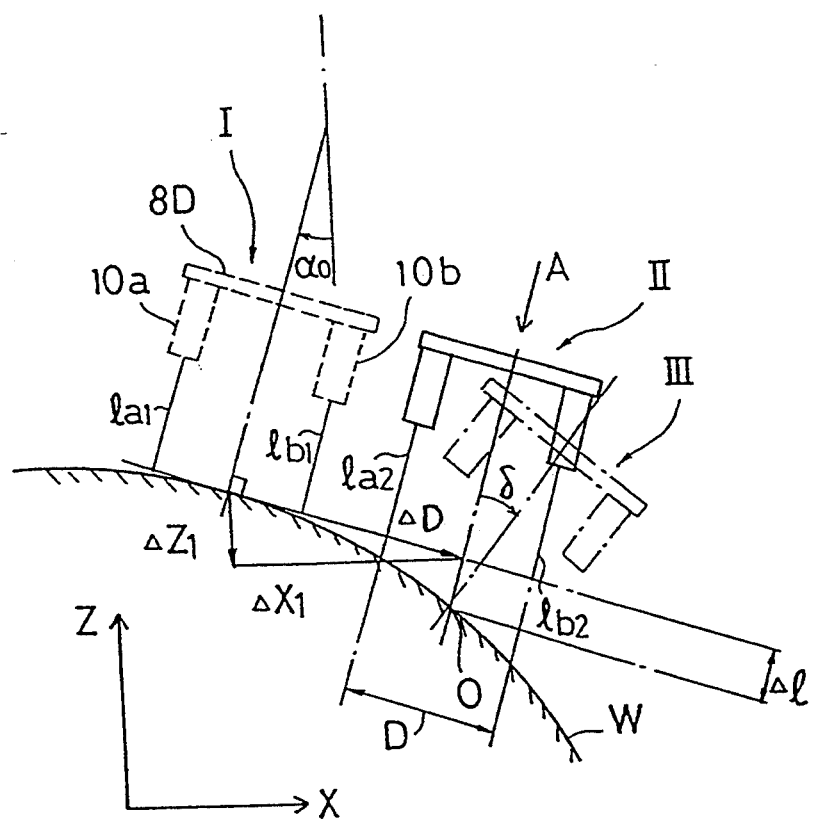

FIGS. 23 to 25 show a third embodiment of this invention. In the first embodiment, the respective axis-position instructing values which are used in the shape measuring operation are beforehand known for all positions. However, in the third embodiment, the respective axis-position instructing values are known for only the control-starting position. Accordingly, the third embodiment carries out the shape measuring operation while simultaneously detecting the surface shape of the target W on real time. The third embodiment has the same construction as the first embodiment as shown in FIGS. 1 to 4, except for a control operation of the control device A flowchart of FIG. 23 corresponds to the flowchart for the shape measuring operation of the first embodiment as shown in FIG. 7, and a flowchart of FIG. 24 corresponds to the timer interrupting program as shown in FIG. 8. FIG. 25 shows a positional relationship of the ultrasonic probes 10a and 10b for explaining an operation of the third embodiment.

The operation of the third embodiment will be described with reference to FIGS. 23 to 25.

In FIG. 23, after the ultrasonic probes 10a and 10b are positioned to the scan-starting positions at a step S31A, the scan-starting instruction signal is outputted at the step S34 to set up the timer interrupting program, and the surface position which is calculated in the same manner as described above at the steps S341 to 346 is stored. The above operations are similar to those of the first embodiment.

A calculation of the respective axis-position instructing values in this embodiment will be next described.

Assuming that the variation of a normal to the surface of the target is slight in the Y-axial direction vertical to the scanning direction (X-axial direction), it is sufficient to control only the three axes of X-, Z- and $\alpha$-axes. If the variation of a normal is assumed to be slight in the X-axial direction, the scanning direction may be the Y-axial direction.

A positional relationship (I) of FIG. 25 corresponds to a state where the positioning of the ultrasonic probes 10a and 10b to the scan-starting position is completed. In this case, it is assumed that the distances $1a_1$ and $1b_1$ between the surface of the target W and each of the ultrasonic probes 10a and 10b are equal to each other, and the following equation is satisfied.

$$1r = (1a_1 + 1b_1)/2 \tag{55}$$

Here, $1r$ is a mean of $1a_1$ and $1b_1$, and represents a control instructing value serving as a destination value of the distance between the surface of the target W and the ultrasonic probes 10a and 10b. Therefore, in the positional relationship (I), the center line of the bracket 8D is accurately directed to a normal direction to the surface of the target W, and the distance between each of the ultrasonic probes 10a and 10b and the surface of the target W is accurately equal to the control instructing value.

Next, an angle $\delta$ is calculated at a step S1347, where the angle $\delta$ represents an angular deviation between the center line of the bracket 8D and the normal direction to the surface of the target. The angle $\delta$ is equal to zero in the position relationship (I). Thereafter, an axis-position instructing value for the a-axis is calculated at a step S1348. Representing the axis-position instructing value for the $\alpha$-axis and a current position of the $\alpha$-axis by $\alpha r$ and $\alpha_0$, the following equation is satisfied because the angle $\delta$ is equal to zero in the positional relationship (I).

$$\alpha r = \alpha_0 \tag{56}$$

Next, axis-position instructing values for the X- and Z-axes are calculated at a step S1349. Here, representing a moving distance of the bracket 8D in one operation of the timer interrupting program by $\Delta D$ and assuming a moving direction of the bracket 8D to be parallel to the direction of a tangent of the surface of the target W, the axis-position instructing values for the X- and Z-axes are represented by the following equation as shown in FIG. 25.

$$Xr = X_0 + \Delta X_1 \quad (57)$$
$$= X_0 + \Delta D \cos\alpha r$$

$$Zr = Z_0 + \Delta Z_1 \quad (58)$$
$$= Z_0 + \Delta D \sin\alpha r$$

Next, the servo calculation and outputting operations are carried out using the respective axis-position instructing values which are obtained by the equations (56) to (58) and the current position of the ultrasonic probes $10a$ and $10b$, and then the timer interrupting program as shown in FIG. 24 is completed.

Upon completion of the timer interrupting program as shown in FIG. 24, the process returns to the step S35 as shown in FIG. 23 to judge as to whether one scanning operation is completed. This judgment is made by judging as to whether the value of Xa or Xb obtained using the equation (7) or (10) is larger than the value of Xth2. On the other hand, for the scanning operation in an opposite direction, this judgment is made by judging as to whether the value of Xa or Xb is smaller than the value of Xth1. At this time, the values of Xa and Xb are equal to or smaller than Xth2, and thus the step S35 is repetitively carried out.

When the process goes to the timer interrupting program again, the surface position data of the target W is stored at the steps S341 to S346. If, at this time, the positional relationship of the bracket 8D corresponds to a state (II) of FIG. 25, the angle δ is represented by the following equation (59).

$$\delta = \tan^{-1}((1b_2 - 1a_2)/D) \quad (59)$$

Here, D represents a distance between the ultrasonic probes $10a$ and $10b$. Therefore, the axis-position instructing value $\alpha r$ for the α-axis is obtained by the following equation (60).

$$\alpha r = \alpha_0 + \delta \quad (60)$$

Next, the axis-position instructing values Xr and Zr for the X- and Z-axes are obtained. In this case, the values of $\alpha r$ is varied and the deviation 1r is not equal to a value of $(1a_2 + 1b_2)/2$, and thus correction values for the X- and Z-axes are required.

First, in order to equalize the distance 1r to the value of $(1a_2 + 1b_2)/2$, the X-axis and Z-axis are first moved in a direction as indicated by an arrow A of FIG. 25. The correction values for the X- and Z-axes in this moving operation are represented by $\Delta X_2$ and $\Delta Z_2$. Next, the bracket 8D are rotated by the angle δ with a point 0 at the rotational center. As a result, the ultrasonic probes $10a$ and $10b$ has a positional relationship (III) of FIG. 25. Representing the correction values for the X- and Z-axes in this rotating operation by $\Delta X_3$ and $\Delta Z_3$, the axis-position instruction values of the X- and Z-axes are represented by the following equations (61) and (62).

$$Xr = X_0 + \Delta X_1 + \Delta X_2 + \Delta X_3 \quad (61)$$

$$Zr = Z_0 + \Delta Z_1 + \Delta Z_2 + \Delta Z_3 \quad (62)$$

Thereafter, the step S1347 is executed and the timer interrupting program is completed. The other processes of this embodiment are identical to those of the first embodiment.

In the above description, the two ultrasonic probes for the distance measurement are arranged in the scanning direction on the assumption that the variation of the normal is slight in the direction vertical to the scanning direction. However, it is possible that another ultrasonic probe for the distance measurement is newly disposed in the direction vertical to the scanning direction, and the bracket 8D is controlled on the basis of output signals of these three ultrasonic probes to be directed to a normal on the surface of the target along the direction vertical to the scanning direction.

According to the third embodiment, since it is not required to beforehand calculate the axis-position instructing values for the respective axes for the shape measuring operation prior to the flaw detecting and shape measuring operations, this embodiment can be easily applied a target to which no design specification data is obtained.

Fourth Embodiment

FIGS. 26A to 38 show a fourth embodiment of the flaw detector in which a cylindrical object is subjected to the flaw detection.

Figure 26A:
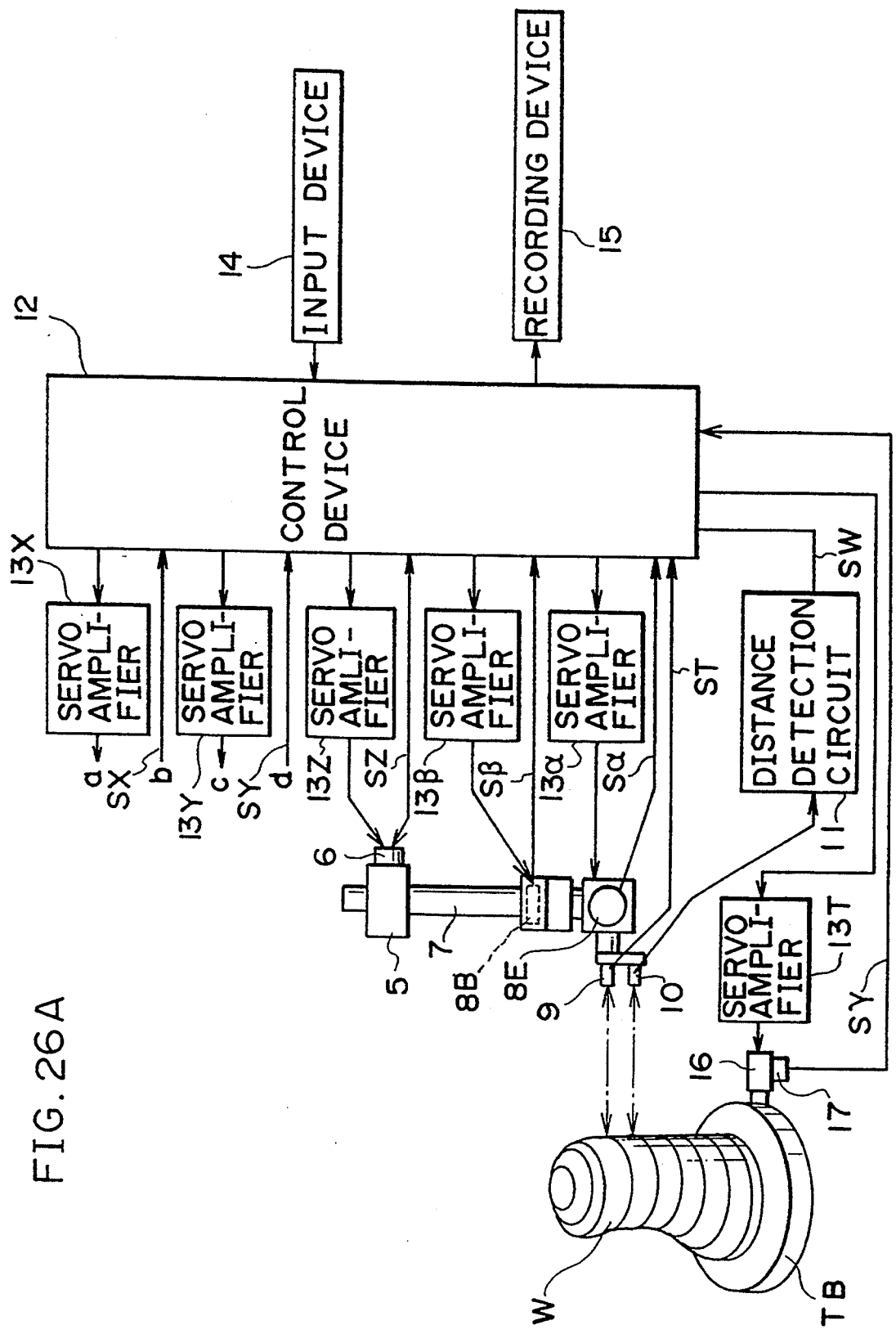
Figure 26B:
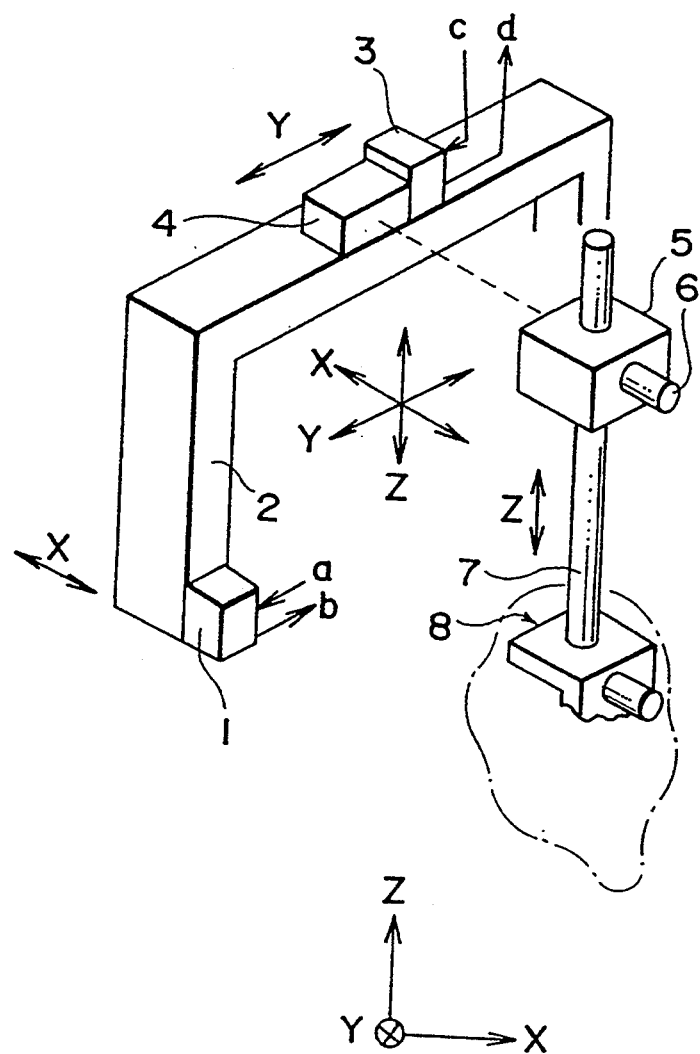

FIGS. 26A and 26B show the whole construction of the fourth embodiment, and the same elements as those of the first embodiment are represented by the same reference numerals. As shown in FIG. 26A, a massive cylindrical target W is mounted on a turn table TB which is rotatable around the central axis thereof which corresponds to the Z-axis, and an ultrasonic probe 10 for the distance measurement and an ultrasonic probe 9 for the flaw detection are secured to the robot handling member 8 so as to confront the peripheral surface of the target W.

Figure 27A:
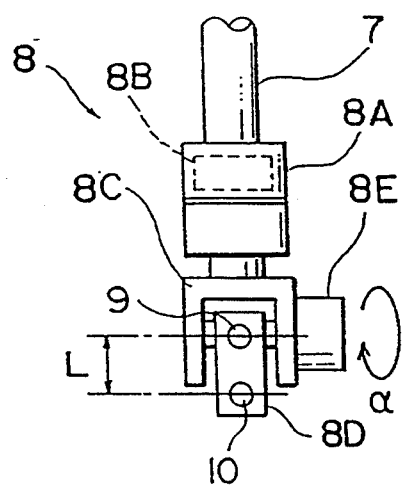
FIGS. 27A and 27B show a fabric of a sensor unit including an ultrasonic probe for the flaw detection and a probe for the distance measurement.
Figure 27B:
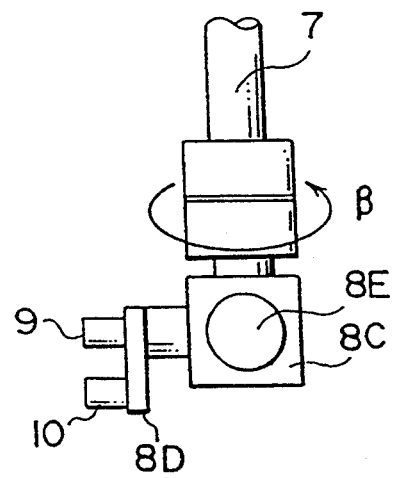

As shown in FIGS. 27A and 27B, the handling member 8 includes a driving member 8B having a rotational shaft for performing a rotational motion of the ultrasonic probe 9 and the distance sensor unit 10 in the β-axis, which is installed in a housing 8A fixedly secured to the lower end of the Z-axis arm 7, a bracket 8C secured to the rotational shaft of the β-axis driving member 8B, a driving member 8E having a rotational shaft for performing a rotational motion of the ultrasonic probe 9 and the distance sensor unit 10 in the α-axis which is secured to the bracket 8C, and a bracket 8D secured to the rotational shaft of the α-axis driving member 8E to which one ultrasonic probe for the flaw detection of the target W and one distance sensor unit 10 for the surface position measurement of the target W are secured in such a positional relationship that the ultrasonic probe 9 and the distance sensor unit 10 are spaced at a distance L in the Z-axial direction.

In FIG. 26A, a reference numeral 16 represents a driving member for rotating the turn table TB, and the driving member 16 controls a rotational angle of the turn table TB on the basis of an instruction signal from the control device 12. A reference numeral 17 represents a angle detector which is internally contained in the driving member 16, and an angle signal Sγ representing the detection result is input to the control device 12.

Calculation Processing in the Control Device 12

Figure 28:
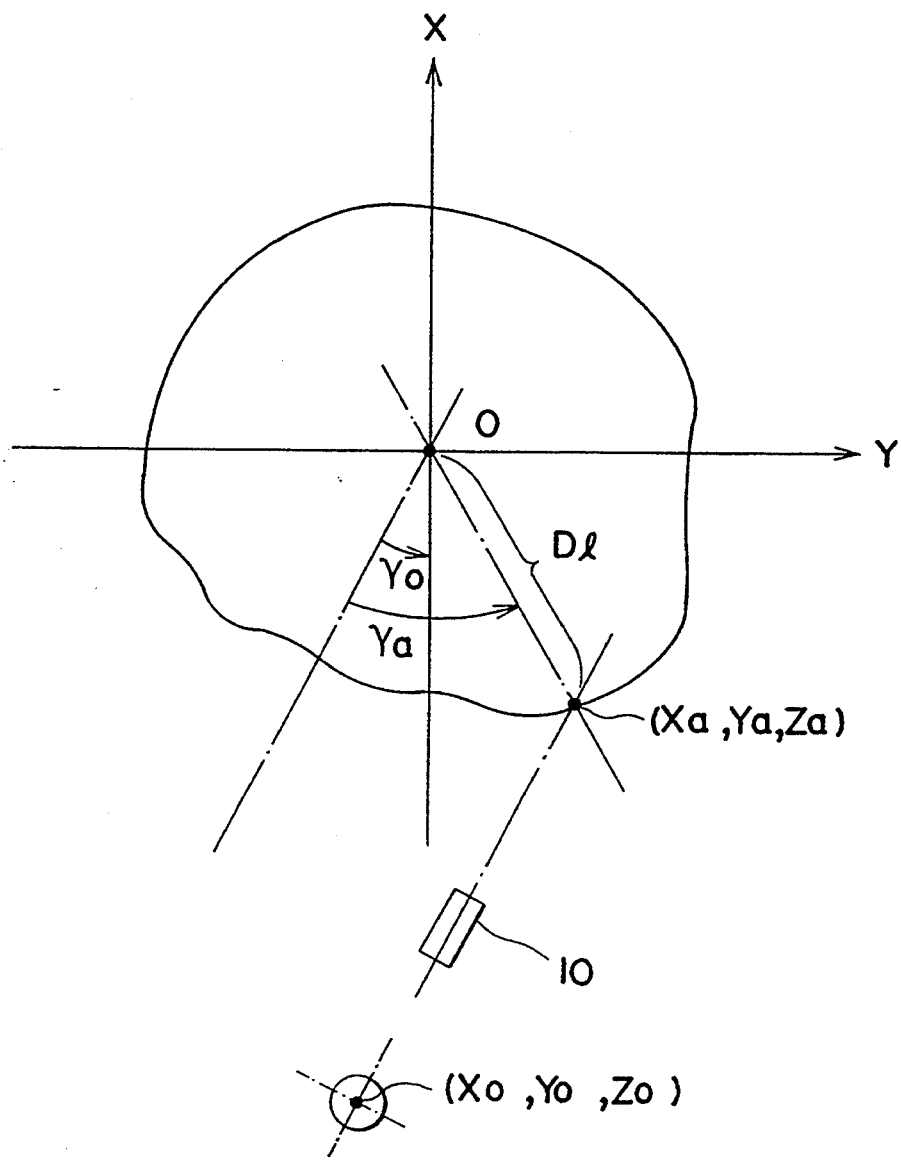

In this embodiment, the center position of the turn table TB is set to the origin 0 of the X-Y coordinate as shown in FIG. 28, and $\gamma_0$, $\gamma_a$ and $D_l$ are defined as shown in FIG. 28. That is, the $\gamma_0$ represents an intersection angle between the X-axial direction and a detecting direction of the distance sensor unit 10 at any time, the $\gamma_a$ represents an intersection angle between the detecting direction of the distance sensor unit 10 and a line connecting the origin 0 to a measuring point on the surface of the target onto which an ultrasonic signal is radiated from the distance sensor unit 10, and the $D_l$ represents a distance between the measuring point (Xa, Ya, Za) and the origin 0.

(1) Main Flowchart

The main flowchart of the calculation processing which is executed in the control device 12 is the same as that of FIG. 5.

Figure 29:
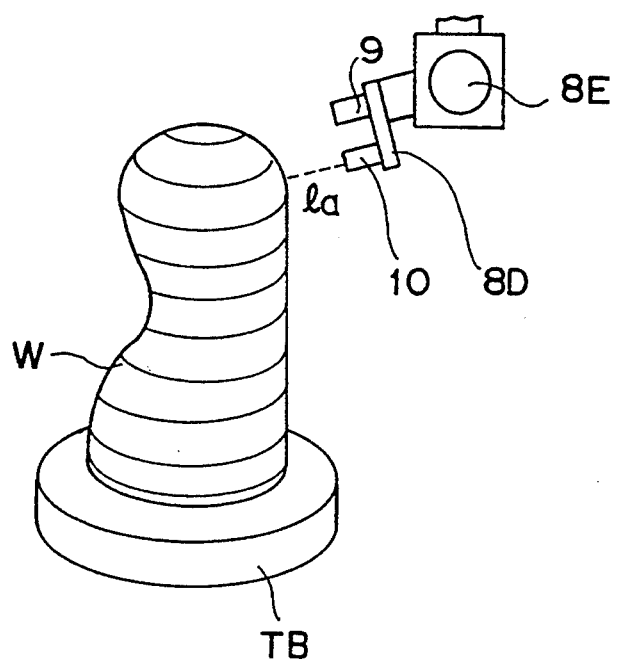
Figure 30:
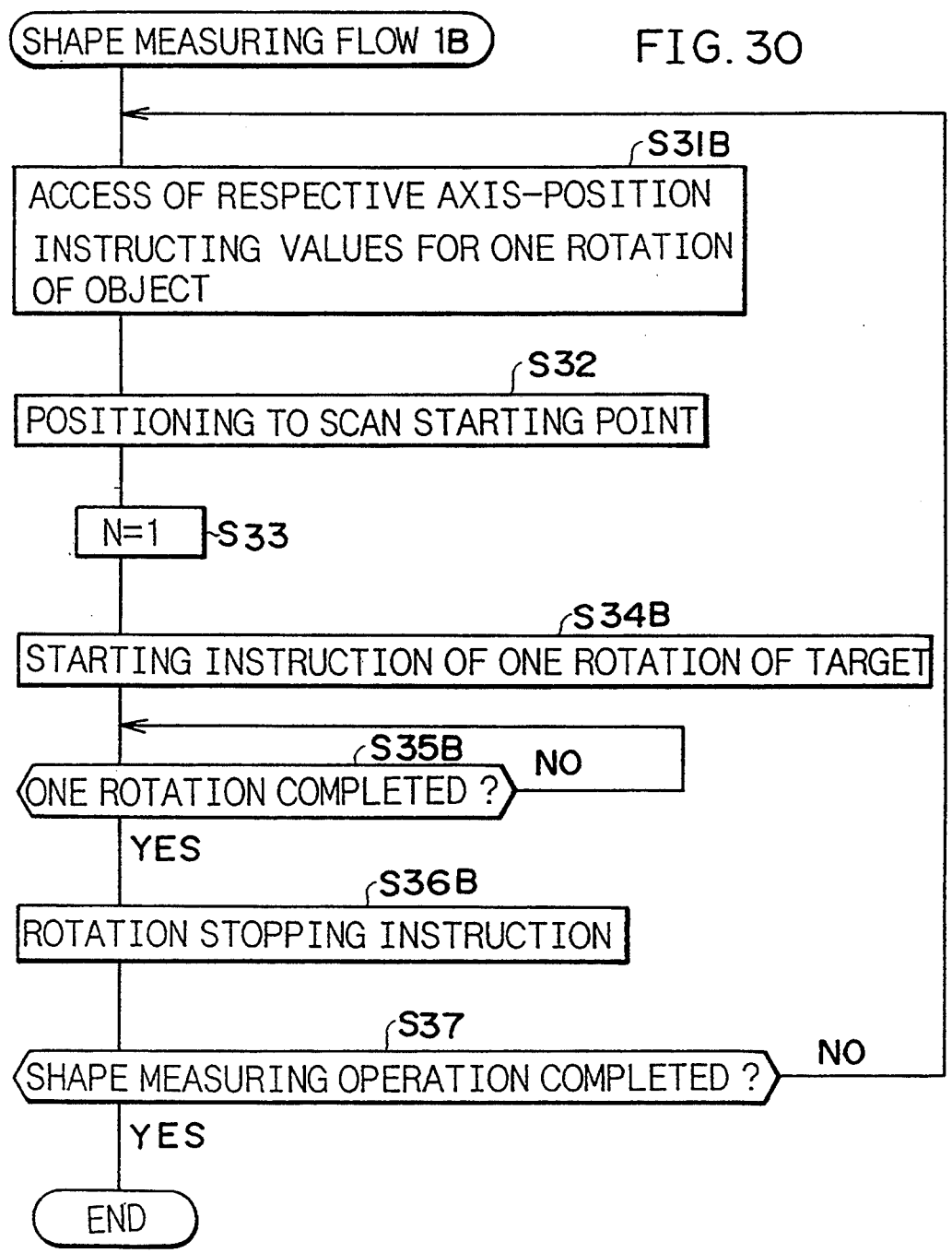

The memory and other elements are first initialized at the step S10, and then the ultrasonic probe 10 is positioned to the control-starting position at the step FIG. 29 shows a positional relationship when the above positioning operation is just completed. The process goes to the shape measuring operation at the step S30 to rotate the turn table TB while the ultrasonic probe 10 is controlled to be oriented (directed) to a normal direction to the surface of the target W at the measuring point on the basis of a surface shape data of the target W which is beforehand known from the design specification or the like, thereby performing a rotational scanning operation of the target W. This rotational scanning operation is repetitively carried out several times while displaced in the Z-axial direction by a predetermined pitch for a period between the successive rotational scanning operations. This repetitive rotational scanning operation is continued until an area having a distance L as shown in FIG. 27A is wholly subjected to the shape measuring operation to obtain more detailed surface shape data than the design specification data on the area before subjected to the flaw detecting operation. The surface shape of the target W is calculated every scanning line on the basis of the signals SX, SY, SZ, S$\alpha$, and S$\beta$ from the internal position and angle detectors of the respective axis-driving members and the signal SW from the ultrasonic probe 10. FIG. 30 is a detailed flowchart for the calculation of the surface shape.

Upon completion of the shape measuring operation as described above, the process goes to the step S40 to carry out the flaw detecting operation.

At the step S40, position data of control points which are used to confront the ultrasonic probe 9 to a point on the target W to be subjected to the flaw detection (hereinafter referred to as "flaw detection point") are calculated on the basis of the surface shape data of the target W which is obtained at the step S30, and an ultrasonic flaw-detection signal is input from the ultrasonic probe 9 to the control device 12 at a timing which is controlled or adjusted every control point.

Figure 35:
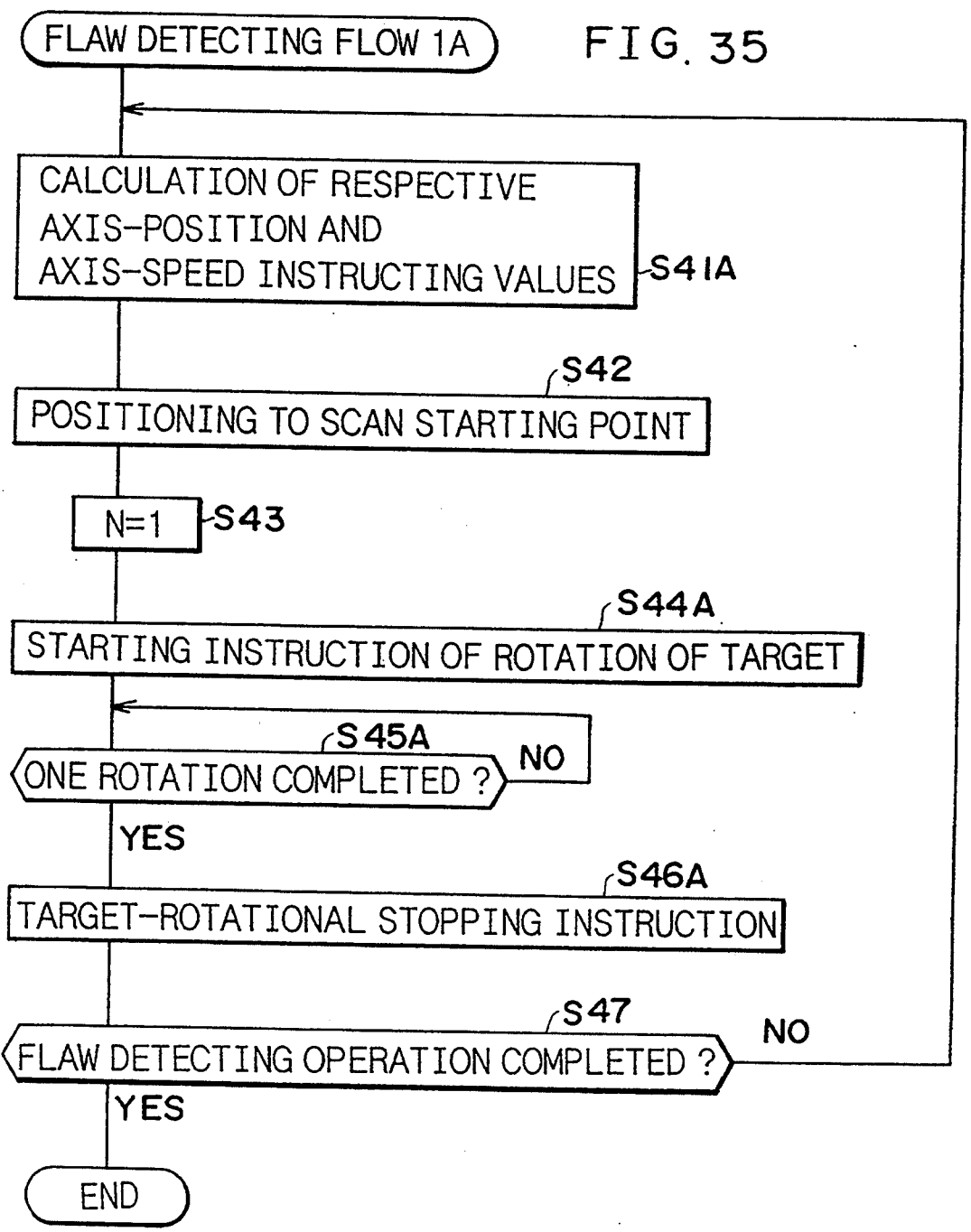

During the flaw detecting operation, a distance between the surface of the target W and the ultrasonic probe 10 for a preceding scanning line is also calculated on the basis of the signal SW from the ultrasonic probe 10 which positionally precedes the ultrasonic probe 9 by several scanning lines (by the distance L as shown in FIG. 27A), and on the basis of the calculated distance and the position data from the position or angle detectors as described above, a surface shape data for the preceding scanning line is also obtained in parallel with the flaw detecting operation. When the ultrasonic probe 9 arrives on the preceding scanning line whose surface shape data has been already obtained in parallel with the flaw detecting operation, the position data of a control point for the ultrasonic probe 9 on the preceding scanning line is calculated on the basis of the surface shape data which has been already obtained, and the flaw detecting operation is carried out using the calculated position data. The detailed process of the flaw detecting operation is shown in FIG. 35. Upon completion of the flaw-detecting operation, the ultrasonic probe 9 is moved to a terminal position at a step S50 and all of the processes are finished.

Next, the surface shape measuring operation and the flaw detecting operation of this embodiment will be described in more detail.

(2) Process of the shape measuring operation

FIG. 30 is a detailed flowchart (flow 1B) for the shape measuring operation of the step S30 of FIG. 5.

At a step S31B, axis-position instructing values for the respective axis-driving members for one rotational scanning operation are accessed, and stored in a memory. Each axis-position instructing value for each axis-driving member for one rotational scanning operation is composed of a data group represented by each of the following equations (63) to (68) which correspond to the equations (2) to (6).

$$Xr=(Xs, X_1, \ldots, Xn, \ldots, Xmax) \quad (63)$$

$$Yr=(Ys, Y_1, \ldots, Yn, \ldots, Ymax) \quad (64)$$

$$Zr=(Zs, Z_1, \ldots, Zn, \ldots, Zmax) \quad (65)$$

$$\alpha r=(\alpha s, \alpha_1, \ldots, \alpha n, \ldots, \alpha max) \quad (66)$$

$$\beta r=(\beta s, \beta_1, \ldots, \beta n, \ldots, \beta max) \quad (67)$$

$$\gamma r=(\gamma s, \gamma_1, \ldots, \gamma n, \ldots, \gamma max) \quad (68)$$

Here, $\gamma r$ represents an angle instructing value of the turn table TB.

Next, at the step S32, each axis-driving member is controlled to be positioned to the corresponding scan-starting position by setting the axis-position instructing values Xr, Yr, Zr, $\alpha$r, $\beta$r, and $\gamma$r to Xs, Ys, Zs, $\alpha$s, $\beta$s and $\gamma$s(=0°), respectively.

Figure 31:
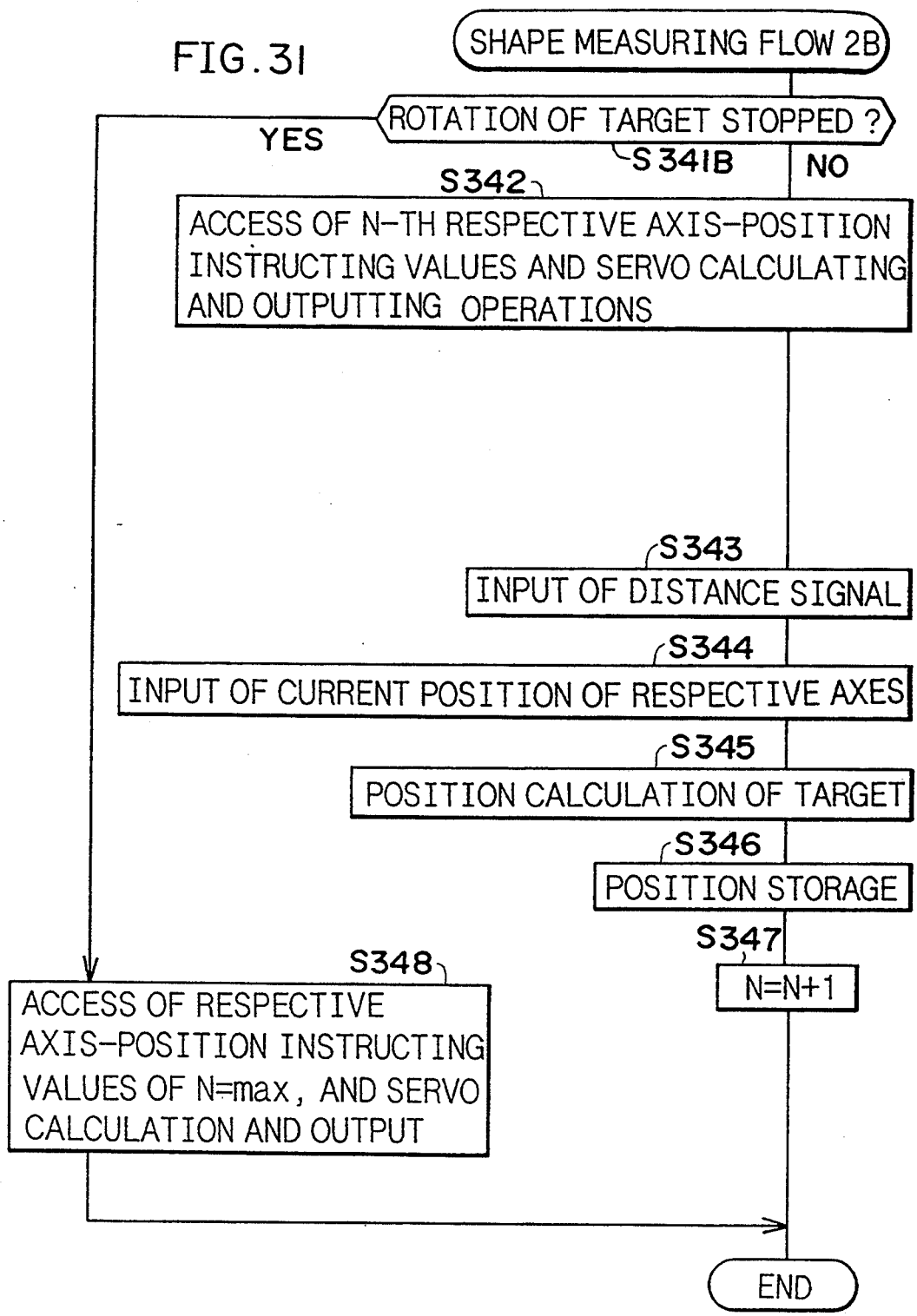

After the above positioning operation is completed, the variable N is set to 1 at the step S33, and the process goes to the step S34 to output an target rotating instruction signal instructing a start of the rotational scanning operation. In response to the output of the object rotating instruction signal at the step S34, a timer interrupting program as shown in FIG. 31 is executed at a constant time interval. This timer interrupting program of FIG. 31 differs from that of FIG. 8 in that this timer interrupting program judges as to whether the target rotating operation is stopped, and carries out detection and calculation of the angular position $\gamma$ of the turn table TB.

At the step S341B as shown in FIG. 31, when an target-rotation stopping instruction signal is judged not to be outputted, the process goes to a step S342 to access the axis-position instructing values Xr=$X_1$, Yr=$Y_1$, Zr=$Z_1$, $\alpha$r=$\alpha_1$, $\beta$r=$\beta_1$ and $\gamma$r=$\gamma_1$ for N=1. Thereafter, the signals Sx, Sy, Sz, S$\alpha$, S$\beta$ and S$\gamma$ for the respective axes are input through the respective position or angle detectors, and respective deviations between the above axis-position instructing values and the current positions ($X_0$, $Y_0$, $Z_0$, $\alpha_0$, $\beta_0$ and $\gamma_0$) of the respective axes (X-, Y-, Z-, $\alpha$-, $\beta$- and $\gamma$-axes) are calculated, and each of the deviations thus calculated is multiplied by a coefficient, whereby a servo computing operation is carried out. The servo-computed result is outputted to the servo amplifiers 13X to 13β and 13T as shown in FIG. 26A to perform a position servo-control of the respective axes. Through the above processes, the distance sensor unit 10 is moved to an instructed first position. At this time, the ultrasonic probe 10 is oriented to a normal direction to the surface of the target W at the measuring point. At the step S343, the distance 1a between the surface of the target W and the ultrasonic probe 10 is calculated on the basis of the signal SW. Next, the signals SX, SY, SZ, Sα, Sβ and Sγ for the respective axes are input through the respective position or angle detectors at the step S344, and the current positions ($X_0$, $Y_0$, $Z_0$, $α_0$, $β_0$ and $γ_0$) of the respective axes (X-, Y-, Z-, α-, β-, and γ-axes) are calculated at the step S345. On the basis of these current positions for the respective axes and the calculated distance 1a are calculated three-dimensional positions (Xa, Ya, Za) of the point on the surface of the target W to which an ultrasonic beam is radiated from the ultrasonic probe 10, and the angle γa of the turn table TB. Here, the values Xa to Za and γa are calculated by the following equations.

$$Xa = f1(X_0, Y_0, Z_0, α_0, β_0, 1a) \quad (69)$$

$$Ya = f2(X_0, Y_0, Z_0, α_0, β_0, 1a) \quad (70)$$

$$Za = f3(X_0, Y_0, Z_0, α_0, β_0, 1a) \quad (71)$$

$$γa = f4(Xa, Ya, γ_0) \quad (72)$$

A distance $D_l$ of the point on the surface of the target W which an ultrasonic beam is radiated from the Z-axis is calculated by the following equation (73).

$$D_l = \sqrt{Xa^2 + Ya^2} \quad (73)$$

Thereafter, the surface position on the target W which is calculated using the equations (69) to (73) is stored in the memory at the step S346. An example of a storing mariner of the data in the memory will be described with reference to FIG. 32.

Figure 32:
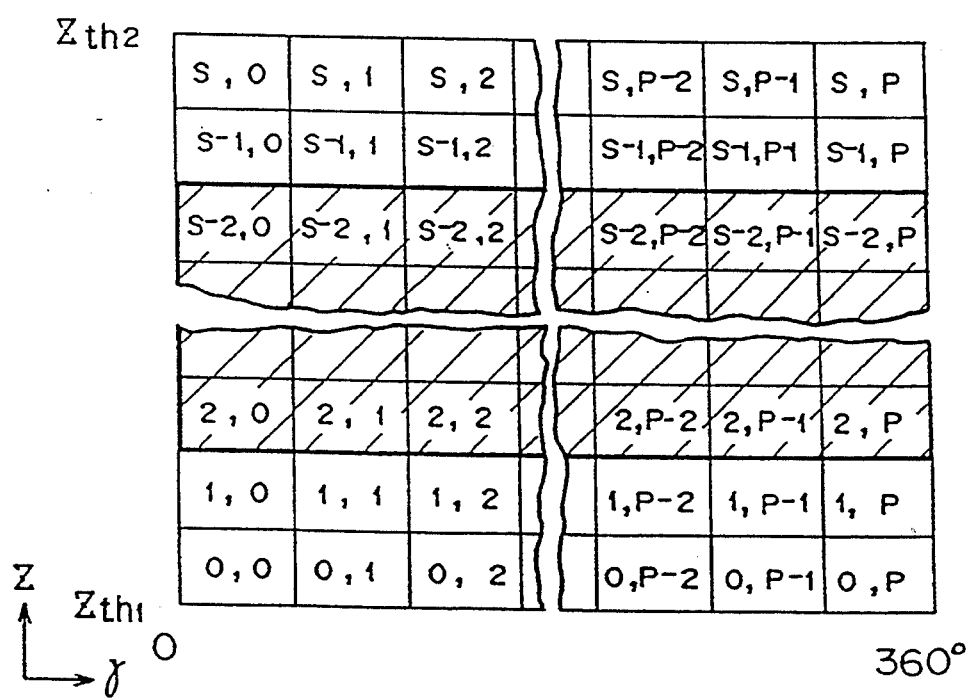

FIG. 32 shows segmentation (mapping) of a storing area in which the position data is stored, and corresponds to FIG. 9. The mapping of the storing area as shown in FIG. 32 differs from that of FIG. 9 in the following two points. That is, one is a content of the storing area, and the other is a coordinate system of the storing area, that is, the axes of the abscissas and ordinates represent the rotational angle γ of the turn table TB and the Z-axis, respectively. An oblique area as shown in FIG. 32 is a flaw detection area of the target W in the Z-axis. The storing area for the position data is designed to be slightly larger than the flaw detection area, however, is divided into plural storing sub-areas (0° to 360°) which comprises sub-areas of (P+1) in the γ-axial direction and sub-areas (Zth1 to Zth2) of (S+1) in the Z-axial direction.

A storing sub-area in which the Za and γa obtained by the equations (71) and (72) should be located is specified, and then the values of Za, $D_l$, γa and a flag representing completion of a storing operation are stored as a position data in the specified storing sub-areas. In this case, a pitch (angular) interval between neighboring sub-areas in the γ-axial direction is designed so as to be larger than that of the rotational scanning operation in the γ-axis direction. Therefore, in each of rotational scanning operations, there occurs a case where two or more position data must be stored in one storing sub-area when a position data is stored every rotational sub-scanning operation. This reduces the effect of the segmentation (mapping) of the storing area. Therefore, if it is judged that a position data of a current scanning operation (for example, a scanning operation for N=q) belongs to (is located in) a sub-area in which a position data of a previous scanning operation (for example, a scanning operation for N=q−1) has been already stored, then only one position data is stored in each storing sub-area.

The process goes to the step 8347 to add the variable N with 1, that is, to set the variable N to 2, and the process is completed.

Figure 33:
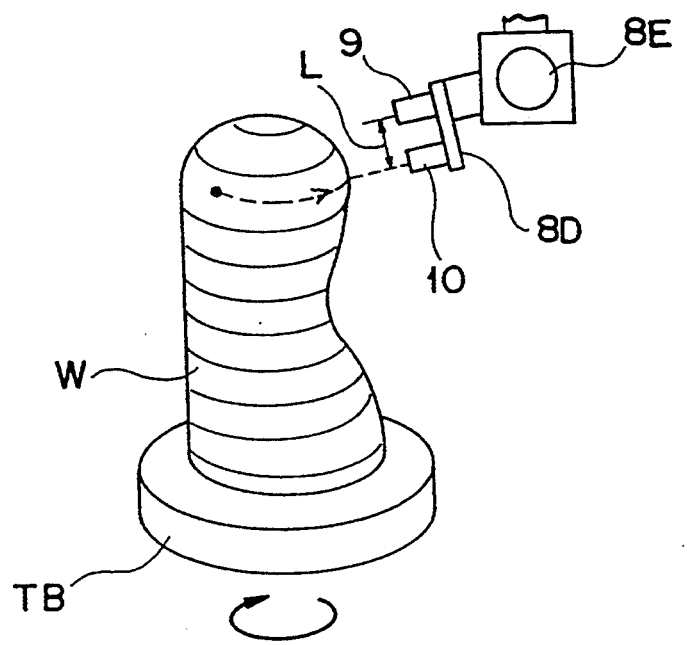

When the timer interrupting program as shown in FIG. 31 is completed, the process goes to a step S35B as shown in FIG. 30 to make an judgment of the completion of a (360°) full-rotational scanning operation by judging as to whether the variable N is equal to a value of (max+1). The judging operation of the step S35B is repetitively carried out until the full-rotational scanning operation is judged to be completed, and the timer interrupting program is executed at a constant time interval between the successive judging operations of the step S35B, whereby the target W is rotationally scanned on the turn table as shown in FIG. 33. In association with the rotational scanning operation of the target W, the position data D, Z and γ on the surface shape of the target W are stored in the corresponding storing areas in the storing manner as described above.

When upon completion of the one full-rotational scanning operation, the variable N is set to the value of (max+1), the program goes from the step S35B to the step S36B to output the object-rotation stopping instruction signal. In response to the object-rotation stopping instruction signal, the timer interrupting program goes to the step S348 to access the last axis-position instructing values of Xmax, Ymax, Zmax, αmax, βmax and γmax (=360°) for one full-rotational scanning operation, thereby performing the servo computing operation. The servo-computed result is outputted to the servo amplifiers 13X to 13β and 13T.

Upon completion of one full-rotational scanning operation in the X-axial direction as described above, the process goes to the step S37 as shown in FIG. 31 to judge as to whether the shape measuring operation is completed. Similarly in the first embodiment, in this embodiment a preceding rotational scanning line which precedes (away from) the current rotational scanning line in the Z-axial direction by the distance L is scanned by the ultrasonic probe 10 to obtain the surface shape data thereof, and a control point for the preceding rotational scanning line to which the ultrasonic probe 9 is positioned to perform the rotational scanning operation is calculated on the basis of the surface shape data obtained by the ultrasonic probe 10. Accordingly, the rotational scanning operation for the shape measurement is repeated until the ultrasonic probe 9 is downwardly moved in the Z-axial direction by the distance L as shown in FIG. 27A.

Figure 34:
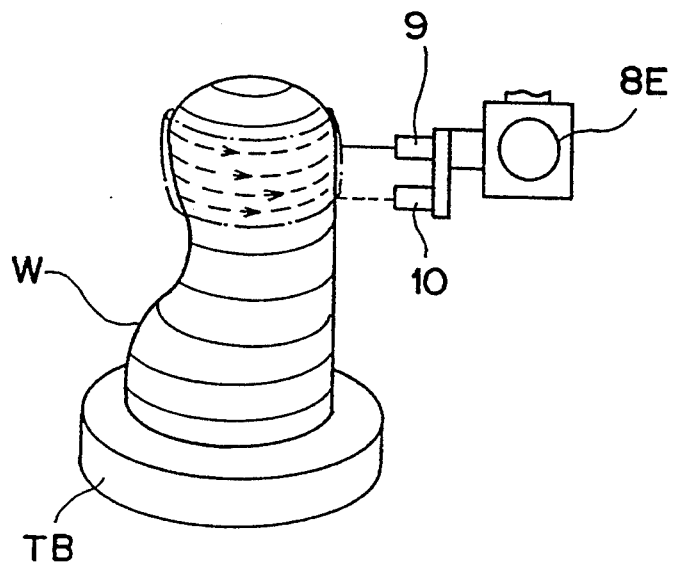

As shown in FIG. 34, the shape measuring operation is judged to be completed at the instantaneous time when the ultrasonic beam of the ultrasonic probe 9 reaches a flaw detection area whose surface shape data has been stored through the shape measuring operation as shown in FIG. 31, and the process goes from the step S37 as shown in FIG. 30 to the step S40 for the flaw detecting operation of the main flowchart of FIG. 5. Through the shape measuring operation prior to the flaw detecting operation, the position data on the surface shape of a flaw detection area indicated by a one-dotted line of FIG. 34 is stored in the storing manner as shown in FIG. 32.

(3) Process of the flaw detecting operation

The flaw detecting operation at the step S40 of FIG. 5 will be described hereunder.

FIG. 35 is a detailed flowchart for the flaw detecting operation of the step S40, and is substantially similar to that of the shape measuring operation of the process of FIG. 30. At a step S41A, axis-position instructing values for the flaw-detecting ultrasonic probe 9 for one full-rotational scanning operation is first calculated. This calculation will be described in more detail with reference to FIGS. 36 and 37.

Figure 36:
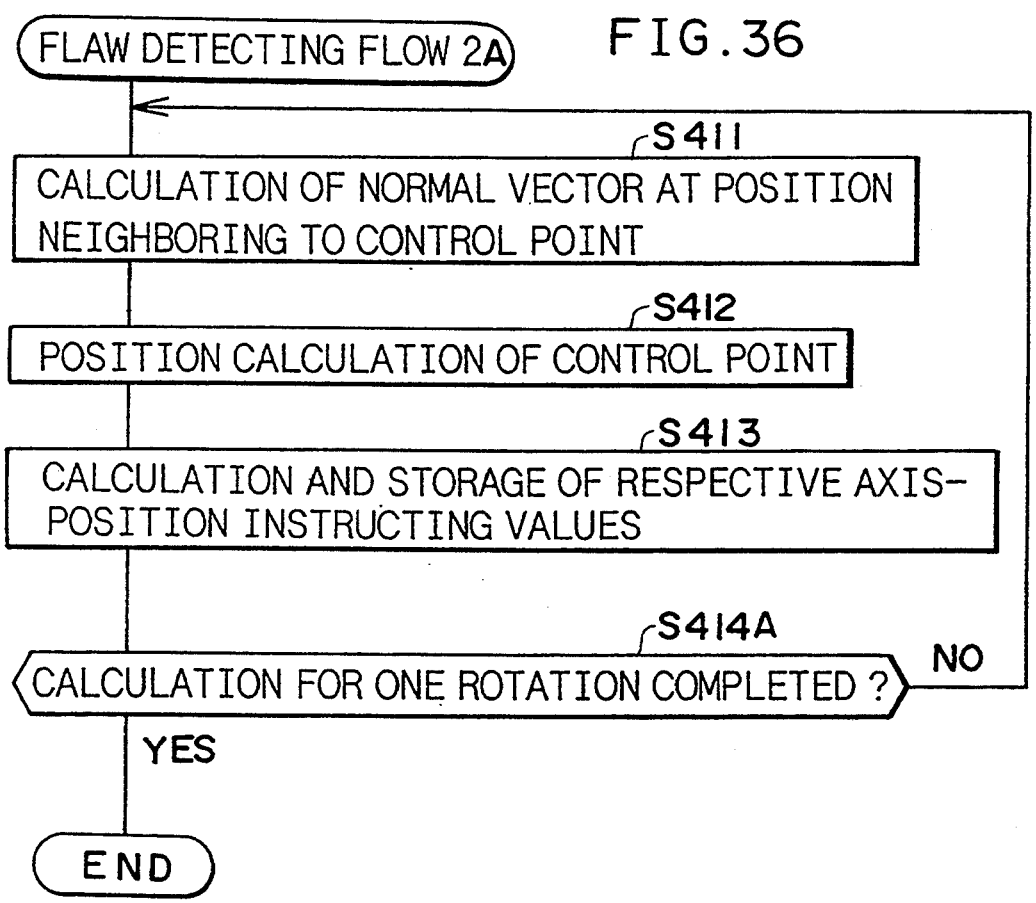
Figure 37:
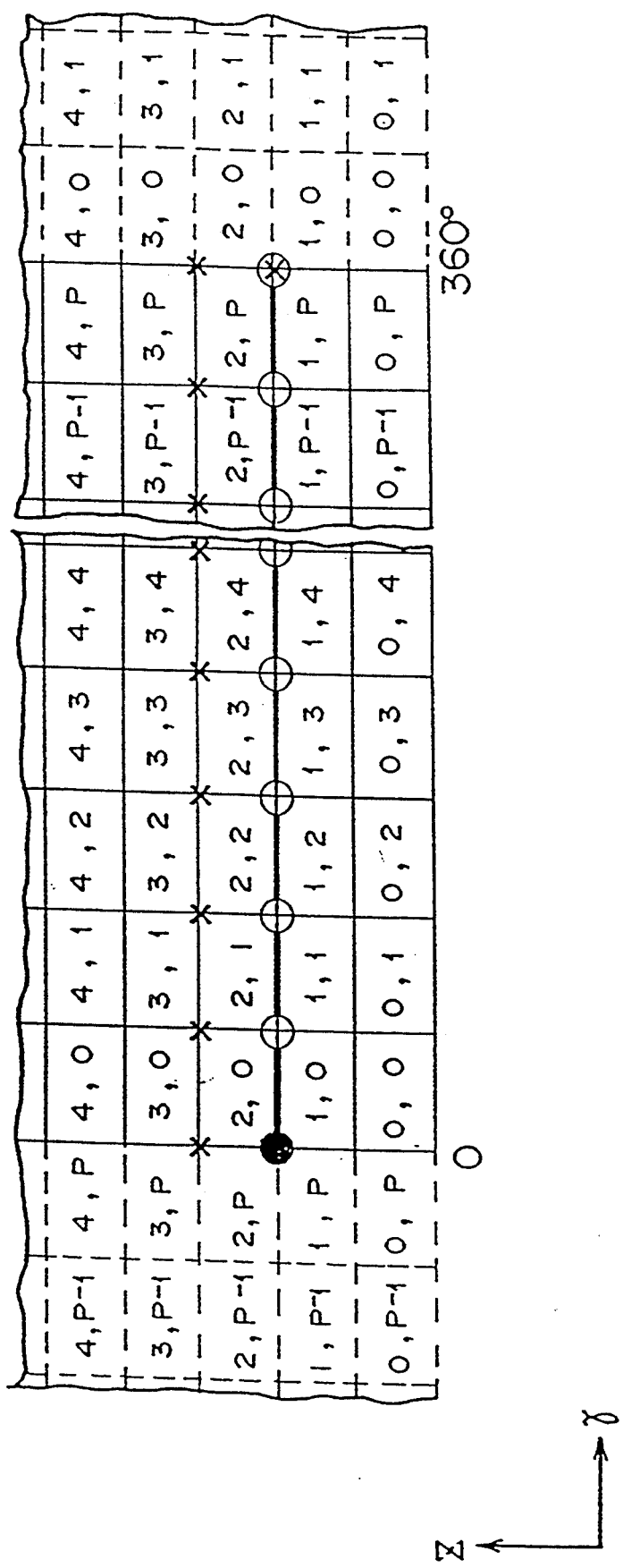

FIG. 36 is a flowchart for the calculation of the axis-position instructing values for one full-rotational scanning operation for the flaw detection at the step S41A, and FIG. 37 is an explanatory diagram for a manner of selecting one of the position data on the surface shape of the target W in the calculation of the axis-position instructing values. FIGS. 36 and 37 corresponding to FIGS. 13 and 14 of the first embodiment. A bold line as shown in FIG. 37 represents a scanning line for the flaw detection by the ultrasonic probe 9, and the flowchart of FIG. 36 carries out the calculation of the axis-position instructing values at control points which are located between control points represented by a black circle and an X-lettered white circle as shown in FIG. 37.

At a step S411 as shown in FIG. 36, the vector of a normal to the surface of the target W (a normal vector) of a position which is neighboring to any control point is calculated in the same manner as the first embodiment. For example, a first normal vector N ($N_x$, $N_y$, $N_z$) for a first control point represented by the black circle is calculated by the following equations which are used in the first embodiment.

$$Nx = \sum_{i=1}^{4} (Yi - Yj) \times (Zi + Zj) \quad (13)$$

$$Ny = \sum_{i=1}^{4} (Zi - Zj) \times (Xi + Xj) \quad (14)$$

$$Nz = \sum_{i=1}^{4} (Xi - Xj) \times (Yi + Yj) \quad (15)$$

Here, if i is not equal to 4, j=i+1, and if i is equal to 4, j=1.

The values of X1 to X4 and Y1 to Y4 are calculated by the following equations (74) and (75) using the values of angle $\gamma a$ and the distance $D_l$ before the calculation of the normal vector.

$$X1 = D_l \sin(\gamma a - \gamma) \quad (74)$$

$$Y1 = D_l \cos(\gamma a - \gamma) \quad (75)$$

Next, the position of the control point is calculated at the step S412. Representing the position of the first control point of black circle as shown in FIG. 37 by (Xk, Yk, Zk), the values of Zk is a known value because the value Zk is introduced to set a storing area, and the value of Yk is a known value because the central coordinate of the turn table TB is set to (0,0,0) and thus the value of Yk is equal to zero. Therefore, the position calculation of the step S412 is equivalent to calculation of the value of Xk.

The coefficient d of the plane equation of the plane PL as shown in FIG. 15 is calculated using the coordinate (Xm, Ym, Zm) of a position neighboring to the first control point of black circle as follows.

$$d = -(NxXm + NyYm + NzZm) \quad (17)$$

The value of Xk for the first control point of black circle is calculated using the coefficient d thus obtained as follows.

$$Xk = -(d + NyYk + NzZk)/Nx \quad (76)$$

The coordinate value (Xm, Ym, Zm) used for the above calculation of the coefficient d is calculated in the same manner as the first embodiment.

Through the above calculating operations, the normal vector N (Nx, Ny, Nz) and the position (Xk, Yk, Zk) are obtained.

The process of the program as shown in FIG. 36 goes to a step S413 to perform calculating and storing operations of the axis-position instructing values for the respective axes. Here, setting the axis-position instructing values to such values that the distance between the ultrasonic probe 9 and the surface of the target W is equal to $l_0$ at all times, the axis-position instructing values (Xr, YF, Zr, $\alpha r$, $\beta r$) for the respective axes are determined by the following equations (77) to (81), and then stored.

$$Xr = f5(Xk, Yk, Zk, Nx, Ny, Nz, l_0) \quad (77)$$

$$Yr = f6(Xk, Yk, Zk, Nx, Ny, Nz, l_0) \quad (78)$$

$$Zr = f7(Xk, Yk, Zk, Nx, Ny, Nz, l_0) \quad (79)$$

$$\alpha r = f8(Nx, Ny, Nz) \quad (80)$$

$$\beta r = f9(Nx, Ny, Nz) \quad (81)$$

In this case, the angle instructing value of the turn table TB at the control point of the black circle is simultaneously stored.

Next, the program goes to a step S414A to judge as to whether the calculation of the axis-position instructing values for one full-rotational scanning operation is completed. The steps S411 to 414A are repetitively carried out until it is judged that one full-rotational scanning operation is completed, and the calculation for the control points between the black circle and the X-lettered white circle is completed. Thereafter, the process goes from the step S414A to the step S42 of FIG. 35. In this case, the respective axis-position instructing values for one full-rotational scanning operation comprise the following data groups.

$$Xr = (Xr_s, Xr_1, \ldots Xr_n, \ldots Xr_{max}) \quad (82)$$

$$Yr = (Yr_s, Yr_1, \ldots Yr_n, \ldots Yr_{max}) \quad (83)$$

$$Zr = (Zr_s, Zr_1, \ldots Zr_n, \ldots Zr_{max}) \quad (84)$$

$$\alpha r = (\alpha r_s, \alpha r_1, \ldots \alpha r_n, \ldots \alpha r_{max}) \quad (85)$$

$$\beta r = (\beta r_s, \beta r_1, \ldots \beta r_n, \ldots \beta r_{max}) \quad (86)$$

$$\gamma r = (\gamma r_s, \gamma r_1, \ldots \gamma r_n, \ldots \gamma r_{max}) \quad (87)$$

Figure 38:
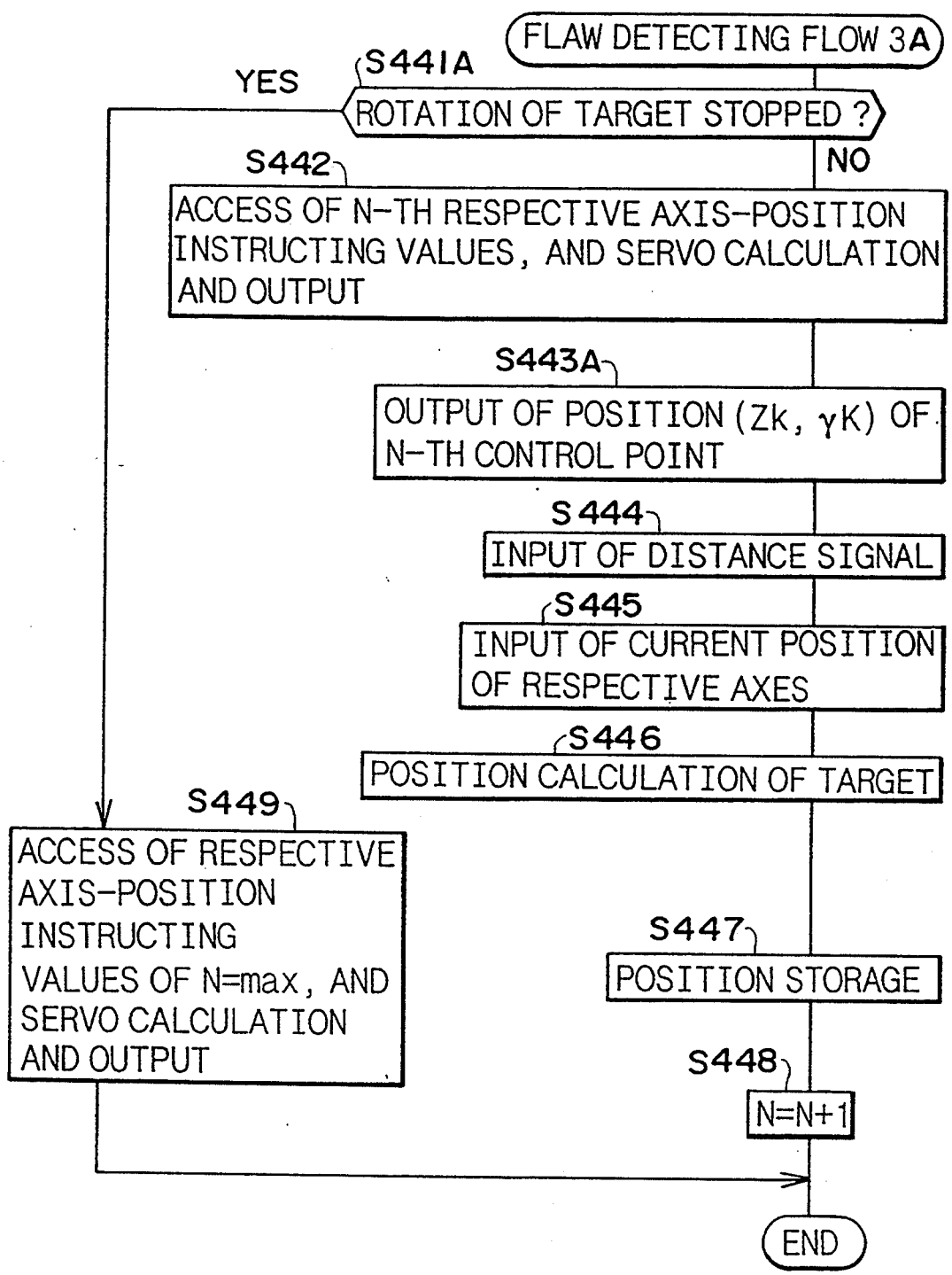

The processes of the steps S42 to the S45A of FIG. 35 are carried out using the data groups of the respective axis-position instructing values which are represented by the equations (82) to (87), and obtained at the step S412. Like the shape measuring operation, after the processes of the steps S42 and S43 are carried out and the target-rotating instruction signal, that is, the scan-starting instruction signal is outputted at the step S44, the timer interrupting program as shown in FIG. 38 is executed. The timer interrupting program of FIG. 38 differs from that of FIG. 17 in that it is judged at the step S441A as to whether the target-rotational stopping instruction signal is outputted, and in that the flaw detection signal outputted at the step S443A pertains to the position of a control point (Zk, γk).

At the step S441 as shown in FIG. 38, if it is judged that the target-rotational stopping instruction signal is not outputted, then the access of the N-th axis-position instructing values for the respective axis-driving members and servo calculating and outputting operations are carried out at the step S442. Thereafter, the process goes to the step S443 at which an output of the ultrasonic probe 9 is inputted and a flaw detection result is outputted as a position data (ZP, γr) for a control point to the recording device 15. Next, steps S444 to S448 which are similar to the steps of S343 to 347 as shown in FIG. 31 are successively carried out, and a preceding scanning line as shown in FIG. 37 is subjected to the shape measuring operation in parallel with the flaw detecting operation in the same manner as the first embodiment.

The processes as described above are repeated until one full-rotational scanning operation is completed, and then the process goes from the step S45A to the step S46A to output the target-rotational stopping instruction signal. When it is judged at the step S441 that the target-rotational stopping instruction signal is outputted, at the step S449, the access of the Nmax-th axis-position instructing values for the respective axis-driving members, the servo calculation and the output of the servo-calculated result are carried out. Thereafter, the process goes to the step S47, and it is judged as to whether the flaw detecting operation is completed. That is, it is judged as to whether the area surrounded by the bold line of FIG. 9 is wholly scanned. If it is judged that the area is not wholly scanned, the process returns to the step S41A to calculate the respective axis-position instructing values for next one rotational scanning operation, for example, on a scanning line which is marked by X-letters as shown in FIG. 37.

If the flaw detection area as indicated in FIG. 32 is wholly scanned, the process goes from the step S47 to the step S50 as shown in FIG. 5 to position the respective axis-driving members at predetermined terminal positions, and the control operation is completed.

In summary, the surface shape measuring and flaw detecting operations of the target W in the fourth embodiment as described above with reference to FIGS. 26A to 38 are carried out as follows.

(a) The target is rotated.

(b) The position and orientation of the distance sensor unit are controlled on the basis of the data on the surface shape of the target which is beforehand obtained, and then an ultrasonic signal for the distance measurement is radiated to the rotating target. Thereafter, the ultrasonic signal reflected from the target is detected and the distance between a distance measuring point and the distance sensor unit is calculated on the basis of the detected ultrasonic signal. From the distance data thus obtained and the current position of the distance sensors unit, the shape information of the measuring point on the target, that is, the surface shape data is obtained.

(c) The surface shape data is stored as a storing (position) data for any one of sub-areas into which the flaw detection area is segmented using the coordinate system of the rotational angle of the turn table and the Z-axis. In this embodiment, only one storing data is stored for each sub-area.

(d) The processes of (b) and (c) are repeated until the distance sensor unit is moved by a distance L as shown in FIG. 27A.

(e) The axis-position instructing values (data on position and orientation of the probe 9) for each control point are calculated from the surface shape data of the target W which are stored in the storing sub-areas through the processes (b), (c) and (d).

(f) The respective axis-driving members are driven using the axis-position instructing values to control the position and orientation of the ultrasonic probe 9 for the flaw detection, whereby an ultrasonic signal for the flaw detection is directed in the normal direction to the surface of the target W and the ultrasonic probe 9 is positionally kept away from the surface of the target by a predetermined distance.

(g) The ultrasonic signal is transmitted from the ultrasonic probe 9 to the surface of the target while the position and the orientation of the ultrasonic probe 9 is kept at predetermined states, thereby performing the flaw detecting operation.

(h) In parallel with the flaw detecting operation, an ultrasonic signal is transmitted from the distance sensor unit to the surface of the target to obtain a surface shape data of a preceding scanning line which is away from a current scanning line for the flaw detection by the distance L. This surface shape data is used to control the position and orientation of the ultrasonic probe in the flaw detecting operation of the preceding scanning line or a scanning line neighboring thereto.

According to the embodiment as described above, the probe for the flaw detection can be controlled to be oriented in the normal direction to the surface of the target and to be kept at a predetermined interval from the surface of the target with high accuracy at all times, and thus the flaw detection can be easily carried out for a body of revolution having irregular shape.

Further, since the shape measurement can be carried out simultaneously with the flaw detection, the whole flaw detection time is shortened.

Still further, the storing area for storing the position data is segmented into sub-areas using the coordinate system of the rotational angle of the turn table and the Z-axis, only one position data is stored in each storing sub-area, and a control point for the ultrasonic probe on any scanning line for the flaw detection is determined on the basis of the position data of each storing sub-area, so that the same effect as the first embodiment is also obtained in this embodiment.

Fifth Embodiment

In the embodiments as described above, the axis-position instructing values at each control point on any scanning line are calculated just when the flaw detecting operation for the scanning line is started. Therefore, there is a loss time when the ultrasonic probes 9 and 10 are left unmoved until an actual flaw detecting operation is started. This loss time is reduced by beforehand calculating respective axis-position instructing values for a next scanning line during the flaw detecting operation for a current scanning line.

The fifth embodiment of this invention will be described with reference to FIGS. 39 to 41.

Figure 39:
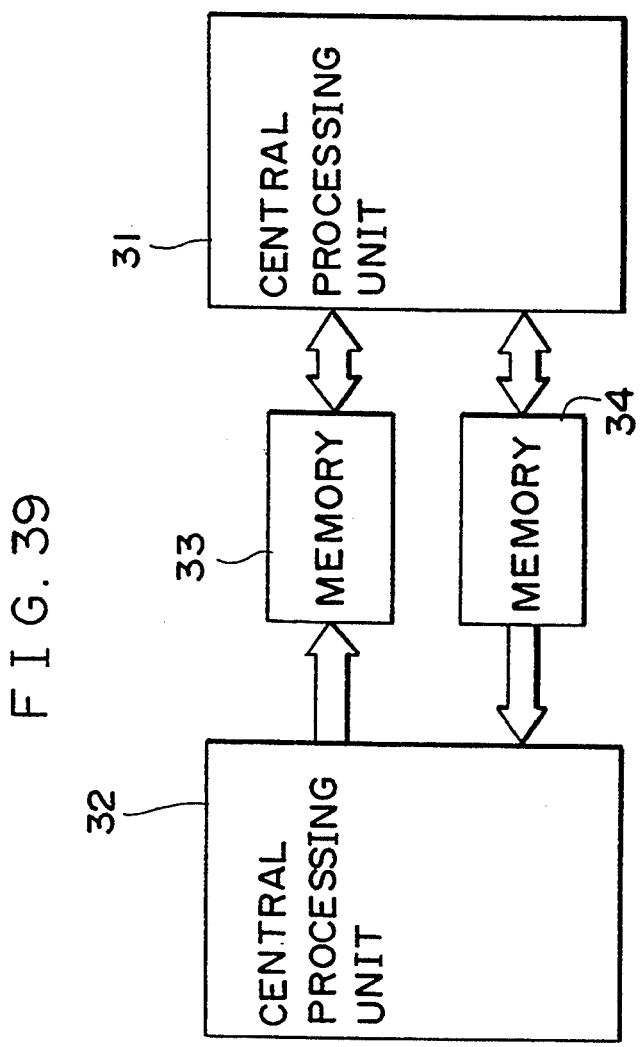
FIGS. 39 to 41 show a fifth embodiment.

FIG. 39 shows the hardware configuration of the fifth embodiment having two central processing units. A reference numeral 31 represents a central processing unit which serves to perform a calculation processing of axis-position instructing values for the respective axis-driving members for one scanning operation, and a reference numeral 32 represents a central processing unit which serves to perform processings other than that of the central processing unit 31. A reference numeral 33 represents a memory for storing position data on the surface of the target and a calculation starting flag indicating a start of the calculation of the respective axis-position instructing values for one scanning operation, and a reference numeral 34 represents another memory for storing the axis-position instructing values for the respective axis-driving members which have been calculated by the central processing unit 31 and a calculation terminating flag indicating a completion of the calculation of the respective axis-position instructing values for one scanning operation.

Figure 40:
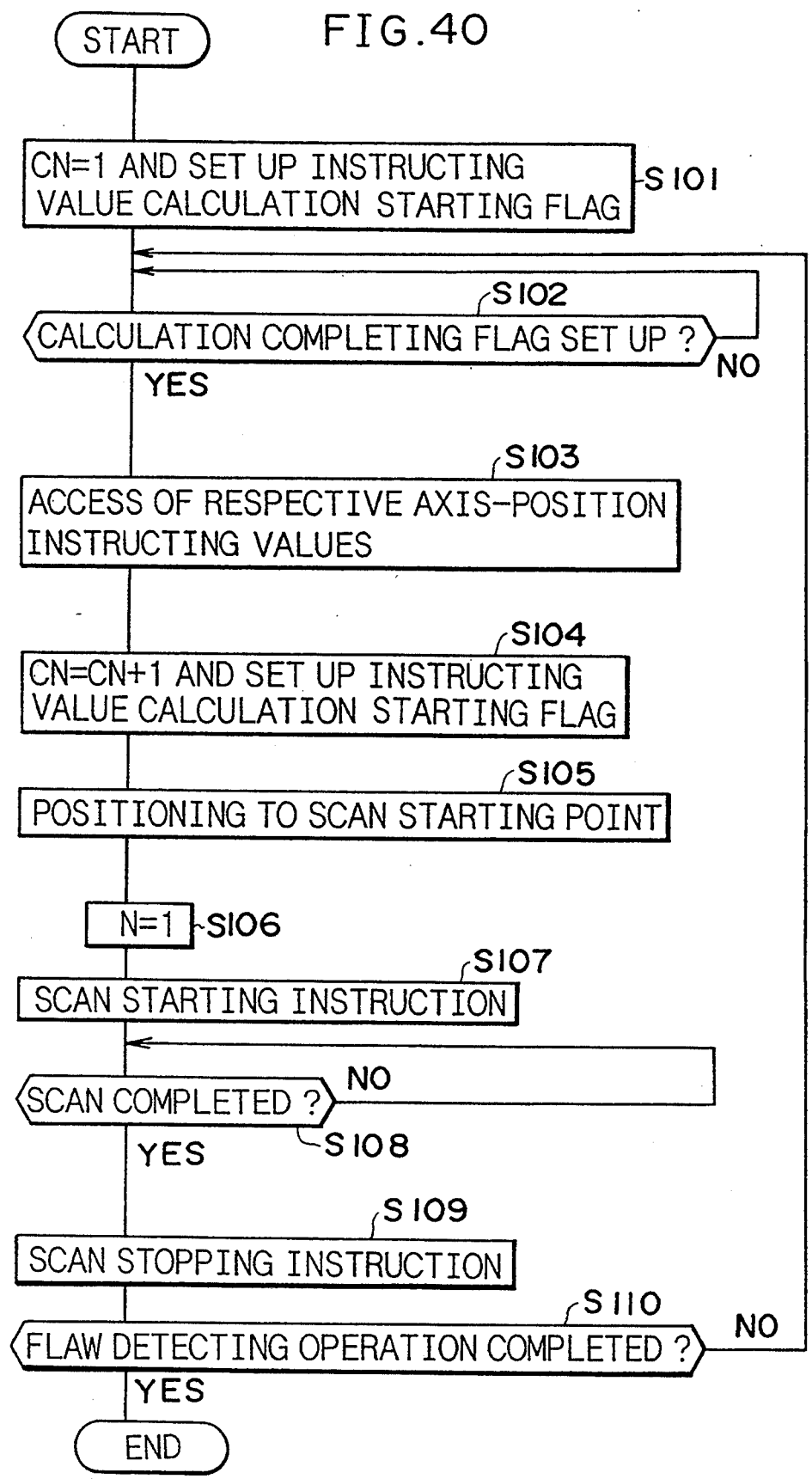
Figure 41:
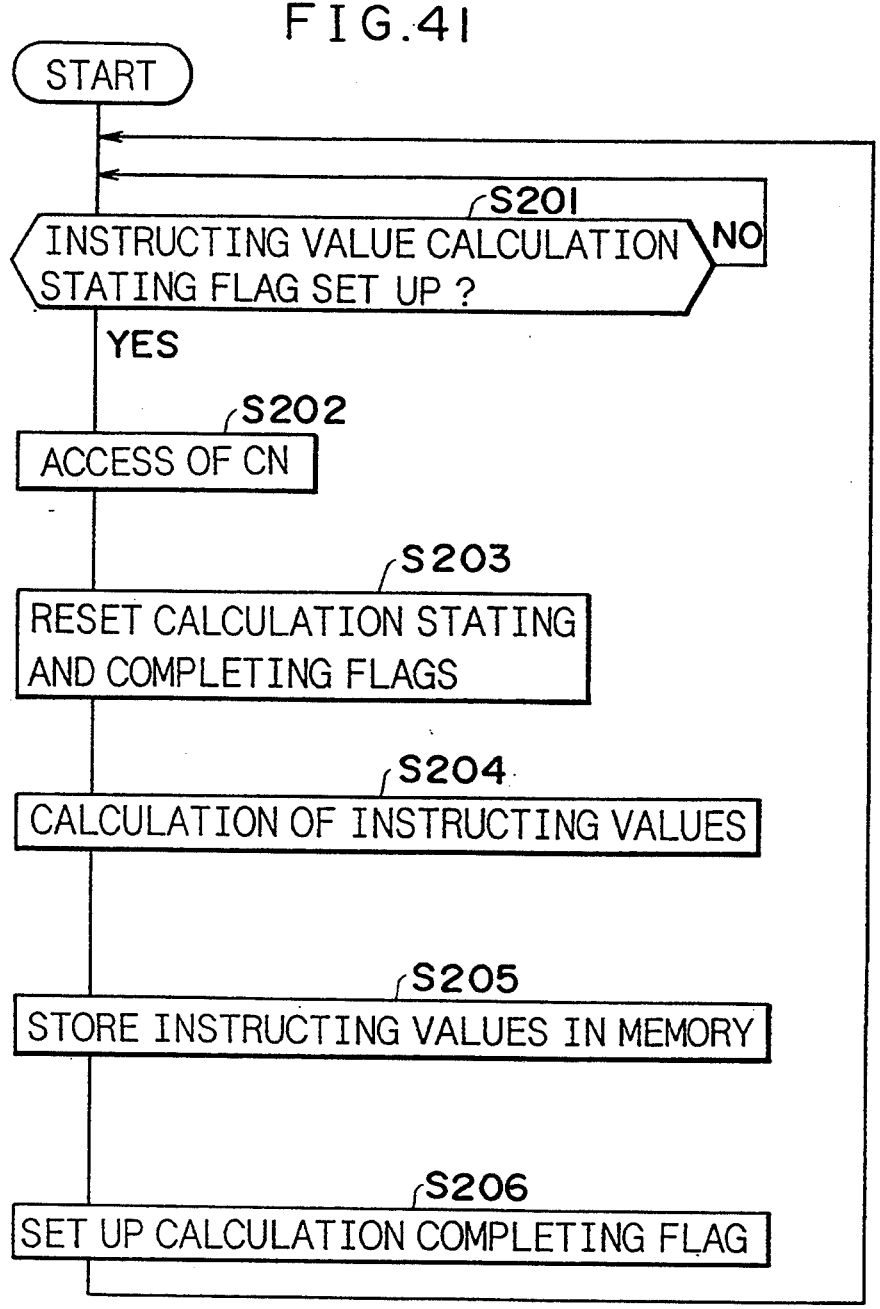

FIG. 40 is a detailed flowchart for the flaw detecting operation of the central processing unit 32 (corresponding to FIG. 35), and FIG. 41 is a flowchart for the operation of the central processing unit 31.

An operation of this embodiment will be described hereunder.

At a step S101, a count number CN of a scanning counter is first set to 1, and the calculation starting flag is set up in the memory 33. The process is on standby until the calculation terminating flag is set up at a step S102.

In the process flow as shown in FIG. 41, the process is first on standby until the calculation starting flag is set up at aS201. If the calculation starting flag is set up at the step S101 of FIG. 40, the process goes to the step S202 to read in the count number CN of the scanning counter, and the calculation starting flag and the calculation terminating flag are reset at a next step S203. Of course, the calculation terminating flag is reset in the initial stage.

The process goes to the step S204 to perform the calculation of the respective axis-position instructing values for a scanning line corresponding to the count number CN, that is, a first scanning line at the initial stage. This calculation is the same as that of the steps S411 to S414A of FIG. 36. Thus, those of ordinary skill in the art would readily appreciate that the fifth embodiment of FIGS. 39-41 can be applied to the embodiments of both FIGS. 1 and 26. The axis-position instructing values thus obtained are stored in the memory 34 at a step S205. In addition, the calculation terminating flag is set up in the memory 34 at a step S206, and the process returns to the step S201 to be on standby for a calculation starting instruction for a next scanning line.

Setting up the calculation terminating flag, the process of the program as shown in FIG. 40 goes from the step S102 to a step S103 to access the respective axis-position instructing values from the memory 34. At a step S104, the count number CN of the scanning counter is added with 1 to set up the calculation starting flag for the calculation of the respective axis-position instructing values. Further, at steps S105 to S109, the first scanning line is subjected to the flaw detection. During the flaw detecting operation, a second scanning line is subjected to the calculation of the axis-position instructing values in the central processing unit 31.

As described above, according to the fifth embodiment, the flaw detecting operation and the calculating operation for the respective axis-position instructing values are carried out in parallel with (simultaneously with) each other, and thus a period from a start time of the flaw detection till a completion time of the flaw detection can be further shortened.

Sixth Embodiment

Figure 42:
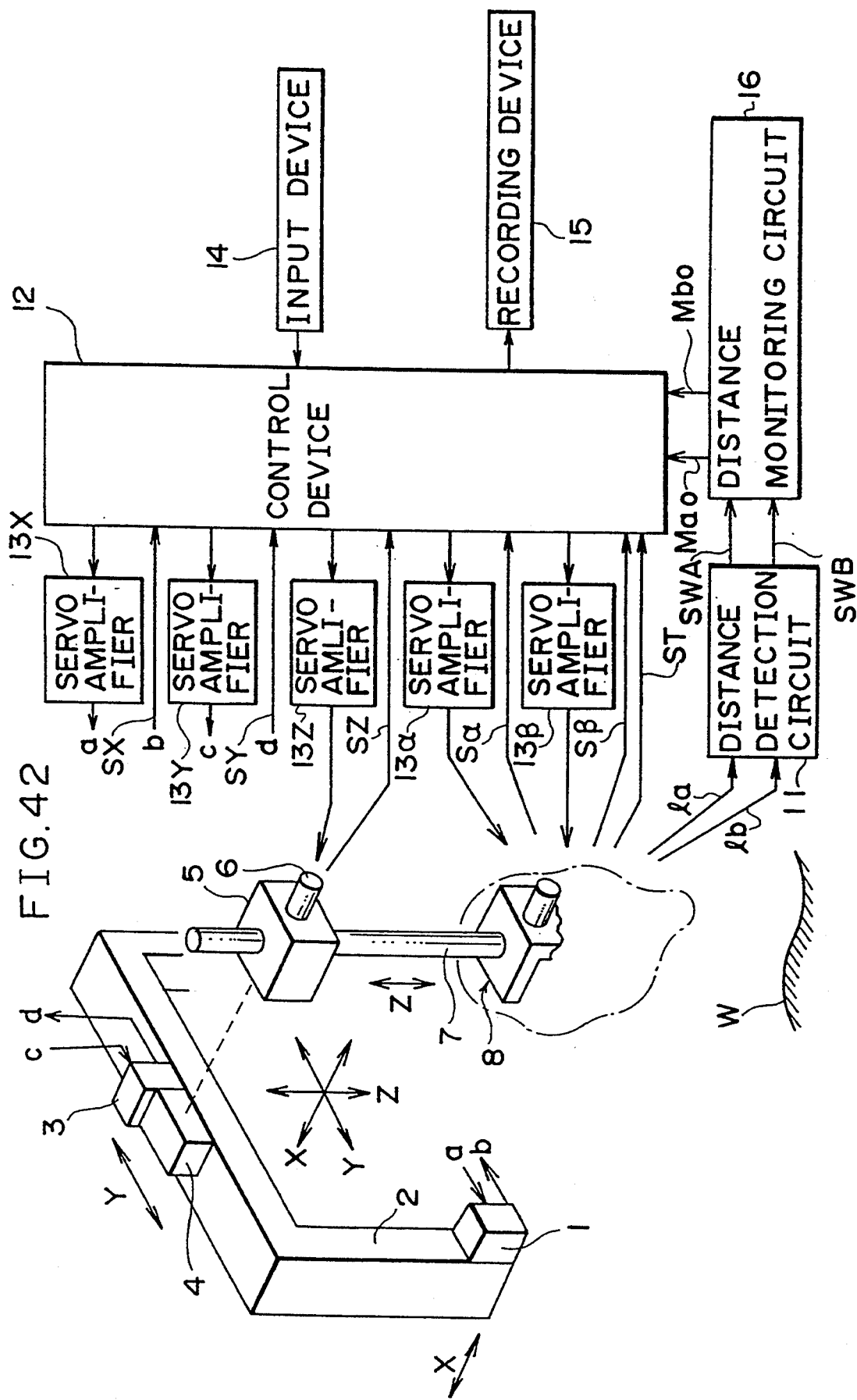
FIGS. 42 to 47 show a sixth embodiment of this invention.

FIGS. 42 to 47 show a sixth embodiment of this invention. This embodiment has the same construction as the first embodiment, except that a distance monitoring unit 16 for monitoring detection signals of the distance detection sensors 10a and 10b and excluding the detection signals when the detection signals are judged to be abnormal. FIG. 42 shows the whole construction of the three-dimensionally moving member and the control system of the sixth embodiment, and the same elements as those of FIG. 1 are represented by the same reference numerals.

The distance monitoring unit 16 as described below is also applicable not only to the first embodiment, but also the second to fifth embodiments as described above.

Figure 43:
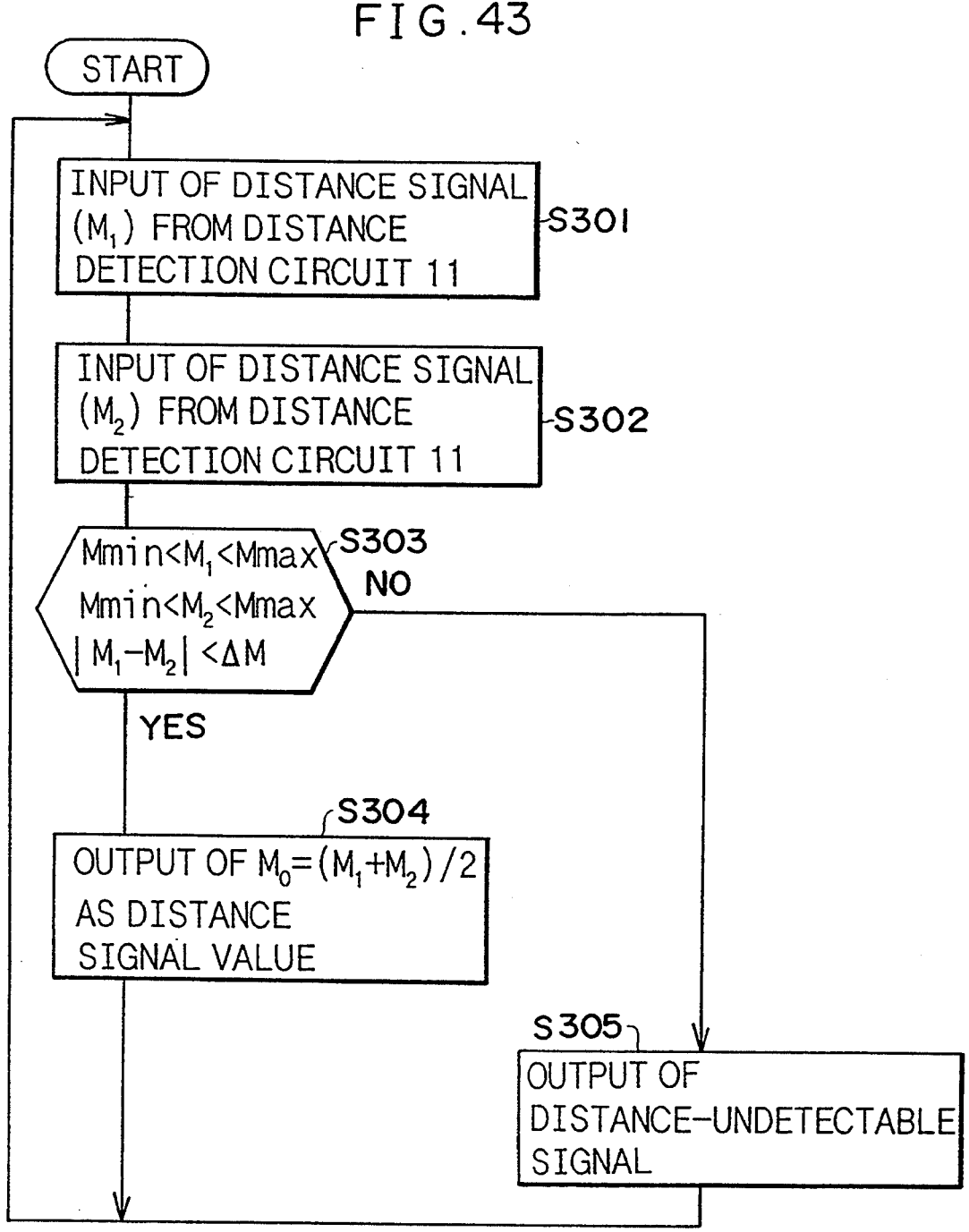

FIG. 43 is a flowchart for a processing of the distance monitoring unit 16 when a computer is used as the distance monitoring unit 16. The processing of FIG. 43 is conducted to an output signal of the distance detection circuit 11A of FIG. 4, and an output signal of the distance detection circuit 11b is also subjected to the same processing.

At a step S301, a distance signal SWA (SWB) is input from the distance detection circuit 11 to the distance monitoring unit 16, and the input distance value is represented by M1. Thereafter, a subsequent distance signal SWA (SWB) is again input from the distance detection circuit 11 to the distance monitoring unit 16 at the step S302, and the input distance value is represented by M2. The following conditions (88) to (90) are examined for the distance values M1 and M2 at a step S303.

$$Mmin < M_1 < Mmax \tag{88}$$

$$Mmin < M_2 < Mmax \tag{89}$$

$$|M_1 - M_2| < \Delta M \tag{90}$$

If all the conditions (88) to (90) are satisfied, then the distance signal SWA(SWB) is judged to be normal, and then the program goes to a step S304 to output a mean of the values $M_1$ and $M_2$ to the control device 12 as a distance signal $M_0$ ($Ma_0$ or $Mb_0$ in FIG. 42). If at least one of the conditions (88) to (90) is not satisfied at the step S303, then the distance signal SWA(SWB) is judged to be abnormal, and then the program goes to a step S305 to output a distance-undetectable signal, for example, a signal $M_0=0$ to the control device 12.

Accordingly, in this embodiment, an abnormal distance value due to a flaw or the like On the surface of the target or an abnormal value due to failure of signal transmission or reception can be excluded through the examination of the conditions (88) to (90). In the above processing, Mmin and Mmax represent minimum and maximum distances which are expectable in the shape measuring and flaw detecting operations. Further, AM represents a permissible range of variation in distance. For example, when signal transmission or reception is failed in the input operation of M1 to the distance monitoring unit 16, a value of $|M_1-M_2|$ is extremely large. From this extremely-large value, the value of M1 is judged to an abnormal value and thus is intentionally excluded or eliminated from the distance data.

Calculation Processing of the Control Device 12

(1) Main flowchart

The main flowchart of this embodiment is identical to that of the first embodiment as shown in FIG. 5, and thus the description thereof is eliminated.

The shape measuring and flaw detecting operations of this embodiment will be next described in more detail.

(2) Process for the shape measuring operation

Figure 44:
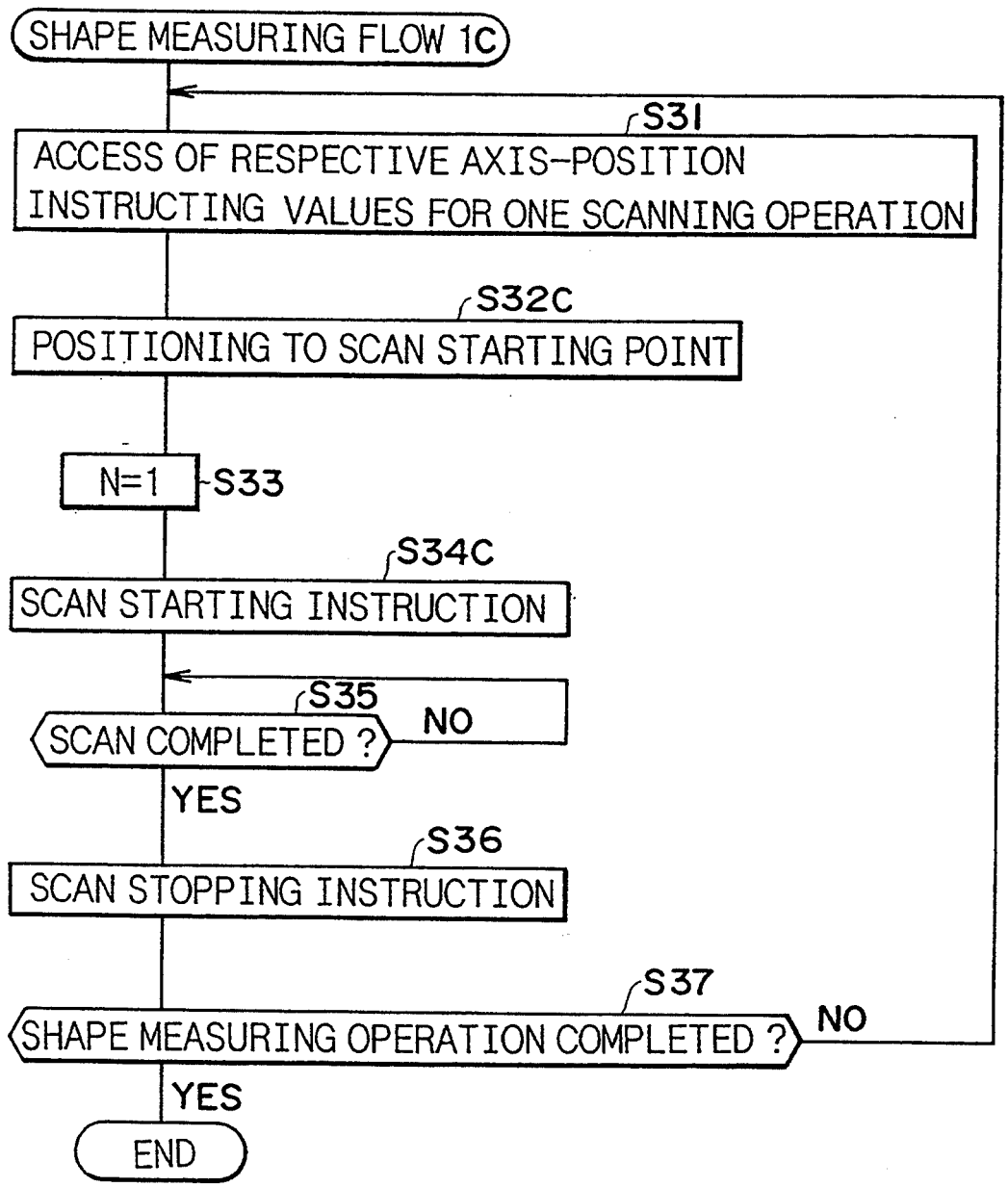

FIG. 44 is a detailed flowchart for the shape measuring operation of the step S30 of the main flowchart.

At a step S32C, the respective axis-position instructing values for a scan starting position which comprise data groups represented by equations (91) to (95) are accessed, and each of the respective axis driving members is positioned.

$$Xr=Xs \qquad (91)$$

$$Yr=Ys \qquad (92)$$

$$Zr=Zs \qquad (93)$$

$$\alpha r=\alpha s \qquad (94)$$

$$\beta r=\beta s \qquad (95)$$

Figure 45:
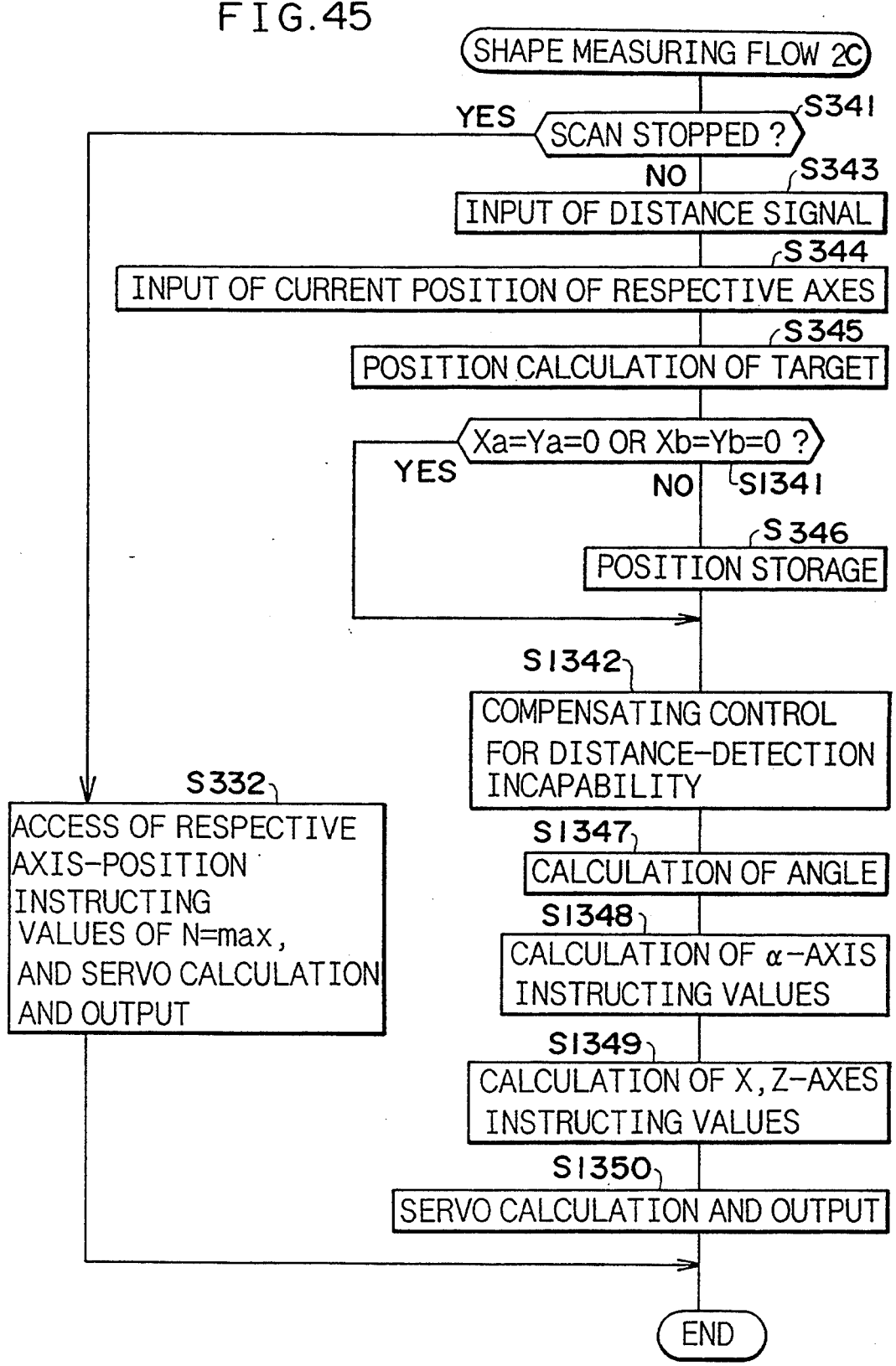

The process goes to a step S34C to output a scan starting instruction signal, and then a timer interrupting program as shown in FIG. 45 is executed at a constant time interval. This program is carried out in the same manner as the flowchart of FIG. 24, and the same processings as those of FIG. 24 are represented by the same reference numerals.

In the flowchart of FIG. 45, it is first judged at a step S341 as to whether a scan stopping instruction signal is outputted.

At a first stage, the scan stopping instruction signal is not judged to be outputted because at the first stage the scan starting instruction signal is outputted, and thus the process goes to a step S343 to take in information on distances $1a$ and $1b$ between the surface of the target W and each of the ultrasonic probes 10a and 10b through the signals Ma0 and Mb0 from the distance monitoring unit 16. In addition, at the step S324 the signals SX, SY, SZ, S$\alpha$ and S$\beta$ which represent current positions of the respective axes are input through the respective position or angle detectors to calculate a current positions (X0, Y0, Z0, $\alpha$0 and $\beta$0) of the axes (X-, Y-, Z-, $\alpha$- and $\beta$-axes). On the basis of these current positions for the respective axes and the calculated distances $1a$ and $1b$ are calculated three-dimensional positions (Xa, Ya, Za) and (Xb, Yb, Zb) on the surface of the target W to which the ultrasonic beams are radiated from the ultrasonic probes 10a and 10b, respectively. Here, the values Xa to Zb are calculated by the following equations as used in the first embodiment.

$$Xa=f1(X0, Y0, Z0, \alpha0, \beta0, 1a) \qquad (7)$$

$$Ya=f2(X0, Y0, Z0, \alpha0, \beta0, 1a) \qquad (8)$$

$$Za=f3(X0, Y0, Z0, \alpha0, \beta0, 1a) \qquad (9)$$

$$Xb=f1(X0, Y0, Z0, \alpha0, \beta0, 1a) \qquad (10)$$

$$Yb=f2(X0, Y0, Z0, \alpha0, \beta0, 1a) \qquad (11)$$

$$Zb=f3(X0, Y0, Z0, \alpha0, \beta0, 1a) \qquad (12)$$

If the values of Ma0 and Mb0 are judged to be abnormal values, that is, the distance monitoring unit 16 outputs zero-values (Ma0=Mb0=0), the values of Xa to Zb are calculated into zero. Next, at a step S1341, it is judged as to whether the equation Xa=Ya=0 or Xb=Yb=0 is satisfied. If this judgment is "no", in other words, if the values of Xa to Yb are judged to be normal values, the process goes to the step S1346. Inversely, if this judgment is "yes", in other words, if the values of Xa to Yb are judged to be abnormal values, the process goes to the step S1342. At the step S1346, the surface position of the target W which are obtained by the equations (7) to (12) are stored. The storing manner of this embodiment is also identical to that of the first embodiment as shown in FIG. 9. Thereafter, the program goes to the step S1342 of FIG. 45.

Figure 46:
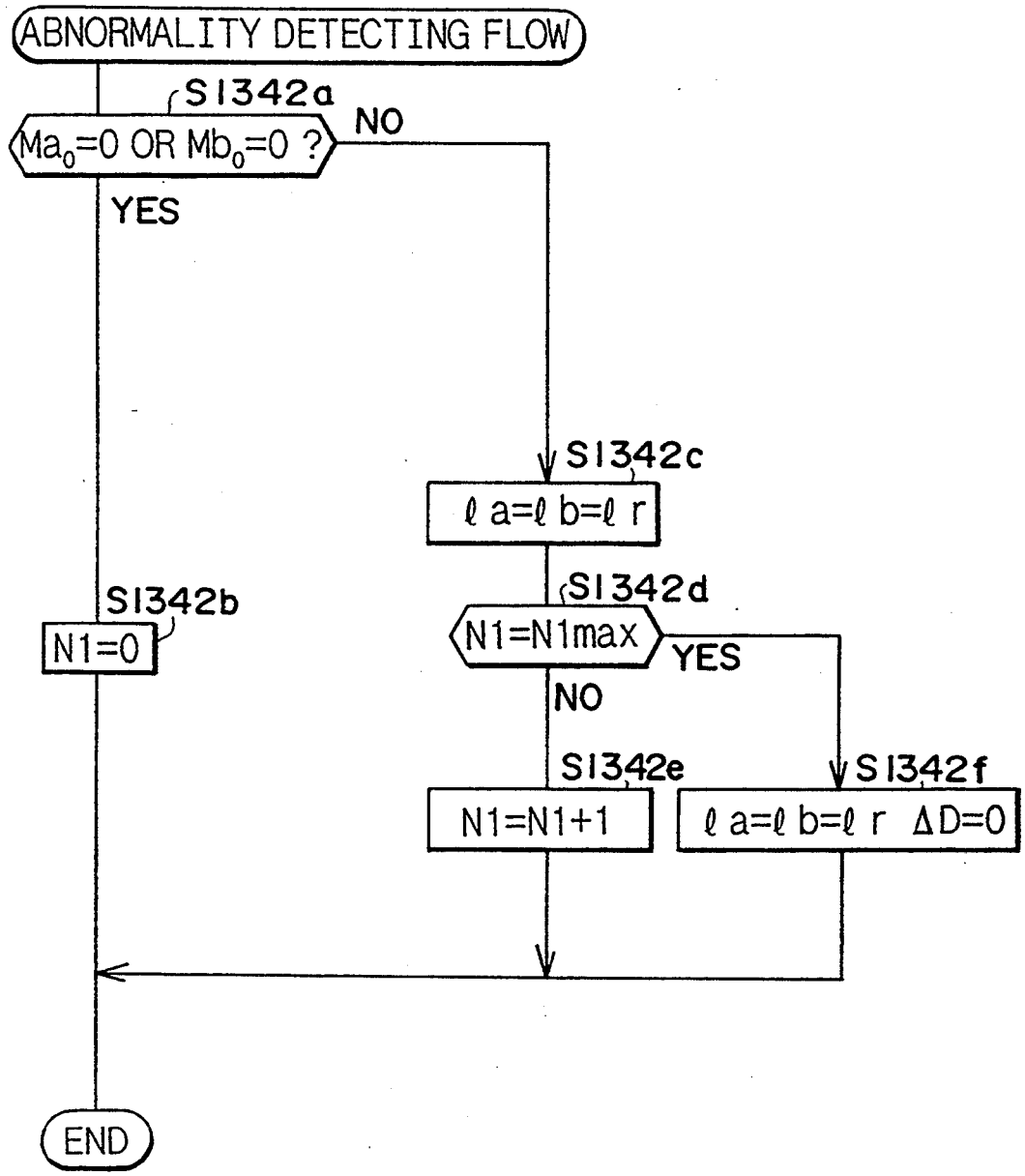

FIG. 46 is a detailed flowchart of compensation control for distance-undetectable signals.

At a step S1342a, it is first judged as to whether the distance signals SWA or SWB is normal. This judgment is carried out by judging as to whether the distance signal Ma0 or Mb0 transmitted from the distance monitoring unit 16 to the control device 12 is equal to zero. If the distance signals Ma0 and Mb0 are judged not to be zero, the distance signals SWA and SWB are judged to be normal, and the counter N1 is set to zero at th step S1342b to finish the program, the process being jumped to a step S1347 of FIG. 45.

At the step S1342a, if the distance signal SWA or SWB is judged to be abnormal (that is, Ma0 or Mb0=0), then the distance signal $1a$ and $1b$ are equal to $1r$ at a step S1342c. Thereafter, it is judged as a step S1342d as to whether a count value of the counter N1 is equal to N1max. At the initial stage, N1 is set to zero at the step S1342b, and thus the N1 is below the N1max. Therefore, the process goes to a step S1342e to add the count value of the counter N1 with 1, and this program is finished, the process being thereafter jumped to the step S1347 of FIG. 45.

Next, a series of processes for the step S1347 and the subsequent steps thereto will be described hereunder.

First, the process in a case where the distance signals SWA and SWB are judged to be normal (Ma0 and Mb0 are not equal to zero) will be described.

A positional relationship where the positioning of the distance sensor units 10a and 10b at the scan starting position is completed, corresponds to the positional relationship (I) as shown FIG. 25. In this case, the following equation is satisfied as described above.

$$1r=(1a1+1b1)/2 \qquad (55)$$

Here, $1r$ represents a destination value of the distance between the surface of the target W and the ultrasonic probes 10a and 10b.

The center line of the bracket 8D is accurately directed to the normal direction to the surface of the target W, and the distance between the ultrasonic probes 10a and 10b and the surface of the target W is accurately equal to the control instruction value.

In the positional relationship (I), an angle δ is calculated at the step S1347. Here, the angle δ represents an angular deviation between the center line of the bracket 8D and the normal direction to the surface of the target, and the angle δ is equal to zero in the position relationship (I). Next, an axis-position instructing value for the α-axis in the positional relationship (I) is calculated at the step S1348. Representing the axis-position instructing value for the α-axis and a current position of the α-axis by αr and α0, the following equation is satisfied because the angle δ is equal to zero.

$$\alpha r = \alpha 0 \qquad (56)$$

Next, axis-position instructing values for the X- and Z-axes are calculated at the step S1349. As shown in FIG. 25, the axis-position instructing values for the X- and Z-axes with which the bracket 8D is controlled to be moved from the positional relationship (I) to the positional relationship (II) are calculated by the following equation, where correction amounts for the X- and Z-axes are represented by ΔX1 and ΔX2.

$$\begin{aligned} Xr &= X_0 + \Delta X_1 \\ &= X_0 + \Delta D \cos \alpha r \end{aligned} \qquad (57)$$

$$\begin{aligned} Zr &= Z_0 + \Delta Z_1 \\ &= Z_0 + \Delta D \sin \alpha r \end{aligned} \qquad (58)$$

Next, the servo calculation and outputting operations are carried out using the respective axis-position instructing values which are obtained by the equations (56) to (58) and the current position of the ultrasonic probes 10a and 10b, and the timer interrupting program as shown in FIG. 45 is completed. At this time, the bracket 8D is in the positional relationship (II) as shown in FIG. 25.

Upon completion of the timer interrupting program as shown in FIG. 45, the process returns to the step S35 as shown in FIG. 44 to judge as to whether one scanning operation is completed. The step S35 is repeated until one scanning operation is completed.

When the process goes to the timer interrupting program again after the above repetitive operation of the step S35, the surface position of the target W is calculated and stored at the steps S341 to S346. If at this time the positional relationship of the bracket 8D corresponds to the state (II) as shown in FIG. 25, the angle δ is represented by the following equation (59) where D represents a distance between the ultrasonic probes 10a and 10b.

$$\delta = \tan^{-1}((1b2 - 1a2)/D) \qquad (59)$$

Therefore, the position instruction value αr for the α-axis is obtained by the following equation (60).

$$\alpha r = \alpha 0 = \delta \qquad (60)$$

In order to equalize the distance 1r to the value of (1a2+1b2)/2, the X-axis and Z-axis are first moved in a direction as indicated by an arrow A of FIG. 25. The correction values for the X- and Z-axes in this moving operation are represented by ΔX2 and ΔZ2. Next, the ultrasonic probes 10a and 10b are rotated by the angle δ with a point O at the rotational center. As a result, the ultrasonic probes 10a and 10b have positional relationship (III) shown in FIG. 25. The correction values for the X- and Z-axes in this rotating operation are presented by ΔX3 and ΔZ3, the position instructing values of the X- and Z-axes are represented by the following equations (61) and (62).

$$Xr = X0 + \Delta X1 + \Delta X2 + \Delta X3 \qquad (61)$$

$$Zr = Z0 + \Delta Z1 + \Delta Z2 + \Delta Z3 \qquad (62)$$

Thereafter, the step S1350 of FIG. 45 is carried out to move the bracket 8D to a next position, and the timer interrupting program is completed.

As described above, the timer interrupting program of FIG. 45 is executed at a constant time interval between the repetitive operations of the step S35 of FIG. 44 to store the positional coordinates X, Y and Z of the surface shape of the target W for one scanning operation. If it is judged at the step S37 of FIG. 44 that the shape measuring operation is completed, then the process proceeds to the flaw detecting operation of the step S40 of FIG. 5.

During the shape measuring operation as described above, if the distance signal SWA or SWB is judged to be abnormal (Ma0=0 or Mb0=0) in the step S1342a for the compensating control for the distance-undetectable signals as shown in FIG. 46, the distances 1a and 1b are set to be equal to 1r. Accordingly, the values of δ, ΔXE, ΔX3, ΔZ2 and ΔZ3 which are obtained at the steps S1347 and S1348 subsequent to the step S1342 are zero-values, respectively, and thus the ultrasonic probes 10a and 10b are moved in the tangent direction to the surface of the target W along the X-axial direction by a distance ΔD while kept at the orientational state at the time when the abnormality is detected for the signals SWA or SWB.

If the number of judgments of the abnormality for the signals SWA and SWB reaches the value of N1max in the compensating control process, then the process goes to a step S1342f to set 1a and 1b to 1r and set ΔD to zero and the program for this process is completed. Therefore, when the equations (57) to (62) are calculated at the subsequent steps S1347 to S1349, the values of δ, ΔX1 to ΔX3 and ΔZ1 to ΔZ3 are zero, and thus the conditions that αr=α0 and Xr=X0 are satisfied, so that the ultrasonic probes 10a and 10b are stopped.

According to the sixth embodiment as described above, in a case where a distance between the surface of the target W and the ultrasonic probes 10a and 10b is undetectable due to flaws on the surface of the target or failure of the signal transmission or reception, the ultrasonic probes 10a and 10b are controlled to be moved to a next scanning position while the orientation thereof remains unchanged. Therefore, the shape measuring operation can be smoothly continued without interruption due to abnormality of the detection signals. Further, When no distance can be detected due to an extremely large flaw or an obstacle of the distance sensor unit (that is, N1=N1max), the shape measuring operation is ceased. Accordingly, there occurs no problem that the distance sensor unit erroneously impinges upon the surface of the target W, and thus the flaw detection can be safely carried out.

(3) Process for the flaw detecting operation

The process for the flaw detecting operation of this embodiment is identical to that of the first embodiment, and is shown as a flaw detecting flow 1 in FIG. 12 The process of the step S41 of the flow 1 is also identical to that (flaw detecting flow2) of FIG. 13. However, this embodiment differs from the first embodiment in the flaw detecting flow 3 for the flaw detecting operation which is executed through the step S44 of FIG. 12.

Figure 47:
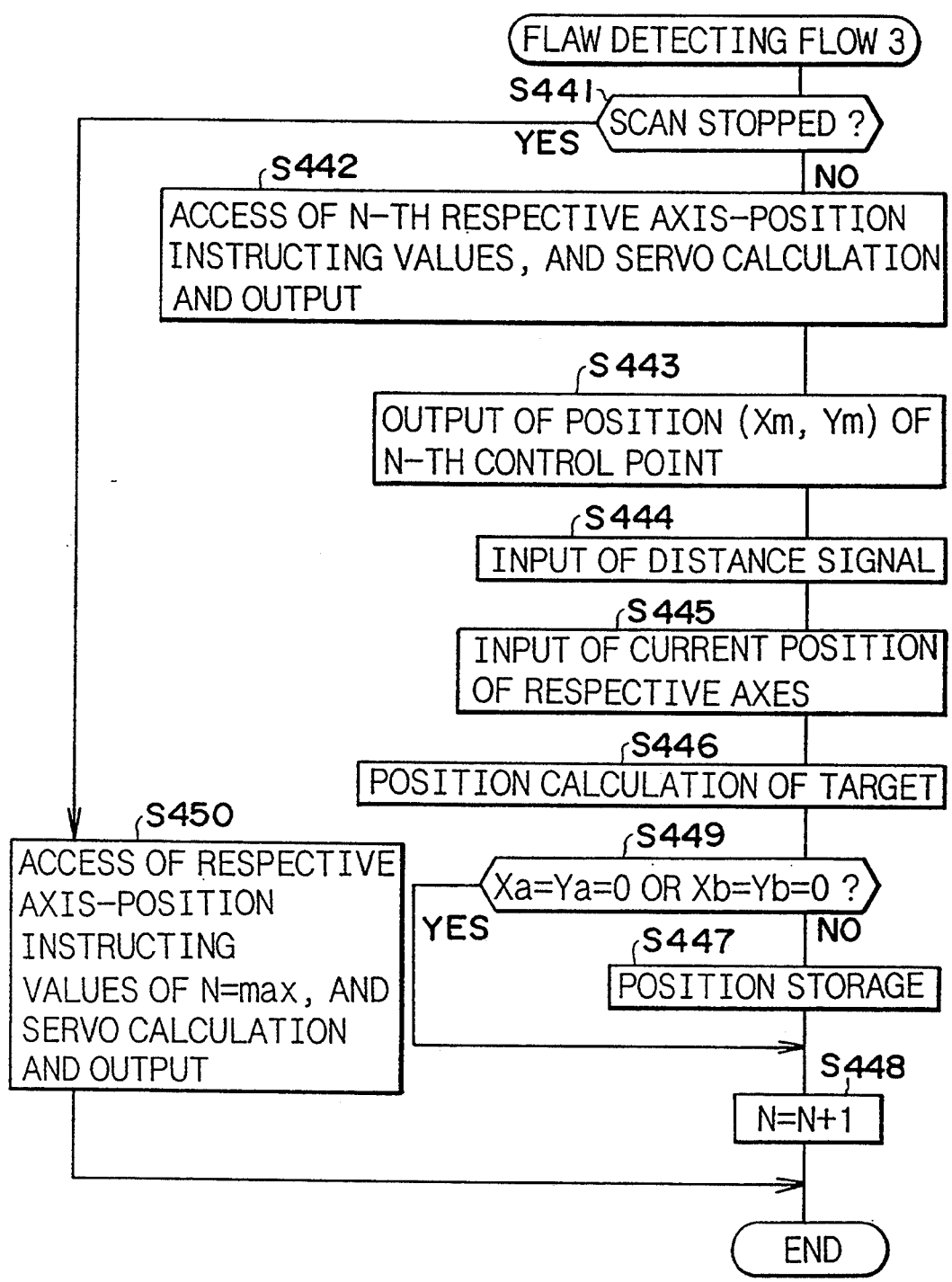

FIG. 47 is a flowchart (flaw detecting flow for the flaw detecting operation of this embodiment. The same steps as those of the flaw 3 (in FIG. 17) of the first embodiment are represented by the same reference numerals.

At a step S441 of the program of FIG. 47, it is judged as to whether a scan stopping instruction signal is outputted. If no scan-stoping instruction signal is judged to be outputted, at a step S442 the N-th axis-position instructing values for the respective axis driving members are accessed and the servo computing and outputting operations are carried out. These operations are carried out using the position feedback control and the speed feedforward control as shown in FIG. 18. Thereafter, the process goes to a step S443 to take in an output of the ultrasonic probe 9 and to output a flaw-detection result to the storing device 15 as a position data (Xm, Ym) for a control point. Next, processes of steps S444 to S448 which are similar to the steps S344 to S346 are successively carried out, and a shape measuring operation for a preceding scanning line (indicated by a dotted line) is carried out in parallel with (simultaneously with) the flaw detecting operation for a current scanning line as shown in FIG. 18. That is, the position on the surface of the target W upon which the ultrasonic beams of the ultrasonic probes 10a and 10b are radiated are stored in each storing sub-area as shown in FIG. 9. In this case, the position data is not stored if the value of the distance signal is judged to be an abnormal value at a step S449.

In summary, the surface shape measuring and flaw detecting operations of the target W in the embodiment as described above are carried out as follows.

(a) A surface shape of the target is beforehand measured on the basis of a detection result of the distance sensor units 10a and 10b which are actuated for a scanning line preceding to a current scanning line for the flaw detection. Concretely, a position coordinate (X, Y, Z) on the surface of the target onto which the ultrasonic beams of the distance sensor units 10a and 10b are radiated are calculated and stored. This data is stored on one of storing sub-areas into which a storing area is divided in the X-Y plane. Only one position data is stored in each storing sub-area.

(b) In the shape measuring operation as described above, the distance signals SWA and SWB are picked up at a short sampling time interval to judge the abnormality of the signals, and the position data is not stored if the abnormality is judged.

(c) On the basis of the data obtained through the shape measuring operation, the distance sensor units are controlled in orientation so that the detection signals SWA and SWB of the distance sensor units 10a and 10b are equal to a destination value of 1r, that is, 1a and 1b are equal to 1r, thereby performing a trace-scanning of the surface of the target while a detecting direction of the distance sensor units 10a and 10b are coincident with a normal direction to the surface of the target and the distance sensor units are spaced from the surface of the target by a distance corresponding to the destination value of 1r.

(d) When the distance signals are judged to be abnormal, the distance sensor units are moved by one pitch in a tangent direction along the X-axial direction vertical to the normal direction to the surface of the target while left oriented in a previous normal direction.

(e) The processes of (a) and (d) are repeated until the distance sensor units are moved by a distance L.

(f) Temporal axis-position instructing values at each control point for the flaw-detecting ultrasonic probe 9 (which is spaced away from the surface of the target W by a predetermined distance and whose ultrasonic beam is directed to a normal direction to the surface of the target W) are calculated from the surface shape data which are stored in the storing sub-areas through the processes (a) to (e), and then plural axis-position instructing values thus calculated are averaged to obtain the respective axis-position instructing values for each control point.

(g) The respective axis-speed instructing values for the control point is calculated from the averaged axis-position instructing values, and an averaged axis-speed instructing value for any control point is calculated from the axis-speed instructing values of plural control points.

(h) A deviation between the averaged axis-position instructing value and a current (actual) position is obtained to calculate an axis-speed instructing value for the deviation. The axis-speed instructing value for the deviation and the averaged axis-speed instructing value are summed to output a sum result. The respective axis-driving members are controllable with the sum result.

(i) A detection signal from the ultrasonic probe 9 is received at each control point to perform the flaw detection of the target (j) In parallel with the flaw detecting operation, the shape measuring operation for a preceding scanning line to a current scanning line for the flaw detection is carried out.

Accordingly, an inaccurate position data which is caused by a flaw on the surface of the target or the like is excluded or eliminated from the position data for the shape measurement, so that the flaw detection is accurately performed and the ultrasonic probe is smoothly controlled for the scanning operation.

INDUSTRIAL APPLICABILITY

This invention is utilizable as a flaw-detecting apparatus for detecting a flaw, a defect and the like on the surface or inside of various works having curved surfaces using an ultrasonic wave.

We claim:

1. An ultrasonic flaw detector comprising:
   an ultrasonic probe for radiating an ultrasonic flaw-detecting signal onto each flaw detection point within a flaw detection area which is specified on a surface of a target, and receiving an ultrasonic wave reflected from the detection point;
   distance sensor means for radiating a distance measuring signal onto a measuring point within a position storing area including the flaw detection area to detect a distance between the measuring point and said distance means;
   coupling means for integrally coupling said distance sensor means and said ultrasonic probe in such a manner that said distance sensor means scans a preceding scanning line;
   position and orientation control means for controlling position and orientation of said ultrasonic probe and said distance sensor means;

shape information calculation means for calculating information on the shape of the position storing area including the flaw detection area on the basis of a detection result of said distance sensor means and a current position of said distance sensor means;

storing means for storing the shape information;

position and orientation calculation means for calculating position and orientation of said ultrasonic probe on the basis of the shape information stored in said storing means to thereby radiate the flaw detecting signal onto the measuring point at predetermined angle and distance from said ultrasonic probe; and control means for performing a shape-measurement scanning operation of said distance sensor means and a flaw-detection scanning operation of said ultrasonic probe in parallel with each other.

2. The ultrasonic flaw-detector as claimed in claim 1, wherein the position storing area including the flaw detection area is divided into plural sub-areas, and wherein said storing means has plural storing areas each corresponding to each of said sub-areas, said sub-area storing only one position information.

3. The ultrasonic flaw-detector as claimed in claim 2, wherein each of said ultrasonic probe and said distance sensor means performs a scanning operation in a two-dimensional plane which is defined by X-axis and Y-axis, the shape information is defined by positions in the X- and Y-axes and a position in the Z-axis which is vertical to the X- and Y-axes, the storing area corresponding to each sub-area is accessed using an address corresponding to the positions of X- and Y-axes, and a position information of the X-, Y- and Z-axes of sensor distance measuring point within the position storing area including the flaw detection area is stored in a storing area of each address.

4. The ultrasonic flaw-detector as claimed in claim 2, wherein said position and orientation calculation means performs a calculation of the position and orientation of said ultrasonic probe on the basis of the shape information of plural sub-areas which surround the sub-area corresponding to the flaw detection point.

5. The ultrasonic flaw-detector as claimed in claim 1, wherein said distance sensor means and said ultrasonic probe for flaw detection are disposed on a common substrate, and wherein said distance sensor means includes a pair of distance sensors, said distance sensors being arranged in a scanning direction corresponding to a curvature-varying direction of the surface of the target to measure the surface shape of the target, and in such a manner as to scan a position storing area preceding to a flaw detection point of said ultrasonic probe in a scanning operation.

6. The ultrasonic flaw-detector as claimed in claim 2, wherein said distance sensor means and said ultrasonic probe for flaw detection are disposed on a common substrate, and wherein said distance sensor means includes a pair of distance sensors, said distance sensors being arranged in a scanning direction corresponding to a curvature-varying direction of the surface of the target to measure the surface shape of the target, and in such a manner as to scan a position storing area preceding to a flaw detection point of said ultrasonic probe in a scanning operation.

7. The ultrasonic flaw-detector as claimed in claim 3, wherein said distance sensor means and said ultrasonic probe for flaw detection are disposed on a common substrate, and wherein said distance sensor means includes a pair of distance sensors, said distance sensors being arranged in a scanning direction corresponding to a curvature-varying direction of the surface of the target to measure the surface shape of the target, and in such a manner as to scan a position storing area preceding to a flaw detection point of said ultrasonic probe in a scanning operation.

8. The ultrasonic flaw-detector as claimed in claim 1, wherein said ultrasonic flaw-detector serves to perform flaw detection for a cylindrical target and further includes rotating means for rotating the target with respect to a predetermined rotational axis, and wherein the position storing area including the flaw detection area is divided into plural sub-areas which are segmented by a rotational angle and a position in the rotational axis and the storing means has a storing area corresponding to each sub-area, said storing area storing only one shape information.

9. The ultrasonic flaw-detector as claimed in claim 8, wherein said ultrasonic probe and said distance sensor means performs a Z-axial scanning operation, the shape information is defined by the Z-axial position, the rotational angle $\gamma$ and a radial distance D1 between the measuring point and the Z-axis, and the storing area corresponding to the sub-area is accessed using an address which is defined by Z-axial position and the rotational angle $\gamma$, the storing area of each address storing information on the rotational angle $\gamma$, the Z-axial position and the radial distance D1 for the distance measuring point within the position storing area including the flaw detection area.

10. An ultrasonic flaw detector comprising:

an ultrasonic probe for radiating an ultrasonic flaw-detecting signal onto each flaw detection point within a flaw detection area which is specified on a surface of a target, and receiving an ultrasonic wave reflected from the detection point;

distance sensor means for radiating a distance measuring signal onto a measuring point within a position storing area including the flaw detection area to detect a distance between the measuring point and said distance means;

coupling means for integrally coupling said distance sensor means and said ultrasonic probe in such a manner that said distance sensor means scans a scanning line which precedes to a scanning line scanned by said ultrasonic probe;

position and orientation control means having plural axis-driving means for controlling position and orientation of said ultrasonic probe and said distance sensor means through control of said axis-driving means;

shape information calculation means for calculating information on the shape of the position storing area including the flaw detection area on the basis of a detection result of said distance sensor means and a current position of said distance sensor means;

storing means for storing the shape information;

position and orientation calculation means for calculating position and orientation of said ultrasonic probe on the basis of the shape information stored in said storing means to thereby radiate the flaw detecting signal onto the measuring, point at predetermined angle and distance from said ultrasonic probe;

control means for performing a shape-measurement scanning operation of said distance sensor means and a flaw-detection scanning operation of said ultrasonic probe in parallel with each other;

axis-position detecting means for detecting current positions of respective axes;

axis-position instructing value calculating means for calculating axis-position instructing values for each flaw detection point of said ultrasonic probe on the basis of the current positions detected by said axis-position detecting means and the shape information which is beforehand obtained;

axis-position instructing value averaging means for calculating an averaged value of axis-position instructing values of plural flaw-detection points including a flaw-detection point to be concerned on the basis of the respective axis-position instructing values of each flaw detection point which are calculated by said calculation means to thereby specify an axis-position instructing value for the flaw-detection point to the averaged value;

axis-speed instructing value calculating means for calculating an axis-speed instructing value for each flaw-detecting point on the basis of the axis-position instructing values for each flaw-detecting point which are calculated by said averaging means;

axis-speed instructing value averaging means for calculating an averaged value of the axis-speed instructing values for plural flaw-detection points including a flaw-detection point to be concerned to thereby specify an axis-speed instructing value for the flaw-detection point to the averaged value; and axis-speed control means for calculating an axis-speed instructing value in accordance with a deviation between the averaged axis-position instructing value and the current position detected by said axis-position detecting means, and controlling a moving speed of each axis for said ultrasonic probe on the basis of a sum of the calculated axis-speed instructing value and the averaged axis-speed instructing value.

11. The ultrasonic flaw-detector as claimed in claim 10, wherein said storing means has plural storing areas each corresponding to each of sub-areas into which the position storing area including the flaw detection area is divided, said sub-area storing only one position information, and wherein the axis-position instructing values are averaged on the basis of the shape information in plural subareas which include the sub-area corresponding to the flaw detection area and surround the sub-area.

12. The ultrasonic flaw-detector as claimed in claim 10, wherein said axis-position instructing value calculation means, said axis-position instructing value averaging means, said axis-speed instructing value calculation means and said axis-speed instructing value averaging means are actuated to calculate an averaged axis-position instructing value and an averaged axis-speed instructing value for each flaw detection point of a next flaw-detection scanning line during a flaw detecting operation of said ultrasonic probe for a current scanning line.

13. The ultrasonic flaw-detector as claimed in claim 2, further comprising;

abnormality detecting means for judging as to whether an output of said distance sensor means is abnormal, and outputting an abnormality-detection signal;

prohibiting means for prohibiting a storing operation of a currently-calculated shape information in said storing means when an abnormality-detection signal is outputted; and drive control means for controlling said distance sensor means so that a detecting direction of said distance sensor means is directed to a currently-calculated normal direction while said distance sensor means is kept away from the target by a destination value, and the distance sensor means is moved by one pitch in a tangent direction along the X-axis vertical to the normal direction when no abnormality-detection signal is outputted, and for controlling said distance sensor means so that said distance sensor means is moved by one pitch in a tangent direction along the X-axis vertical to a previously-calculated normal direction while the orientation thereof is kept when the abnormality-detection signal is outputted.

14. The ultrasonic flaw-detector as claimed in claim 11, further comprising;

abnormality detecting means for judging as to whether an output of said distance sensor means is abnormal, and outputting an abnormality-detection signal;

prohibiting means for prohibiting a storing operation of a currently-calculated shape information in said storing means when an abnormality-detection signal is outputted; and drive control means for controlling said distance sensor means so that a detecting direction of said distance sensor means is directed to a currently-calculated normal direction while said distance sensor means is kept away from the target by a destination value, and the distance sensor means is moved by one pitch in a tangent direction along the X-axis vertical to the normal direction when no abnormality-detection signal is outputted, and for controlling said distance sensor means so that said distance sensor means is moved by one pitch in a tangent direction along the X-axis vertical to a previously-calculated normal direction while the orientation thereof is kept when the abnormality-detection signal is outputted.

* * * * *